US007425336B2

(12) United States Patent
Minke et al.

(10) Patent No.: US 7,425,336 B2
(45) Date of Patent: Sep. 16, 2008

(54) CANINE INFLUENZA VACCINES

(75) Inventors: Jules Maarten Minke, Corbas (FR);
Kemal Karaca, Athens, GA (US);
Jiansheng Yao, North York (CA)

(73) Assignee: Mevial Limited, Duluth, GA (US)

( * ) Notice: Subject to any disclaimer, the term of this patent is extended or adjusted under 35 U.S.C. 154(b) by 0 days.

(21) Appl. No.: 11/264,622

(22) Filed: Nov. 1, 2005

(65) Prior Publication Data
US 2007/0048821 A1 Mar. 1, 2007

Related U.S. Application Data

(63) Continuation-in-part of application No. 11/211,983, filed on Aug. 25, 2005.

(51) Int. Cl.
*A61K 39/145* (2006.01)
*A61K 39/12* (2006.01)
*A61K 45/00* (2006.01)
*C12N 9/99* (2006.01)
*C12Q 1/68* (2006.01)

(52) U.S. Cl. .............. 424/209.1; 424/204.1; 424/283.1; 435/6; 435/184

(58) Field of Classification Search ........................ None
See application file for complete search history.

(56) References Cited

FOREIGN PATENT DOCUMENTS

WO    WO9944633 A1    9/1999

OTHER PUBLICATIONS

Paoletti, Application of pox virus vectors to vacination: An update, Proceedings of the National Academy of Sciences of the United States of America, Oct. 1996, vol. 93, pp. 11349-11353.*
Daly et al., Current perspectives on control of equine influenza, Veterinary Research, 2004, vol. 35, pp. 411-423.*
Takada et al., Intranasal immunization with formalin-inactivated virus vaccine induces a broad spectrum of heterosubtypic immunity against influenza A virus infection in mice, Vaccine, 2003, vol. 21, pp. 3212-3218.*
Smirnov et al., Influenza H5 virus escape mutants: immune protection and antibody production in mice, Virus Research, 2004, vol. 99, pp. 205-208.*
Youngner et al., Derivation and characterization of a live attenuated equine influenza vaccine virus, American Journal of Veterinary Research, Aug. 2001, vol. 62, No. 8, pp. 1290-1294.*
Mayr. Prophylactic Vaccination of Animals and Human Health. Zbl. Bakteriol. Hyg., I Abt. Orig. B, 1985, vol. 180, No. 2-3, pp. 175-189. (German).*
Science Daily, Equine influenza Virus Likely Involved in Recent Respiratory Disease Outbreak in Racing Greyhounds. University of Florida news release, Apr. 29, 2004, 2 pages.*
Cornell Veterinary Magazine, [Online] 2004, pp. 10-13, Retrieved from the Internet: URL:http://www.vet.cornell.edu/news/cvmagazine/Fall04/detectives.pdf See p. 11, last sentence of first (incomplete) paragraph.
Crawford P C et al: "Transmission of Equine influenza virus to dogs" Science, American Association for the Advancement of Science US, vol. 310, No. 5747, Oct. 21, 2005, pp. 482-485.
Dubovi EJ, Crawford PC, Donis RO, Castelman WL, Stephenson I. Gibbs EPJ: "Isolation of Equine Influenza Virus from Racing Greyhounds with Fatal Hemorrhagic Pneumonia" Proceedings of the 47th Annual Meeting of American Association of Veterinary Laboratory Diagnosticians, Oct. 2004, p. 158.
Edlund Toulemonde C et al: "Efficacy of a recombinant equine influenza vaccine against challenge with an American lineage H3N8 influenza virus responsible for the 2003 outbreak in the United Kingdom." The Veterinary Record Mar. 19, 2005, vol. 156, No. 12, Mar. 19, 2005, pp. 367-371.
Enserink Martin: "Epidemiology. Horse flu virus jumps to dogs" Science, American Association for the Advancement of Science US, vol. 309, No. 5744, Sep. 30, 2005, p. 2147.
Karaca Kemal et al: "Evaluation of the ability equine influenza virus of canarypox-vectored vaccines to induce humoral immune responses against canine influenza viruses in dogs" American Journal of Veterinary Research, vol. 68, No. 2, Feb. 2007, pp. 208-212.
Stephensen CB et al: "Canine Distemper Virus (CDV) infection of ferrets as a model for testing Morbillivirus strategies: NYVAC- and ALVAC-based CDV recombinants protect against symptomatic infection" Journal of Virology, The American Society for Microbiology, US, vol. 71, No. 2, Feb. 1997, pp. 1506-1513.
Wood J M et al: "The standardization of inactivated equine influenza vaccines by single-radial immunodiffusion" Journal of Biological Standardization, Academic Press, London, GB, vol. 11, No. 2, Apr. 1983, pp. 133-136.
J.M. Minke et al., "Use of DNA and recombinant canarypox viral (ALVAC) vectors for equine herpes virus vaccination" Veterinary Immunology and Immunopathology, vol. 111, pp. 47-57, 2006.
K. Karaca et al .., "Recombinant canarypox vectored West Nile virus (WNV) vaccine protects dogs and cats against mosqito MNV challenge" Vaccine 23, pp. 3808-3813, 2005.

* cited by examiner

*Primary Examiner*—Bruce Campbell
*Assistant Examiner*—Sharon Hurt
(74) *Attorney, Agent, or Firm*—Judy Jarecki-Black; Mevial Limited; Thomas Kowalski, Esq.

(57) ABSTRACT

The present invention encompasses influenza vaccines, in particular canine influenza vaccines. The vaccine may be a recombinant poxvirus vaccine or an inactivated vaccine. The invention also encompasses recombinant poxvirus vectors encoding and expressing influenza antigens, epitopes or immunogens which can be used to protect animals, in particular dogs, against influenza.

18 Claims, 14 Drawing Sheets

FIGURE 1

```
GTATTCTAAACTAGGAATAGATGAAATTATGTGCAAAGGAGATACCTTTAGATATGGATCTGATTTAT
TTGGTTTTTCATAATCATAATCTAACAACATTTTCACTATACTATACCTTCTTGCACAAGTCGCCATTA
GTAGTATAGACTTATACTTTGTAACCATAGTATACTTTAGCGCGTCATCTTCTTCATCTAAAACAGATT
TACAACAATAATCATCGTCGTCATCTTCATCTTCATTAAAGTTTTCATATTCAATAACTTTCTTTTCTAA
AACATCATCTGAATCAATAAACATAGAACGGTATAGAGCGTTAATCTCCATTGTAAAATATACTAACG
CGTTGCTCATGATGTACTTTTTTTTCATTATTTAGAAATTATGCATTTTAGATCTTTATAAGCGGCCGT
GATTAACTAGTCATAAAAACCCGGGATCGATTCTAGACTCGAGCGGCCGCCAGTGTGATGGATATCT
GCAGAATTCGGCTTTGGTCCTTACTCAAATGCAAATGTTGCACCTGATGTTGCCTTTTTGGCAAGCCC
ACATAATGAAACCCAATAGAACAACGCAAATTAAGAAGCATGATATGGCGAATGAAATCCACAGTAT
CCAATCTTTGTAGCCTGATTTCAACTCAACACTTTTGATTTGAAATCGGTTGTTTAATGCTTCATCTCT
GTATATGTAATGGTCATATGTCCCATTTCTTATTGATCCAATGCATGCATTATCACATTTGTGGTAAAT
CTTGAAACATCCACCTCCCATGTCTTCCGCGTTTTCTCTTAACTGGCGCCTAGTCTTCTCGAATAATTT
ATTCATTTCTGCATCTGTTAAGTCAATTGTATGTTGATTTTCTAGAGCCACCAGCAATTCTGCATTGTA
GGACCATAGGTCTATTTTGGTGTCTTCTACATACTTCTCCAAATCCTGGATTCTCCCTTCTACTTCTGA
GAATTCCTTTTCTATTTGATGGAATTTCTCATTGGTCCTTTCAATCACTCTGTTTAATTTTCCATTGATC
TGGTCTATGGCTGCTTGAGTGCTCTTTAGATCTGCAGCTTGTCCTGTTCCTTCCGAGTTTTGATATCG
GAATCCATACCACCCATCAACCATTCCTTCCCAGCCGTTTTCTATGAATCCCGCTATTGCTCCAAAGA
TTCCTCTGATTTGCTTTTCTGGTACATTCCTCATCCCAGTGGCCAGCTTTAAAGTGTTTTGCCTGATAT
ACTTGGGGCATTTTCCATATGTAATTTTGTTCACATTTTGAAATGGTTTGTCGTTGGGGATGCTTCCAT
TTGGTGTAATACATTCAGACACACAAGTGTCTATGAGTGCATCTGATCTCATTACAGAGCTTTTCCCT
GTTCTCAATTTAAAATATCCCCGCGGTGCAACTAAGTTGCCATTACTGTTTATCATTAGAATATCTCCA
GGTTTTACAATGGTCCAGTATATGCTTATCCTGCCTGATTGACCCCTGACCCACGGCCTAGATCCGAT
GTTAGGGATTACTGTTTGTTGACTTCTTTCTGTTGAGACTGTTACTCGTCCTGATTCTTGGATATATAA
TTTTGTCTGCTCTTTGTTTGAGCTCGGGTGATGAATCCCCCAGATGTATAGTTTATCGAAATTTTTATT
GTTAGGCATTGTCACATTCAATATGGGGTAAGAATTTCCAGATTTTGTTAGCCAATTCAGTCGGCTAA
AGAAACTATCGGCTGATCCCCTTTTGCAGGCTCCACTTCTTCCGTTTTGAGTGACACCTGTCCATGTG
AACCCCTCTGCTGTGAATTCTAATGTTCCTGAGGATGCTACAATGGACCGGAGCGATGCATAGTCAG
GGATGTCATATGGGTAGCAATTGCTGAAAGCGCTGCTTCTTTCTATGAAGAGGTCCCAATTCTCATAC
TGAAAATCATCACAATGGGGGTCTCCTAGCATTGCATCTATTAATGTGCAATTTCTTCCATCTAGAAC
CCTATATGAGTTGTTGCATATTTTCCCTATTGAAATGCTCTGGACTAATTCAGTAGCATTTGTCACCTC
AATTTGGTCATCAGTTATTGTTTTACCAATGTTCCATTTGCTACTGCATGGTGTCCCAGACATAATGT
GGCTGTGTTGTTGCCACTGGTTGGGTTTTGACTGTAGACCCAATGGGTCAGTAGTATCAAAATAATG
GTTGTCTTCATTACGATACAAACTTAACGGATATCGCGATAATGAAATAATTTATGATTATTTCTCGCT
TTCAATTTAACACAACCCTCAAGAACCTTTGTATTTATTTTCACTTTTTAAGTATAGAATAAAGAAGCT
CTAATTAATTAACGAGCAGATAGTCTCGTTCTCGCCCTGCCTGATGACTAATTAATTAACCCGGATCC
TTTTTATAGCTAATTAGTCACGTACCTTTGAGAGTACCACTTCAGCTACCTCTTTTGTGTCTCAGAGTA
ACTTTCTTTAATCAATTCCAAAACAGTATATGATTTTCCATTTCTTTCAAAGATGTAGTTTACATCTGCT
CCTTTGTTGAAAAGTAGCCTGAGCACTTCTTTTCTACCATGAATTACAGCTGGCAAGATCAATTTTTCC
CAGTTCTGGACATTTTATTTTTTTTAAGTAGTGTGCTACATATTTCAATATTTCCAGATTGTACAGCGA
TCATTAAAGGAGTACGTCCCATGTTATCCAGCAAGTCAGTATCAGCACCTTTGTTCAATAGAAGTTTA
ACCATTGTTAAATTTTTATTTGATACGGCTATATGTAGAGGAGTTAACCGATCCGTGTTTGAAATATCT
ACATCCGCCGAATGAGCCAATAGAAGTTTAACCAAATTAACTTTGTTAAGGTAAGCTGCCAAACACAA
AGGAGTAAAGCCTCCGCTGTAAAGAACATTGTTTACATAGTTATTCTTCAACAGATCTTTCACTATTTT
GTAGTCGTCTCTCAACACCGCATCATGCAGACAAGAAGTTGTGCATTCAGTAACTACAGGTTTAGCT
CCATACCTCATCAAGATTTTTATAGCCTCGGTATTCTTGAACATTACAGCCATTTCAAGAGGAGATTG
TAGAGTACCATATTCCGTGTTAGGGTCGAATCCATTGTCCAAAAACCTATTTAGAGATGCATTGTCAT
TATCCATGATAGCCTCACAGACGTATATGTAAGCCATCTTGAATGTATAATTTTGTTGTTTTCAACAAC
CGCTCGTGAACAGCTTCTATACTTTTTCATTTTCTTCATGATTAATATAGTTTACGGAATATAAGTATA
CAAAAAGTTTATAGTAATCTCATAATATCTGAAACACATACATAAAACATGGAAGAATTACACGATGT
CGTTGAGATAAATGGCTTTTTATTGTCATAGTTTACAAATTCGCAGTAATCTTCATCTTTTACGAATAT
```

Continuation of FIGURE 1

```
TGCAGAATCTGTTTTATCCAACCAGTGATTTTTGTATAATATAACTGGTATCCTATCTTCCGATAGAAT
GCTGTTATTTAACATTTTTGCACCTATTAAGTTACATCTGTCAAATCCATCTTTCCAACTGACTTTATGT
AACGATGCGAAATAGCATTTATCACTATGTCGTACCCAATTATCATGACAAGATTCTCTTAAATACGTA
ATCTTATTATCTCTTGCATATTCGTAATAGTAATTGTAAAGAGTATACGATAACAGTATAGATATACAC
GTGATATAAATATTTAACCCCATTCCTGAGTAAAATAATTACGATATTACATTTCCTTTTATTATTTTTA
TGTTTTAGTTATTTGTTAGGTTATACAAAAATTATGTTTATTTGTGTATATTTAAAGCGTCGTTAAGAAT
AAGCTTAGTTAACATATTATCGCTTAGGTTTTGTAGTATTTGAATCCTTTCTTTAAATGGATTATTTTTC
CAATGCATATTTATAGCTTCATCCAAAGTATAACATTTAACATTCA (SEQ ID NO: 1)
```

FIGURE 2

```
GTATTCTAAACTAGGAATAGATGAAATTATGTGCAAAGGAGATACCTTTAGATATGGATCTGATTTATTTGGTTTTT
CATAATCATAATCTAACAACATTTTCACTATACTATACCTTCTTGCACAAGTCGCCATTAGTAGTATAGACTTATAC
TTTGTAACCATAGTATACTTTAGCGCGTCATCTTCTTCATCTAAAACAGATTTACAACAATAATCATCGTCGTCATC
TTCATCTTCATTAAAGTTTTCATATTCAATAACTTTCTTTTCTAAAACATCATCTGAATCAATAAACATAGAACGGT
ATAGAGCGTTAATCTCCATTGTAAAATATACTAACGCGTTGCTCATGATGTACTTTTTTTTCATTATTTAGAAATTA
TGCATTTTAGATCTTTATAAGCGGCCGTGATTAACTAGTCATAAAAACCCGGGATCGATTCTAGACTCGAGGGTACC
TCAAATGCAAATGTTGCATCTGATGTTGCCTTTTTGGCAAGCCCACATAATGAAACCCAATAGAACAACGCAAATTA
AGAAGCATGATATGGCGAATGAAATCCACAGTATCCAATCTTTGTAGCCTGATTTCAACTCAACACCTTTGATTTGA
AATCGGTTGTTTAATGCTTCATCTCTGTATATGTAATGGTCATATGTCCCATTTCTTATTGATCCAATGCATGCATT
ATCACATTTGTGGTAAATCTTGAAACATCCACCTCCCATGTCTTCCGCGTTTTCTCTTAACTGGCGTCTAGTCTTCT
CGAATAATTTATTCATTTCTGCATCTGTTAAGTCAATTGTATGTTGATTTTCTAGAGCCACCAGCAATTCTGCATTG
TAGGACCATAGGTCTATTTTGGTGTCTTCTACATACTTCTCCAAGTCCTGGATTCTCCCTTCTACTTCTGAGAATTC
CTTCTCTATTTGATGGAATTTCTCATTGGTCCTTTCAATCACTCTGTTTAATTTTCCATTAATCTGGTCGATGGCTG
CTTGAGTGCTCTTTAGATCTGCAGCTTGTCCTGTTCCTTCCGAGTTTTGATATCGGAATCCATACCACCCATCAACC
ATTCCTTCCCAGCCGTTTTCTATGAATCCCGCTATTGCTCCAAAGATTCCTCTGATTTGCTTTTCTGGTACATTCCT
CATCCCAGTGGCCAGCTTTAAAGTGTTTTGCCTGATATACTTGGGGCATTTTCCATATGTAACTTTGTTCACATTTT
GAAATGGTTTGTCGTTGGGGATGCTTCCATTTGGTGTAATACATTCAGACACACAAATGTCTATGGGTGCATCTGAT
CTCATTACAGAGCTTTTCCCTGTTTTCAATTTAAAATATCCCCGCGGTGCAACTAAGTTGCCATTACTGTTTATCAT
TAGGATATCTCCAGGTTTTACAATGGTCCAGTATATGCTTATCCTGCCTGATTGACCCCTGACCCACGGTCTAGATC
CGATATTAGGGATTATCGTTTGTTGACTTCTTTTTGTTGAGACTGTTACTCGTCCTGATTCTTGGATGTACAATTCT
GTTTGCTGTTGGTTTGAGCTCGGGTGATGAATCCCCCAGATGTATAGTTTGTCGAAATTTTTATTGTTAGGCATTGT
CACATTCAATGTGGGTAAGAGTTTCCAGATTTTGTTAGCCAATTCAGTCGGCTAAAGAAACTATCGGCTGATCCCC
TTTTGCAGGCTCCACTTCTTCCGTTTTGAGTGACACCTGTCCATGTGAATCCCTCTGCTGTGAATTCCAATGTTCCT
GAGGATGCTACAATGGACCGGAGCGATGCATAGTCAGGGATGTCATATGGGTAGCAATTGCTGAAAGCGCTGCTTCT
TTCTATGAAGAGGTCCCAATTCTCATACTGAAAGACATCACAGTGGGGGTCTCCTAGCATTGCATCTATTAATGTGC
AATTTCTTCCATCTAGAACTCTATATGAGTTGTTGCATATTTTCCCTATTGAAATGCTCTGAACTAATTCAGTAGCA
TTTGTCACCTCAATTTGGTCATCAGTTATTGTTTTTACCAATGTTCCATTTGCTACTGCATGGTGTCCCAGACATAA
TGTGGCTGTGTTGTTGCCACTGGTTGGGTTTTGACTGTAGACCCAATGGGTCAGTAGTATCAAAATAATGGTTGTCT
TCATTACGATACAAACTTAACGGATATCGCGATAATGAAATAATTTATGATTATTTCTCGCTTTCAATTTAACACAA
CCCTCAAGAACCTTTGTATTTATTTTCACTTTTTAAGTATAGAATAAAGAAGCTCTAATTAATTAACGAGCAGATAG
TCTCGTTCTCGCCCTGCCTGATGACTAATTAATTAACCCGGATCCTTTTTATAGCTAATTAGTCACGTACCTTTGAG
AGTACCACTTCAGCTACCTCTTTTGTGTCTCAGAGTAACTTTCTTTAATCAATTCCAAAACAGTATATGATTTTCCA
TTTCTTTCAAAGATGTAGTTTACATCTGCTCCTTTGTTGAAAAGTAGCCTGAGCACTTCTTTTCTACCATGAATTAC
AGCTGGCAAGATCAATTTTTCCCAGTTCTGGACATTTTATTTTTTTAAGTAGTGTGCTACATATTTCAATATTTCC
AGATTGTACAGCGATCATTAAAGGAGTACGTCCCATGTTATCCAGCAAGTCAGTATCAGCACCTTTGTTCAATAGAA
GTTTAACCATTGTTAAATTTTTATTTGATACGGCTATATGTAGAGGAGTTAACCGATCCGTGTTTGAAATATCTACA
TCCGCCGAATGAGCCAATAGAAGTTTAACCAAATTAACTTTGTTAAGGTAAGCTGCCAAACACAAAGGAGTAAAGCC
TCCGCTGTAAAGAACATTGTTTACATAGTTATTCTTCAACAGATCTTTCACTATTTTGTAGTCGTCTCTCAACACCG
CATCATGCAGACAAGAAGTTGTGCATTCAGTAACTACAGGTTTAGCTCCATACCTCATCAAGATTTTTATAGCCTCG
GTATTCTTGAACATTACAGCCATTTCAAGAGGAGATTGTAGAGTACCATATTCCGTGTTAGGGTCGAATCCATTGTC
CAAAAACCTATTTAGAGATGCATTGTCATTATCCATGATAGCCTCACAGACGTATATGTAAGCCATCTTGAATGTAT
AATTTTGTTGTTTTCAACAACCGCTCGTGAACAGCTTCTATACTTTTTCATTTTCTTCATGATTAATATAGTTTACG
GAATATAAGTATACAAAAAGTTTATAGTAATCTCATAATATCTGAAACACATACATAAAACATGGAAGAATTACACG
ATGTCGTTGAGATAAATGGCTTTTTATTGTCATAGTTTACAAATTCGCAGTAATCTTCATCTTTTACGAATATTGCA
GAATCTGTTTTATCCAACCAGTGATTTTTGTATAATATAACTGGTATCCTATCTTCCGATAGAATGCTGTTATTTAA
CATTTTTGCACCTATTAAGTTACATCTGTCAAATCCATCTTTCCAACTGACTTTATGTAACGATGCGAAATAGCATT
TATCACTATGTCGTACCCAATTATCATGACAAGATTCTCTTAAATACGTAATCTTATTATCTCTTGCATATTCGTAA
TAGTAATTGTAAAGAGTATACGATAACAGTATAGATATACACGTGATATAAATATTTAACCCCATTCCTGAGTAAAA
TAATTACGATATTACATTTCCTTTTATTATTTTTATGTTTTAGTTATTTGTTAGGTTATACAAAAATTATGTTTATT
TGTGTATATTTAAAGCGTCGTTAAGAATAAGCTTAGTTAACATATTATCGCTTAGGTTTTGTAGTATTTGAATCCTT
TCTTTAAATGGATTATTTTTCCAATGCATATTTATAGCTTCATCCAAAGTATAACATTTAACATTCA (SEQ ID
NO:2)
```

FIGURE 3

|  |  | 1 | 50 |
|---|---|---|---|
| HA Newmarket | (1) | MKTTIILILLTHWVYSQNPTSGNNTATLCLGHHAVANGTLVKTITDDQIE | |
| HA Ohio | (1) | MKTTIILILLTHWAYSQNPISGNNTATLCLGHHAVANGTLVKTISDDQIE | |

|  |  | 51 | 100 |
|---|---|---|---|
| HA Newmarket | (51) | VTNATELVQSISIGKICNNSYRVLDGRNCTLIDAMLGDPHCDDFQYENWD | |
| HA Ohio | (51) | VTNATELVQSISMGKICNNSYRILDGRNCTLIDAMLGDPHCDAFQYENWD | |

|  |  | 101 | 150 |
|---|---|---|---|
| HA Newmarket | (101) | LFIERSSAFSNCYPYDIPDYASLRSIVASSGTLEFTAEGFTWTGVTQNGR | |
| HA Ohio | (101) | LFIERSSAFSNCYPYDIPDYASLRSIVASSGTLEFTAEGFTWTGVTQNGR | |

|  |  | 151 | 200 |
|---|---|---|---|
| HA Newmarket | (151) | SGACKRGSADSFFSRLNWLTKSGNSYPILNVTMPNNKNFDKLYIWGIHHP | |
| HA Ohio | (151) | SGACKRGSADSFFSRLNWLTKSGSSYPTLNVTMPNNKNFDKLYIWGIHHP | |

|  |  | 201 | 250 |
|---|---|---|---|
| HA Newmarket | (201) | SSNKEQTKLYIQESGRVTVSTERSQQTVIPNIGSRPWVRGQSGRISIYWT | |
| HA Ohio | (201) | SSNQEQTKLYIQESGRVTVSTKRSQQTIIPNIGSRPWVRGQSGRISIYWT | |

|  |  | 251 | 300 |
|---|---|---|---|
| HA Newmarket | (251) | IVKPGDILMINSNGNLVAPRGYFKLRTGKSSVMRSDALIDTCVSECITPN | |
| HA Ohio | (251) | IVKPGDILMINSNGNLVAPRGYFKLRTGKSSVMRSDVPIDICVSECITPN | |

|  |  | 301 | 350 |
|---|---|---|---|
| HA Newmarket | (301) | GSIPNDKPFQNVNKITYGKCPKYIRQNTLKLATGMRNVPEKQIRGIFGAI | |
| HA Ohio | (301) | GSISNDKPFQNVNKVTYGKCPKYIRQNTLKLATGMRNVPEKQIRGIFGAI | |

|  |  | 351 | 400 |
|---|---|---|---|
| HA Newmarket | (351) | AGFIENGWEGMVDGWYGFRYQNSEGTGQAADLKSTQAAIDQINGKLNRVI | |
| HA Ohio | (351) | AGFIENGWEGMVDGWYGFRYQNSEGTGQAADLKSTQAAIDQINGKLNRVI | |

|  |  | 401 | 450 |
|---|---|---|---|
| HA Newmarket | (401) | ERTNEKFHQIEKEFSEVEGRIQDLEKYVEDTKIDLWSYNAELLVALENQH | |
| HA Ohio | (401) | ERTNEKFHQIEKEFSEVEGRIQDLEKYVEDTKIDLWSYNAELLVALENQH | |

|  |  | 451 | 500 |
|---|---|---|---|
| HA Newmarket | (451) | TIDLTDAEMNKLFEKTRRQLRENAEDMGGGCFKIYHKCDNACIGSIRNGT | |
| HA Ohio | (451) | TIDLTDAEMNKLFEKTRRQLKENAEDMGGGCFKIYHKCDNACIGSIRNGT | |

|  |  | 501 | 550 |
|---|---|---|---|
| HA Newmarket | (501) | YDHYIYRDEALNNRFQIKSVELKSGYKDWILWISFAISCFLICVVLLGFI | |
| HA Ohio | (501) | YDHYIYRDEALNNRFQIKGVELKSGYKDWILWISFAISCFLICVVLLGFI | |

|  |  | 551 | 566 |
|---|---|---|---|
| HA Newmarket | (551) | MWACQKGNIRCNICI- (SEQ ID NO: 3) | |
| HA Ohio | (551) | MWACQKGNIRCNICI- (SEQ ID NO: 4) | |

FIGURE 4A

Isolate the synthetic EIV H3 HA from a plasmid, pEIV H3N8 HA by EcoRV/XhoI digestion, ligate to EcoRV/XhoI digested pALVAC C5 donor plasmid Remove the multiple cloning sites consisting of XhoI, Xba I, Cla I and Sma I between the HA ORF and the T5AT sequence by ligation of re-filled XhoI site with Sma I site

FIGURE 5A

```
  1    MKTTIILILL THWAYSQNPI SGNNTATLCL GHHAVANGTL VKTISDDQIE
 51    VTNATELVQS ISMGKICNNS YRILDGRNCT LIDAMLGDPH CDAFQYENWD
101    LFIERSSAFS NCYPYDIPDY ASLRSIVASS GTLEFTAEGF TWTGVTQNGR
151    SGACKRGSAD SFFSRLNWLT KSGSSYPTLN VTMPNNKNFD KLYIWGIHHP
201    SSNQEQTKLY IQESGRVTVS TKRSQQTIIP NIGSRPWVRG QSGRISIYWT
251    IVKPGDILMI NSNGNLVAPR GYFKLKTGKS SVMRSDVPID ICVSECITPN
301    GSISNDKPFQ NVNKVTYGKC PKYIRQNTLK LATGMRNVPE KQIRGIFGAI
351    AGFIENGWEG MVDGWYGFRY QNSEGTGQAA DLKSTQAAID QINGKLNRVI
401    ERTNEKFHQI EKEFSEVEGR IQDLEKYVED TKIDLWSYNA ELLVALENQH
451    TIDLTDAEMN KLFEKTRRQL KENAEDMGGG CFKIYHKCDN ACIGSIRNGT
501    YDHYIYRDEA LNNRFQIKGV ELKSGYKDWI LWISFAISCF LICVVLLGFI
551    MWACQKGNIR CNICI* (SEQ ID NO: 5)
```

FIGURE 5B

```
             M13R                                                         C5R
  1   GGAAACAGCT ATGACCATGA TTACGAATTG CGGCCGCAAT TCTGAATGTT
      CCTTTGTCGA TACTGGTACT AATGCTTAAC GCCGGCGTTA AGACTTACAA

51   AAATGTTATA CTTTGGATGA AGCTATAAAT ATGCATTGGA AAAATAATCC
      TTTACAATAT GAAACCTACT TCGATATTTA TACGTAACCT TTTTATTAGG

101   ATTTAAAGAA AGGATTCAAA TACTACAAAA CCTAAGCGAT AATATGTTAA
      TAAATTTCTT TCCTAAGTTT ATGATGTTTT GGATTCGCTA TTATACAATT

151   CTAAGCTTAT TCTTAACGAC GCTTTAAATA TACACAAATA AACATAATTT
      GATTCGAATA AGAATTGCTG CGAAATTTAT ATGTGTTTAT TTGTATTAAA

201   TTGTATAACC TAACAAATAA CTAAAACATA AAAATAATAA AAGGAAATGT
      AACATATTGG ATTGTTTATT GATTTTGTAT TTTTATTATT TTCCTTTACA

251   AATATCGTAA TTATTTTACT CAGGAATGGG GTTAAATATT TATATCACGT
      TTATAGCATT AATAAAATGA GTCCTTACCC CAATTTATAA ATATAGTGCA

301   GTATATCTAT ACTGTTATCG TATACTCTTT ACAATTACTA TTACGAATAT
      CATATAGATA TGACAATAGC ATATGAGAAA TGTTAATGAT AATGCTTATA
                                                 7927.DC
351   GCAAGAGATA ATAAGATTAC GTATTTAAGA GAATCTTGTC ATGATAATTG
      CGTTCTCTAT TATTCTAATG CATAAATTCT CTTAGAACAG TACTATTAAC
      7927.DC
401   GGTACGACAT AGTGATAAAT GCTATTTCGC ATCGTTACAT AAAGTCAGTT
      CCATGCTGTA TCACTATTTA CGATAAAGCG TAGCAATGTA TTTCAGTCAA

451   GGAAAGATGG ATTTGACAGA TGTAACTTAA TAGGTGCAAA AATGTTAAAT
      CCTTTCTACC TAAACTGTCT ACATTGAATT ATCCACGTTT TTACAATTTA
                             7696.CXL
501   AACAGCATTC TATCGGAAGA TAGGATACCA GTTATATTAT ACAAAAATCA
      TTGTCGTAAG ATAGCCTTCT ATCCTATGGT CAATATAATA TGTTTTTAGT

551   CTGGTTGGAT AAAACAGATT CTGCAATATT CGTAAAAGAT GAAGATTACT
      GACCAACCTA TTTTGTCTAA GACGTTATAA GCATTTTCTA CTTCTAATGA

601   GCGAATTTGT AAACTATGAC AATAAAAAGC CATTTATCTC AACGACATCG
      CGCTTAAACA TTTGATACTG TTATTTTTCG GTAAATAGAG TTGCTGTAGC

651   TGTAATTCTT CCATGTTTTA TGTATGTGTT TCAGATATTA TGAGATTACT
      ACATTAAGAA GGTACAAAAT ACATACACAA AGTCTATAAT ACTCTAATGA

701   ATAAACTTTT TGTATACTTA TATTCCGTAA ACTATATTAA TCATGAAGAA
      TATTTGAAAA ACATATGAAT ATAAGGCATT TGATATAATT AGTACTTCTT
```

Continuation of FIGURE 5B

```
 751   AATGAAAAAG TATAGAAGCT GTTCACGAGC GGTTGTTGAA AACAACAAAA
       TTACTTTTTC ATATCTTCGA CAAGTGCTCG CCAACAACTT TTGTTGTTTT
                            7926.DC
 801   TTATACATTC AAGATGGCTT ACATATACGT CTGTGAGGCT ATCATGGATA
       AATATGTAAG TTCTACCGAA TGTATATGCA GACACTCCGA TAGTACCTAT

851   ATGACAATGC ATCTCTAAAT AGGTTTTTGG ACAATGGATT CGACCCTAAC
       TACTGTTACG TAGAGATTTA TCCAAAAACC TGTTACCTAA GCTGGGATTG

901   ACGGAATATG GTACTCTACA ATCTCCTCTT GAAATGGCTG TAATGTTCAA
       TGCCTTATAC CATGAGATGT TAGAGGAGAA CTTTACCGAC ATTACAAGTT

951   GAATACCGAG GCTATAAAAA TCTTGATGAG GTATGGAGCT AAACCTGTAG
       CTTATGGCTC CGATATTTTT AGAACTACTC CATACCTCGA TTTGGACATC
                            7697.CXL
1001   TTACTGAATG CACAACTTCT TGTCTGCATG ATGCGGTGTT GAGAGACGAC
       AATGACTTAC GTGTTGAAGA ACAGACGTAC TACGCCACAA CTCTCTGCTG

1051   TACAAAATAG TGAAAGATCT GTTGAAGAAT AACTATGTAA ACAATGTTCT
       ATGTTTTATC ACTTTCTAGA CAACTTCTTA TTGATACATT TGTTACAAGA

1101   TTACAGCGGA GGCTTTACTC CTTTGTGTTT GGCAGCTTAC CTTAACAAAG
       AATGTCGCCT CCGAAATGAG GAAACACAAA CCGTCGAATG GAATTGTTTC

1151   TTAATTTGGT TAAACTTCTA TTGGCTCATT CGGCGGATGT AGATATTTCA
       AATTAAACCA ATTTGAAGAT AACCGAGTAA GCCGCCTACA TCTATAAAGT

1201   AACACGGATC GGTTAACTCC TCTACATATA GCCGTATCAA ATAAAAATTT
       TTGTGCCTAG CCAATTGAGG AGATGTATAT CGGCATAGTT TATTTTTAAA
                            7925.DC
1251   AACAATGGTT AAACTTCTAT TGAACAAAGG TGCTGATACT GACTTGCTGG
       TTGTTACCAA TTTGAAGATA ACTTGTTTCC ACGACTATGA CTGAACGACC

1301   ATAACATGGG ACGTACTCCT TTAATGATCG CTGTACAATC TGGAAATATT
       TATTGTACCC TGCATGAGGA AATTACTAGC GACATGTTAG ACCTTTATAA

1351   GAAATATGTA GCACACTACT TAAAAAAAAT AAAATGTCCA GAACTGGGAA
       CTTTATACAT CGTGTGATGA ATTTTTTTTA TTTTACAGGT CTTGACCCTT

1401   AAATTGATCT TGCCAGCTGT AATTCATGGT AGAAAGAAG TGCTCAGGCT
       TTTAACTAGA ACGGTCGACA TTAAGTACCA TCTTTTCTTC ACGAGTCCGA

1451   ACTTTTCAAC AAAGGAGCAG ATGTAAACTA CATCTTTGAA AGAAATGGAA
       TGAAAAGTTG TTTCCTCGTC TACATTTGAT GTAGAAACTT TCTTTACCTT
                                                    7792.SL
1501   AATCATATAC TGTTTTGGAA TTGATTAAAG AAAGTTACTC TGAGACACAA
       TTAGTATATG ACAAAACCTT AACTAATTTC TTTCAATGAG ACTCTGTGTT
           7792.SL
```

Continuation of FIGURE 5B

```
1551  AAGAGGTAGC TGAAGTGGTA CTCTCAAAGG TACGTGACTA ATTAGCTATA
      TTCTCCATCG ACTTCACCAT GAGAGTTTCC ATGCACTGAT TAATCGATAT

1601  AAAAGGATCC GGGTTAATTA ATTAGTCATC AGGCAGGGCG AGAACGAGAC
      TTTTCCTAGG CCCAATTAAT TAATCAGTAG TCCGTCCCGC TCTTGCTCTG
                                   H6
1651  TATCTGCTCG TTAATTAATT AGAGCTTCTT TATTCTATAC TTAAAAAGTG
      ATAGACGAGC AATTAATTAA TCTCGAAGAA ATAAGATATG AATTTTTCAC

1701  AAAATAAATA CAAAGGTTCT TGAGGGTTGT GTTAAATTGA AAGCGAGAAA
      TTTTATTTAT GTTTCCAAGA ACTCCCAACA CAATTTAACT TTCGCTCTTT
                                                  H3  HA  M ·
1751  TAATCATAAA TTATTTCATT ATCGCGATAT CCGTTAAGTT TGTATCGTAA
      ATTAGTATTT AATAAAGTAA TAGCGCTATA GGCAATTCAA ACATAGCATT
                 11670JY
       .. K  T  T    I  I  L    I  L  L  T    H  W  A  Y  S  Q
1801  TGAAAACCAC CATCATCCTG ATCCTGCTGA CCCACTGGGC CTACAGCCAG
      ACTTTTGGTG GTAGTAGGAC TAGGACGACT GGGTGACCCG GATGTCGGTC
                  11671JY
       N  P  I  S  G  N  N    T  A  T    L  C  L  G    H  H  A ·
1851  AACCCTATCA GCGGCAACAA CACCGCCACC CTGTGCCTGG GCCACCACGC
      TTGGGATAGT CGCCGTTGTT GTGGCGGTGG GACACGGACC CGGTGGTGCG

. V  A  N    G  T  L  V    K  T  I    S  D  D    Q  I  E  V ·
1901  CGTGGCCAAC GGCACCCTGG TCAAGACCAT CAGCGACGAC CAGATCGAAG
      GCACCGGTTG CCGTGGGACC AGTTCTGGTA GTCGCTGCTG GTCTAGCTTC

.. T  N  A    T  E  L    V  Q  S  I    S  M  G    K  I  C
1951  TGACCAACGC CACCGAGCTG GTGCAGAGCA TCAGCATGGG CAAGATCTGC
      ACTGGTTGCG GTGGCTCGAC CACGTCTCGT AGTCGTACCC GTTCTAGACG

N  N  S  Y    R  I  L    D  G  R    N  C  T    L    I  D  A ·
2001  AACAACAGCT ACCGCATCCT GGACGGCAGA AACTGCACCC TGATCGACGC
      TTGTTGTCGA TGGCGTAGGA CCTGCCGTCT TTGACGTGGG ACTAGCTGCG

. M  L  G    D  P  H  C    D  A  F    Q  Y  E    N  W  D  L ·
2051  CATGCTGGGC GACCCCCACT GCGACGCCTT CCAGTACGAG AACTGGGACC
      GTACGACCCG CTGGGGGTGA CGCTGCGGAA GGTCATGCTC TTGACCCTGG

.. F  I  E    R  S  S    A  F  S  N    C  Y  P    Y  D  I
2101  TGTTCATCGA GAGGAGCAGC GCCTTCAGCA ACTGCTACCC CTACGACATC
      ACAAGTAGCT CTCCTCGTCG CGGAAGTCGT TGACGATGGG GATGCTGTAG

P  D  Y  A    S  L  R    S  I  V    A  S  S  G    T  L  E ·
2151  CCTGACTACG CCAGCCTGAG AAGCATCGTG GCCAGCAGCG GCACCCTGGA
      GGACTGATGC GGTCGGACTC TTCGTAGCAC CGGTCGTCGC CGTGGGACCT
                 11672JY
       . F  T  A    E  G  F    T  W  T  G    V  T    Q  N  G  R  S ·
```

Continuation of FIGURE 5B

```
           GTTCACCGCC GAGGGCTTCA CCTGGACCGG CGTGACCCAG AACGGCAGAA
2201       CAAGTGGCGG CTCCCGAAGT GGACCTGGCC GCACTGGGTC TTGCCGTCTT
               11673JY
        .. G   A   C   K   R   G   S   A   D   S   F   F   S   R   L   N
2251       GCGGCGCCTG CAAGAGAGGC AGCGCCGACA GCTTCTTCAG CCGCCTGAAC
           CGCCGCGGAC GTTCTCTCCG TCGCGGCTGT CGAAGAAGTC GGCGGACTTG

W   L   T   K   S   G   S   S   Y   P   T   L   N   V   T   M   P  .
2301       TGGCTGACCA AGAGCGGCAG CAGCTACCCC ACCCTGAACG TGACCATGCC
           ACCGACTGGT TCTCGCCGTC GTCGATGGGG TGGGACTTGC ACTGGTACGG

.  N   N   K   N   F   D   K   L   Y   I   W   G   I   H   H   P   S  .
2351       CAACAACAAG AACTTCGACA AGCTGTACAT CTGGGGCATC CACCACCCCA
           GTTGTTGTTC TTGAAGCTGT TCGACATGTA GACCCCGTAG GTGGTGGGGT

.. S   N   Q   E   Q   T   K   L   Y   I   Q   E   S   G   R   V
2401       GCAGCAACCA GGAGCAGACC AAGCTGTACA TCCAGGAGAG CGGCAGAGTG
           CGTCGTTGGT CCTCGTCTGG TTCGACATGT AGGTCCTCTC GCCGTCTCAC

T   V   S   T   K   R   S   Q   Q   T   I   I   P   N   I   G   S  .
2451       ACCGTGTCCA CCAAGAGAAG CCAGCAGACC ATCATCCCCA ACATCGGCAG
           TGGCACAGGT GGTTCTCTTC GGTCGTCTGG TAGTAGGGGT TGTAGCCGTC

.  R   P   W   V   R   G   Q   S   G   R   I   S   I   Y   W   T   I  .
2501       CAGACCTTGG GTGCGCGGCC AGTCCGGCAG GATCAGCATC TACTGGACCA
           GTCTGGAACC CACGCGCCGG TCAGGCCGTC CTAGTCGTAG ATGACCTGGT

.. V   K   P   G   D   I   L   M   I   N   S   N   G   N   L   V
2551       TCGTGAAGCC TGGCGACATC CTGATGATCA ACAGCAACGG CAACCTGGTG
           AGCACTTCGG ACCGCTGTAG GACTACTAGT TGTCGTTGCC GTTGGACCAC
               11674JY
           A   P   R   G   Y   F   K   L   K   T   G   K   S   S   V   M   R  .
2601       GCCCCCAGAG GCTACTTCAA GCTGAAAACC GGCAAGAGCA GCGTGATGAG
           CGGGGGTCTC CGATGAAGTT CGACTTTTGG CCGTTCTCGT CGCACTACTC
               11675JY
        .  S   D   V   P   I   D   I   C   V   S   E   C   I   T   P   N   G  .
2651       AAGCGACGTG CCCATCGACA TCTGCGTGTC CGAGTGCATC ACCCCTAACG
           TTCGCTGCAC GGGTAGCTGT AGACGCACAG GCTCACGTAG TGGGGATTGC

.. S   I   S   N   D   K   P   F   Q   N   V   N   K   V   T   Y
2701       GCAGCATCAG CAACGACAAG CCCTTCCAGA ACGTGAACAA AGTGACCTAC
           CGTCGTAGTC GTTGCTGTTC GGGAAGGTCT TGCACTTGTT TCACTGGATG

G   K   C   P   K   Y   I   R   Q   N   T   L   K   L   A   T   G  .
2751       GGCAAGTGCC CCAAGTACAT CCGCCAGAAC ACCCTGAAGC TGGCCACCGG
           CCGTTCACGG GGTTCATGTA GGCGGTCTTG TGGGACTTCG ACCGGTGGCC

.  M   R   N   V   P   E   K   Q   I   R   G   I   F   G   A   I   A  .
```

Continuation of FIGURE 5B

```
2801  CATGAGAAAC GTGCCCGAGA AGCAGATCAG AGGCATCTTC GGCGCCATCG
      GTACTCTTTG CACGGGCTCT TCGTCTAGTC TCCGTAGAAG CCGCGGTAGC

. . G   F   I     E   N   G     W   E   G   M     V   D   G     W   Y   G
2851  CCGGCTTCAT CGAGAACGGC TGGGAGGGCA TGGTGGACGG CTGGTACGGC
      GGCCGAAGTA GCTCTTGCCG ACCCTCCCGT ACCACCTGCC GACCATGCCG

F   R   Y     Q   N   S     E   G   T   G     Q   A   A   D     L   K   S  ·
2901  TTCAGATACC AGAACAGCGA GGGCACCGGC CAGGCCGCCG ACCTGAAGAG
      AAGTCTATGG TCTTGTCGCT CCCGTGGCCG GTCCGGCGGC TGGACTTCTC

. T   Q   A     A   I   D   Q     I   N   G     K   L   N     R   V   I   E ·
2951  CACCCAGGCC GCCATCGACC AGATCAACGG CAAGCTGAAC CGCGTGATCG
      GTGGGTCCGG CGGTAGCTGG TCTAGTTGCC GTTCGACTTG GCGCACTAGC
              11676JY
        . . R   T   N     E   K   F     H   Q   I     E   K   E   F     S   E   V
3001  AGCGCACCAA CGAGAAGTTC CACCAGATCG AGAAGGAGTT CAGCGAAGTG
      TCGCGTGGTT GCTCTTCAAG GTGGTCTAGC TCTTCCTCAA GTCGCTTCAC
              11677JY
        E   G   R   I     Q   D   L     E   K   Y     V   E   D   T     K   I   D ·
3051  GAGGGCAGAA TCCAGGACCT GGAGAAGTAC GTGGAGGACA CCAAGATCGA
      CTCCCGTCTT AGGTCCTGGA CCTCTTCATG CACCTCCTGT GGTTCTAGCT

. L   W   S     Y   N   A   E     L   L   V     A   L   E     N   Q   H   T ·
3101  CCTGTGGAGC TACAACGCCG AGCTGCTGGT CGCCCTGGAG AACCAGCACA
      GGACACCTCG ATGTTGCGGC TCGACGACCA GCGGGACCTC TTGGTCGTGT

. . I   D   L     T   D   A     E   M   N   K     L   F   E     K   T   R
3151  CCATCGACCT GACCGACGCC GAGATGAACA AGCTGTTCGA AAAGACCAGG
      GGTAGCTGGA CTGGCTGCGG CTCTACTTGT TCGACAAGCT TTTCTGGTCC

R   Q   L   K     E   N   A     E   D   M     G   G   G     F   K   I ·
3201  CGCCAGCTGA AGGAAAACGC CGAGGACATG GGCGGCGGCT GCTTCAAGAT
      GCGGTCGACT TCCTTTTGCG GCTCCTGTAC CCGCCGCCGA CGAAGTTCTA

. Y   H   K     C   D   N   A     C   I   G     S   I   R     N   G   T   Y ·
3251  CTACCACAAG TGCGACAACG CCTGCATCGG CTCCATCAGG AACGGCACCT
      GATGGTGTTC ACGCTGTTGC GGACGTAGCC GAGGTAGTCC TTGCCGTGGA

. . D   H   Y     I   Y   R     D   E   A   L     N   N   R     F   Q   I
3301  ACGACCACTA CATCTACAGG GACGAGGCCC TGAACAACCG CTTCCAGATC
      TGCTGGTGAT GTAGATGTCC CTGCTCCGGG ACTTGTTGGC GAAGGTCTAG

K   G   V   E     L   K   S     G   Y   K     D   W   I   L     W   I   S ·
3351  AAGGGCGTGG AGCTGAAGAG CGGCTACAAG GACTGGATCC TGTGGATCAG
      TTCCCGCACC TCGACTTCTC GCCGATGTTC CTGACCTAGG ACACCTAGTC

. F   A   I     S   C   F   L     I   C   V     V   L   L     G   F   I   M ·
```

Continuation of FIGURE 5B

```
3401  CTTCGCCATC AGCTGCTTCC TGATCTGCGT GGTGCTGCTG GGCTTCATCA
      GAAGCGGTAG TCGACGAAGG ACTAGACGCA CCACGACGAC CCGAAGTAGT
                                 11678JY
      .. W   A    C    Q   K   G    N   I   R   C    N   I   C    I (SEQ ID NO: 5)
3451  TGTGGGCCTG CCAGAAGGGC AACATCCGCT GCAACATCTG CATCTGATGA
      ACACCCGGAC GGTCTTCCCG TTGTAGGCGA CGTTGTAGAC GTAGACTACT
                               11679JY      C5L
3501  CTCGAGGGTT TTTATGACTA GTTAATCACG GCCGCTTATA AAGATCTAAA
      GAGCTCCCAA AAATACTGAT CAATTAGTGC CGGCGAATAT TTCTAGATTT
                                                    7928.DC
3551  ATGCATAATT TCTAAATAAT GAAAAAAGT ACATCATGAG CAACGCGTTA
      TACGTATTAA AGATTTATTA CTTTTTTTCA TGTAGTACTC GTTGCGCAAT

3601  GTATATTTTA CAATGGAGAT TAACGCTCTA TACCGTTCTA TGTTTATTGA
      CATATAAAAT GTTACCTCTA ATTGCGAGAT ATGGCAAGAT ACAAATAACT
                                  7793.SL
3651  TTCAGATGAT GTTTTAGAAA AGAAAGTTAT TGAATATGAA AACTTTAATG
      AAGTCTACTA CAAAATCTTT TCTTTCAATA ACTTATACTT TTGAAATTAC

3701  AAGATGAAGA TGACGACGAT GATTATTGTT GTAAATCTGT TTTAGATGAA
      TTCTACTTCT ACTGCTGCTA CTAATAACAA CATTTAGACA AAATCTACTT

3751  GAAGATGACG CGCTAAAGTA TACTATGGTT ACAAAGTATA AGTCTATACT
      CTTCTACTGC GCGATTTCAT ATGATACCAA TGTTTCATAT TCAGATATGA

3801  ACTAATGGCG ACTTGTGCAA GAAGGTATAG TATAGTGAAA ATGTTGTTAG
      TGATTACCGC TGAACACGTT CTTCCATATC ATATCACTTT TACAACAATC

3851  ATTATGATTA TGAAAAACCA AATAAATCAG ATCCATATCT AAAGGTATCT
      TAATACTAAT ACTTTTTGGT TTATTTAGTC TAGGTATAGA TTTCCATAGA

3901  CCTTTGCACA TAATTTCATC TATTCCTAGT TTAGAATACC TGCAGCCAAG
      GGAAACGTGT ATTAAAGTAG ATAAGGATCA AATCTTATGG ACGTCGGTTC

3951  CTTGGCACTG GCCGTCGTTT TAC (SEQ ID NO: 6)
      GAACCGTGAC CGGCAGCAAA ATG (SEQ ID NO: 7)
                 M13F
```

CANINE INFLUENZA VACCINES

INCORPORATION BY REFERENCE

This application is a continuation-in-part application of U.S. patent application Ser. No. 11/211,983 filed Aug. 25, 2005.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention encompasses influenza vaccines, in particular canine influenza vaccines. The vaccine may be a recombinant poxvirus vaccine or an inactivated vaccine.

BACKGROUND OF THE INVENTION

Respiratory diseases resembling influenza has infected thousands of dogs in the U.S. Recurrent outbreaks of severe respiratory disease characterized by coughing and fever have occurred in greyhounds at racing kennels. Pathological findings included severe pulmonary and plural hemorrhage, accurate to subacute erosive to hyperplastic tracheitis, bronchitis and bronchiolitis and bronchopneumonia. In 2004, eight greyhounds in Jacksonville, Fla. were killed by an equine influenza virus that jumped the species barrier from horses to dogs.

Equine influenza is a disease of horses, and the virus is in the same group of viruses that cause flu in people. The disease is present in horse populations throughout Europe, North America and parts of Asia, with horses typically developing a fever and a dry hacking cough. In the early stages of the disease, horses are reluctant to eat or drink for several days, but usually recover in two to three weeks.

H3N8 subtypes of equine influenza were previously isolated from lungs of two dogs from Florida and one dog from Texas who had died from the infection. Genetic sequence analyses and phylogenetic comparisons determined that all three canine isolates were closely related and evolved from contemporary strains of equine influenza H3N8. Immunohistochemistry demonstrated influenza antigen in bronchial gland epithelial cells, bronchial and bronchiolar epithelial cells and in alveolar macrophages. Seroconversion to canine influenza virus was demonstrated by hemagglutination inhibition and microneutralization assays.

Molecular and antigenic analyses of three influenza viruses isolated from outbreaks of severe respiratory disease in racing greyhounds revealed that they are closely related to H3N8 equine influenza virus (see, e.g., Crawford et al., Science. 2005 Oct. 21;310(5747):482-5. Epub 2005 Sep. 26). Phylogenetic analysis indicated that the canine influenza virus genomes form a monophyletic group, consistent with a single interspecies virus transfer. Molecular changes in the hemagglutinin suggested adaptive evolution in the new host. The etiologic role of this virus in respiratory disease was supported by the temporal association of rising antibody titers with disease and by experimental inoculation studies. The geographic expansion of the infection and its persistence for several years indicate efficient transmission of canine influenza virus among greyhounds. Evidence of infection in pet dogs suggests that this infection may also become enzootic in this population.

In 2005, a mutated form of the Bird Flu (H3N8 Virus) was reported to have killed greyhounds in Massachusetts.

Accordingly, there is a need for an effective vaccine against influenza in canines.

Citation or identification of any document in this application is not an admission that such document is available as prior art to the present invention.

SUMMARY OF THE INVENTION

The present invention encompasses canine influenza vaccines, which may be a recombinant canine influenza vaccine or an inactivated canine influenza vaccine.

In an embodiment wherein the canine influenza vaccine is a recombinant vaccine, advantageously, the vector is an avipox expression vector which may comprise a polynucleotide encoding an influenza antigen, epitope or immunogen. The influenza antigen, epitope or immunogen may be a hemagglutinin, matrix protein, neuraminidase, nonstructural protein, nucleoprotein, polymerase or any fragment thereof.

In an advantageous embodiment, the canine influenza antigen, epitope or immunogen is derived from a canine infected with influenza. For example, but not by limitation, influenza virus may be isolated from the broncho alveolar lavage and/or lung tissues of an affected dog. Isolation and characterization of the nucleotide sequence of the influenza infecting the dog may be done by routine experimentation by a person of ordinary skill in the art.

The canine influenza antigen, epitope or immunogen may be isolated from an equine influenza. The equine influenza may be an Ohio equine influenza, Kentucky equine influenza or a Newmarket equine influenza.

The avipox expression vector may be an attenuated avipox expression vector. In one embodiment, the avipox expression vector may be a canarypox vector, advantageously ALVAC. The influenza antigen, epitope or immunogen may be a hemagglutinin, such as H3. The canarypox vector may be CP 2242, CP1529 or CP1533.

The present invention also encompasses an inactivated influenza vaccine. The inactivated influenza vaccine may be an inactivated canine influenza. In another embodiment, the inactivated influenza vaccine may be an equine influenza, advantageously an Ohio equine influenza, Kentucky equine influenza or a Newmarket equine influenza. The vaccine may be inactivated with formalin or beta-propiolactone.

The invention also relates to method of eliciting an immune response against influenza in a canine, which may comprise administering a formulation comprising any one of the above recombinant influenza vaccine or inactivated vaccine and a pharmaceutically or veterinarily acceptable carrier, excipient or vehicle in an effective amount for eliciting an immune response. In an advantageous embodiment, an adjuvant may be added. The adjuvant may be aluminum hydroxide, alumimum phosphate, a carbomer or an oil-water-emulsion and optionally may comprise CpG. Advantageously, the administration may be subcutaneous or intramuscular.

The invention further relates to method of inducing an immune response against influenza in a canine, which may comprise administering a formulation comprising any one of the above recombinant influenza vaccine or inactivated vaccine and a pharmaceutically or veterinarily acceptable carrier, excipient or vehicle in an effective amount for inducing an immune response. In an advantageous embodiment, an adjuvant may be added. The adjuvant may be aluminum hydroxide, alumimum phosphate, a carbomer or an oil-water-emulsion and optionally may comprise CpG. Advantageously, the administration may be subcutaneous or intramuscular.

The invention further encompasses a kit for performing a method of eliciting or inducing an immune response which may comprise any one of the recombinant influenza vaccines or inactivated vaccines and instructions for performing the method.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 illustrates the sequence of the insert in PJT004 (SEQ ID NO: 1);

FIG. 2 illustrates the sequence of the insert in PJT005 (SEQ ID NO: 2);

FIG. 3 illustrates a comparison of the amino acid sequence of EIV Ohio 03 strain HA to that of New Market strain H3 HA (SEQ ID NOS: 3 and 4);

FIG. 4A illustrates a construction of an ALVAC donor plasmid for generation of an ALVAC recombinant expressing codon optimized EIV H3 HA (Ohio 03);

FIG. 5A illustrates a predicted amino acid sequence of product(s): EIV H3 HA;

FIG. 5B illustrates a nucleotide sequence of arms and insert with translation

DETAILED DESCRIPTION

Figure 4B:
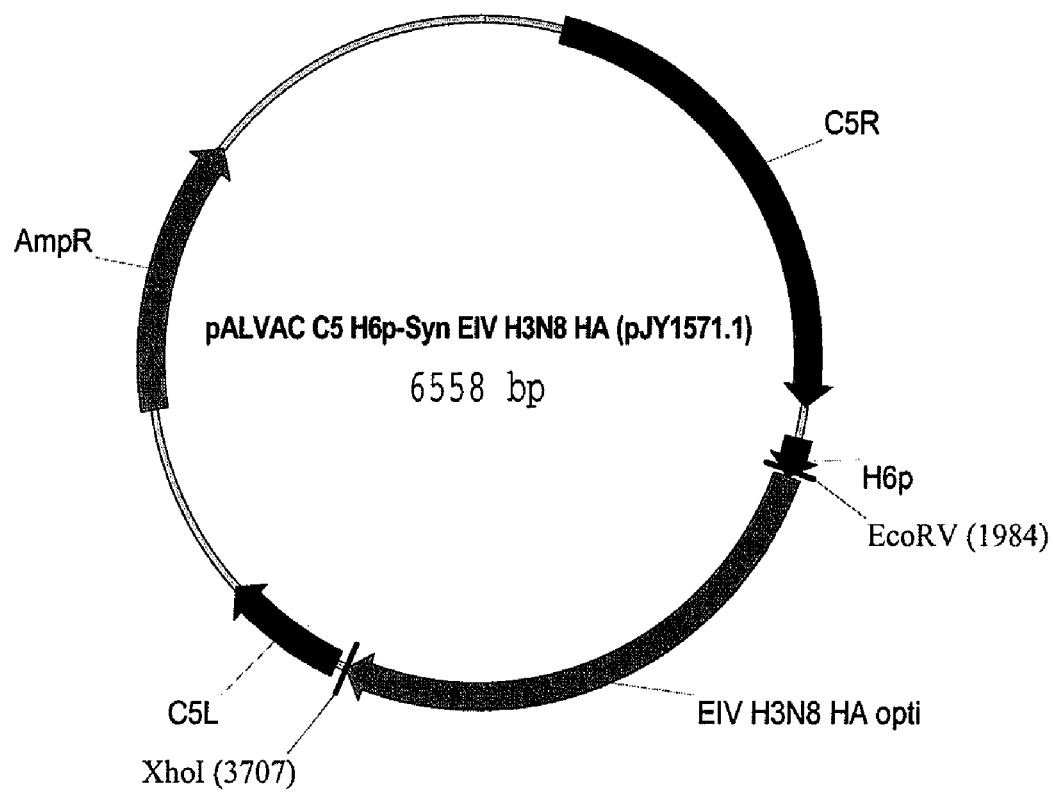
FIG. 4B illustrates pALVAC C5 H6p-synthetic EIV H3 HA, pJY1571.1.

The present invention is based, in part, on Applicants' studies demonstrating a recombinant canarypox expressing equine influenza HA is immunogenic in dogs.

The present invention encompasses any influenza antigen, epitope or immunogen that elicits an immunogenic response in an animal, advantageously a vertebrate, more advantageously a dog. The influenza antigen, epitope or immunogen may be any influenza antigen, epitope or immunogen, such as, but not limited to, a protein, peptide or fragment thereof, that elicits, induces or stimulates a response in an animal, advantageously a vertebrate, more advantageously a dog.

In an advantageous embodiment, the canine influenza antigen, epitope or immunogen is derived from a canine infected with influenza. For example, but not by limitation, influenza virus may be isolated from the broncho alveolar lavage and/or lung tissues of an affected dog. Isolation and characterization of the nucleotide sequence of the influenza infecting the dog may be done by routine experimentation by a person of ordinary skill in the art.

In another advantageous embodiment, the canine influenza, antigen, epitope or immunogen may be derived from an equine infected with influenza or an equine influenza strain. Advantageously, the equine influenza strain is an Ohio equine influenza, Kentucky equine influenza strain or a Newmarket equine influenza strain. The canine influenza antigen, epitope or immunogen may be determined by one of ordinary skill of the art from the nucleotide sequences of Examples 4 and 5. Advantageously, the canine influenza antigen, epitope or immunogen is a hemagglutinin (HA) (e.g., HA precursor, H1, H2, protein, matrix protein (e.g., matrix protein M1 or M2), neuraminidase, nonstructural (NS) protein (e.g., NS1 or NS2), nucleoprotein (NP) and polymerase (e.g., PA polymerase, PB1 polymerase 1 or PB2 polymerase 2).

Examples of Kentucky equine influenza strains that may be used in methods of the present invention include, but are not limited to, equine influenza strains A/eq/Kentucky/98 (see, e.g., Crouch et al., Vaccine. 2004 Dec. 2;23(3):418-25), A/Equi 2 (Kentucky 81) (see, e.g., Short et al., J Vet Pharmacol Ther. 1986 December;9(4):426-32, Homer & Ledgard, N Z Vet J. 1988 December;36(4):205-6), A/equine/Kentucky/1/81 (Eq/Ky) (see, e.g., Breathnach et al., Vet Immunol Immunopathol. 2004 April;98(3-4):127-36), A/Equine/Kentucky/1/81 (H3N8) (see, e.g., Olsen et al., Vaccine. 1997 July;15 (10): 1149-56, Morley et al. Vet Microbiol. 1995 June;45(1): 81-92, Ozaki et al., Vet Microbiol. 2001 Sep. 20;82(2):111-9, Sugiura et al., J Virol Methods. 2001 October;98(1):1-8, see, e.g., Sugiura et al., J Virol Methods. 2001 October;98(1): 1-8, Goto et al., J Vet Med Sci. 1993 February;55(1):33-7, Goto et al., J Vet Med Sci. 1993 February;55(1):33-7, A/Equine/Kentucky/1/91 (H3N8) (see, e.g., Youngner et al., Am J Vet Res. 2001 August;62(8):1290-4), A/Equine/Kentucky/1277/90 (Eq/Kentucky) (see, e.g., Webster & Thomas, Vaccine. 1993;11(10):987-93), A/Equine/Kentucky/2/91 (H3N8) (see, e.g., Donofrio et al., J Vet Diagn Invest. 1994 January; 6(1):39-43), A/Equine/Kentucky/79 (H3N8) (see, e.g., Donofrio et al., J Vet Diagn Invest. 1994 January;6(1):39-43), A/equine/Kentucky/81 (see, e.g., Sugiura et al., J Virol Methods. 2001 October;98(1):1-8), A/equine/Kentucky/91 (H3N8) (see, e.g., Gross et al., Equine Vet J. 1998 November; 30(6):489-97), A/equine-2/Kentucky/95 (H3N8) (see, e.g., Heldens et al., Vet J. 2004 March;167(2):150-7) and A/equine-2/Kentucky/98 (see, e.g., Chambers et al., Equine Vet J. 2001 November;33(7):630-6), the disclosures of which are incorporated by reference in their entireties.

Examples of Newmarket equine influenza strains that may be used in methods of the present invention include, but are not limited to, equine influenza strains A/eq/Newmarket/1/77 (see, e.g., Lindstrom et al., Arch Virol. 1998;143(8):1585-98), A/eq/Newmarket/5/03 (see, e.g., Edlund Toulemonde et al., Vet Rec. 2005 Mar. 19;156(12):367-71), A/Equi 2 (H3N8), Newmarket 1/93 (see, e.g., Mohler et al., Biotechnol Bioeng. 2005 Apr. 5;90(1):46-58, Nayak et al., J Chromatogr B Analyt Technol Biomed Life Sci. 2005 Jul. 8), A/equi-2/Newmarket-1/93 (see, e.g., Heldens et al., J Immunol Methods. 2002 Jun. 1;264(1-2):11-7), A/equine/Newmarket/2/93 (see, e.g., Wattrang et al., Viral Immunol. 2003;16(1):57-67), A/equine/Newmarket/79 (H3N8) (see, e.g., Duhaut & Dimmock, Virology. 2000 Sep. 30;275(2):278-85, Noble & Dimmock, J Gen Virol. 1994 December;75 (Pt 12):3485-91, Duhaut & Dimmock, Virology. 1998 Sep. 1;248(2):241-53, Hannant & Mumford, Vet Immunol Immunopathol. 1989 July;21(3-4):327-37, Hannant et al., Vet Microbiol. 1989 April;19(4):293-303, Hannant et al., Vet Rec. 1988 Feb. 6;122(6):125-8, Richards et al., Vet Immunol Immunopathol. 1992 June;33(1-2):129-43, Heldens et al., Vet J. 2004 March; 167(2):150-7), A/equine/Newmarket/1/77 (H7N7) (see, e.g., Goto et al., J Vet Med Sci. 1993 February;55(1):33-7, Sugiura et al., J Virol Methods. 2001 October;98(1):1-8, Sugiura et al., J Virol Methods. 2001 October;98(1):1-8) and A/equine-2/Newmarket-2/93 (see, e.g., Heldens et al., Vet J. 2004 March; 167(2):150-7), the disclosures of which are incorporated by reference in their entireties.

The present invention also encompasses other equine influenza viruses, such as, but not limited to, equine influenza virus A/eq/Miami/63 (H3N8) (see, e.g., van Maanen et al., Vet Microbiol. 2003 Jun. 10;93(4):291-306), A/equi 1 (Prague strain) (see, e.g., Homer & Ledgard, N Z Vet J. 1988 December;36(4):205-6, Short et al., J Vet Pharmacol Ther. 1986 December;9(4):426-32), A/Equi 2 (Miami) (see, e.g., Short et al., J Vet Pharmacol Ther. 1986 December;9(4):426-32), A/equi-1/Prague/56 (Pr/56) (see, e.g., Heldens et al., J Immunol Methods. 2002 Jun. 1;264(1-2):11-7), A/equi-2/Suffolk/89 (Suf/89) (see, e.g., Heldens et al., J Immunol Methods. 2002 Jun. 1;264(1-2):11-7), A/Equine 2/Sussex/89 (H3N8) (see, e.g., Mumford et al., Vet Rec. 1994 Feb. 12;134(7):158-62), A/equine/Sussex/89 (see, e.g., Wattrang et al., Viral Immunol. 2003;16(1):57-67), A/equine-2/Saskatoon/90 (see, e.g., Chambers et al., Equine Vet J. 2001 November;33(7):630-6), A/Equine/Prague/1/56 (H7N7) (see, e.g., Donofrio et al., J Vet Diagn Invest. 1994 January;6(1):39-43, Morley et al. Vet Microbiol. 1995 June;45(1):81-92), A/equine/Miami/1/63 (H3N8) (see, e.g., Morley et al. Vet Microbiol. 1995 June; 45(1):81-92, Ozaki et al., Vet Microbiol. 2001 Sep. 20;82(2):111-9, Thomson et al., Vet Rec. 1977 May 28;100(22):465-8, Mumford et al., Epidemiol Infect. 1988 June;100(3):501-10, Donofrio et al., J Vet Diagn Invest. 1994 January;6(1):39-43, Mumford et al., J Hyg (Lond). 1983 June;90(3):385-95), A/Aichi/2/68 (H3N2) (see, e.g., Ozaki et al., Vet Microbiol. 2001 Sep. 20;82(2):111-9), A/equine/Tokyo/2/71 (H3N8) (see, e.g., Goto et al., J Vet Med Sci. 1993 February;55(1):33-7), A/eq/LaPlata/1/88 (see, e.g., Lindstrom et al., Arch Virol. 1998;143(8):1585-98), A/Equine/Jilin/1/89 (Eq/Jilin) (see, e.g., Webster & Thomas, Vaccine. 1993;11(10):987-93), A/Equine/Alaska/1/91 (H3N8) (see, e.g., Webster & Thomas, Vaccine. 1993;11(10):987-93), A/equine/Saskatoon/1/91 (H3N8) (see, e.g., Morley et al. Vet Microbiol. 1995 June;45 (1):81-92), A/equine/Rome/5/91 (H3N8) (see, e.g., Sugiura et al., J Virol Methods. 2001 October;98(1):1-8), A/equine/La Plata/1/93 (H3N8) (see, e.g. Ozaki et al., Vet Microbiol. 2001 Sep. 20;82(2):111-9), A/equine/La Plata/1/93 (LP/93) (see, e.g., Sugiura et al., J Virol Methods. 2001 October;98(1):1-8), A/eq/Holland/1/95 (H3N8) (see, e.g., van Maanen et al., Vet Microbiol. 2003 Jun. 10;93(4):291-306) and A/eq/Holland/2/95 (H3N8) (see, e.g., van Maanen et al., Vet Microbiol. 2003 Jun. 10;93(4):291-306), the disclosures of which are incorporated by reference in their entireties.

In another advantageous embodiment, the canine influenza, antigen, epitope or immunogen may be derived from an equine infected with influenza or an equine influenza strain derived from a recent isolate.

The influenza antigen, epitope or immunogen may also be isolated from any influenza strain such as, but not limited to, avian H5N1 influenza virus, A/Hong Kong/156/97 (A/HK/156/97) (see, e.g., Leneva et al., Antimicrob Agents Chemother. 2001 April;45(4):1216-24), avian H7N1 influenza strain (see, e.g., Foni et al., New Microbiol. 2005 January;28(1):31-5), avian H9N2 influenza virus (see, e.g., Leneva et al., Antimicrob Agents Chemother. 2001 April;45 (4):1216-24), avian influenza virus A/Chicken/HK/G9/97 (H9N2) (see, e.g., Leneva et al., Antimicrob Agents Chemother. 2001 April;45(4):1216-24), avian influenza virus A/Quail/HK/G1/97 (H9N2) (see, e.g., Leneva et al., Antimicrob Agents Chemother. 2001 April;45(4):1216-24), avian influenza virus A/Teal/HK/W312/97 (H6N1) (see, e.g., Leneva et al., Antimicrob Agents Chemother. 2001 April;45 (4):1216-24), avian pandemic influenza A viruses of avian origin (see, e.g., Audsley & Tannock, Expert Opin Biol Ther. 2004 May;4(5):709-17), cold-adapted (ca) and temperature sensitive (ts) master donor strain, A/Leningrad/134/17/57 (H2N2) (see, e.g., Youil et al., Virus Res. 2004 Jun. 15; 102 (2):165-76), equine influenza virus (A/Equi 2 (H3N8), Newmarket 1/93) (see, e.g., Mohler et al., Biotechnol Bioeng. 2005 Apr. 5;90(1):46-58; Nayak et al., J Chromatogr B Analyt Technol Biomed Life Sci. 2005 Jul. 8), equine-2 influenza virus (EIV; subtype H3N8) (see, e.g., Virology. 2001 Aug. 15;287(1):202-13), equine-2 influenza virus, A/Equine/Kentucky/1/91 (H3N8) (see, e.g., Youngner et al., Am J Vet Res. 2001 August;62(8):1290-4), human influenza virus A(H3N2) isolates (see, e.g., Abed et al., J Infect Dis. 2002 Oct. 15;186 (8):1074-80), human influenza virus A/Memphis/1/71 (H3N2) (see, e.g., Suzuki et al., Biochem J. 1996 Sep. 1;318 (Pt 2):389-93), human influenza virus A/Nanchang/933/95 (H3N2) virus (see, e.g., Scholtissek et al., J Virol. 2002 February;76(4):1781-6), human influenza virus A/PR/8/34 (H1N1) virus (see, e.g., Scholtissek et al., J Virol. 2002 February;76(4):1781-6), human influenza virus A/Singapore/57 (H2N2) virus (see, e.g., Scholtissek et al., J Virol. 2002 February;76(4):1781-6), influenza virus A (see, e.g., Chare et al., J Gen Virol. 2003 October;84(Pt 10):2691-703), influenza virus A PR/8/34 (PR8) virus (H1N1 subtype) (see, e.g., Mantani et al., Planta Med. 2001 April;67(3):240-3), influenza virus A/Aichi/2/68(H3N2) (see, e.g., Miyamoto et al., Antiviral Res. 1998 August;39(2):89-100), influenza virus A/Ann Arbor/6/60 cold-adapted virus (see, e.g., Treanor et al., J Virol. 1994 December;68(12):7684-8), influenza virus A/Beijing 32/92 (H3N2) (see, e.g., Zakay-Rones et al., J Altern Complement Med. 1995 Winter;1(4):361-9), influenza virus A/Charlottesville/31/95 (H1N1) (see, e.g., Gubareva et al., J Gen Virol. 2002 November;83(Pt 11):2683-92), influenza virus A/Kawasaki/86 (H1N1) virus (see, e.g., Staschke et al., Virology. 1998 Sep. 1;248(2):264-74), influenza virus A/Korea/82 (H3N2) (see, e.g., Treanor et al., J Virol. 1994 December;68(12):7684-8), influenza virus A/Leningrad/134/57 (see, e.g., Egorov et al., J Virol. 1998 August;72(8):6437-41), influenza virus A/NWS/33 (H1N1) (see, e.g., Sidwell et al., Antiviral Res. 1998 February;37(2):107-20), influenza virus A/PR/8/34(H1N1) (see, e.g., Miyamoto et al., Antiviral Res. 1998 August;39(2):89-100), influenza virus A/PR8/34 (see, e.g., Nunes-Correia et al., Biochemistry. 1999 Jan. 19;38(3):1095-101, Tree et al., Vaccine. 2001 May 14;19(25-26):3444-50), influenza virus A/Puerto Rico (PR)/8/34 (see, e.g., Egorov et al., J Virol. 1998 August;72(8):6437-41), influenza virus A/Puerto Rico/8-Mount Sinai (see, e.g., Mazanec et al., J Virol. 1995 February;69(2):1339-43), influenza virus A/Shangdong 9/93 (H3N2) (see, e.g., Zakay-Rones et al., J Altern Complement Med. 1995 Winter;1(4):361-9, Sidwell et al., Antiviral Res. 1998 February;37(2): 107-20), influenza virus A/Shingapol/1/57(H2N2) (see, e.g., Miyamoto et al., Antiviral Res. 1998 August;39(2):89-100), influenza virus A/Singapore 6/86

(H1N1) (see, e.g., Zakay-Rones et al., J Altern Complement Med. 1995 Winter;1(4):361-9), influenza virus A/Singapore/1/57 (H2N2) (see, e.g., Bantia et al., Antimicrob Agents Chemother. 1998 April;42(4):801-7), influenza virus A/Texas 36/91 (HINI) (see, e.g., Zakay-Rones et al., J Altern Complement Med. 1995 Winter;1(4):361-9), influenza virus A/Texas/36/91 (H1N1) virus (see, e.g., Gubareva et al., J Infect Dis. 2001 Feb. 15;183(4):523-31, Halperin et al., Vaccine. 1998 August;16(13):1331-5), influenza virus A/Texas/36/91(H1N1) (see, e.g., Hayden et al., Antiviral Res. 1994 October;25(2):123-31), influenza virus A/Udorn/72 virus infection (see, e.g., Shimizu et al., Virology. 1999 Feb. 15;254(2):213-9), influenza virus A/Victoria/3/75 (H3N2) (see, e.g., Sidwell et al., Antiviral Res. 1998 February;37(2):107-20), influenza virus A/Virginia/88(H3N2) (see, e.g., Hayden et al., Antiviral Res. 1994 Oct;25(2):123-31), influenza virus A/WSN/33 (H1N1) (see, e.g., Lu et al., Arch Virol. 2002;147(2):273-84), influenza virus A/WSN/33 (see, e.g., Gujuluva et al., Virology. 1994 Nov. 1;204(2):491-505), influenza virus B (see, e.g., Chare et al., J Gen Virol. 2003 October;84(Pt 10):2691-703), influenza virus B/Ann Arbor 1/86 (see, e.g., Zakay-Rones et al., J Altern Complement Med. 1995 Winter;1(4):361-9), influenza virus B/Harbin/7/94 (see, e.g., Halperin et al., Vaccine. 1998 August; 16(13):1331-5, influenza virus B/Hong Kong/5/72 (see, e.g., Sidwell et al., Antiviral Res. 1998 February;37(2):107-20), influenza virus B/Lee/40 (see, e.g., Miyamoto et al., Antiviral Res. 1998 August;39(2):89-100), influenza virus B/Victoria group (see, e.g., Nakagawa et al., J Virol Methods. 1999 April;79(1):113-20), influenza virus B/Yamagata 16/88 (see, e.g., Zakay-Rones et al., J Altern Complement Med. 1995 Winter;1(4):361-9), influenza virus B/Yamagata group (see, e.g., Nakagawa et al., J Virol Methods. 1999 April;79(1): 113-20), influenza virus B/Yamanashi/166/98 (see, e.g., Hoffinann et al., Proc Natl Acad Sci U S A. 2002 Aug. 20;99(17):11411-6), influenza virus C (see, e.g., Chare et al., J Gen Virol. 2003 October;84(Pt 10):2691-703), influenza virus strain A/Equi/2/Kildare/89 (see, e.g., Quinlivan et al., J Clin Microbiol. 2004 February;42(2):759-63), influenza virus type B/Panama 45/90 (see, e.g., Zakay-Rones et al., J Altern Complement Med. 1995 Winter;1(4):361-9), live, cold-adapted, temperature-sensitive (ca/ts) Russian influenza A vaccines (see, e.g., Palker et al., Virus Res. 2004 October;105(2):183-94), Madin Darby Canine Kidney (MDCK)-derived cell line (see, e.g., Halperin et al., Vaccine. 2002 Jan. 15;20(7-8):1240-7), mouse-adapted influenza virus A/Guizhou/54/89 (H3N2 subtype) (see, e.g., Nagai et al., Biol Pharm Bull. 1995 February;18(2):295-9), mouse-adapted influenza virus A/PR/8/34 (A/PR8) (see, e.g., Nagai et al., Antiviral Res. 1995 January;26(1):11-25), mouse-adapted influenza virus B/Ibaraki/2/85 (see, e.g., Nagai et al., Biol Pharm Bull. 1995 February;18(2):295-9), Russian live attenuated influenza vaccine donor strains A/Leningrad/134/17/57, A/Leningrad/134/47/57 and B/USSR/60/69 (see, e.g., Audsley & Tannock, J Virol Methods. 2005 February;123(2):187-93), swine H1 and H3 influenza viruses (see, e.g., Gambaryan et al., Virus Res. 2005 Jul. 1), swine influenza A viruses (see, e.g., Landolt et al., Am J Vet Res. 2005 January;66(1):119-24), swine influenza virus (SIV) (see, e.g., Clavijo et al., Can J Vet Res. 2002 April;66(2):117-21), swine influenza virus A/Sw/Ger 2/81 (see, e.g., Zakay-Rones et al., J Altern Complement Med. 1995 Winter;1(4):361-9), swine influenza virus A/Sw/Ger 8533/91 (see, e.g., Zakay-Rones et al., J Altern Complement Med. 1995 Winter;1(4):361-9), turkey influenza virus A/Tur/Ger 3/91 (see, e.g., Zakay-Rones et al., J Altern Complement Med. 1995 Winter;1(4):361-9) and turkey influenza virus A/turkey/Minnesota/833/80 (H4N2) (see, e.g., Gubareva et al., J Virol. 1997 May;71(5):3385-90), the disclosures of which are incorporated by reference.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also refers includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in the PCT Application Ser. No. PCT/US2004/022605 incorporated herein by reference in its entirety.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996) J. Immunol. 157:3242-3249; Suhrbier, A. (1997) Immunol. and Cell Biol. 75:402-408; Gardner et al. (1998) 12th World AIDS Conference, Geneva, Switzerland, Jun. 28-Jul. 3, 1998. Immunogenic fragments, for purposes of the present invention, will usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of an influenza protein or polyprotein. A polynucleotide encoding a fragment of the total protein or polyprotein, more advantageously, comprises or consists essentially of or consists of a minimum of 21 nucleotides, advantageously at least 42 nucleotides, and preferably at least 57, 87 or 150 consecutive or contiguous nucleotides of the sequence encoding the total protein or polyprotein. Epitope determination procedures, such as, generating overlapping peptide libraries (Hemmer B. et al., Immunology Today, 1998, 19 (4), 163-168), Pepscan (Geysen et al., (1984) Proc. Nat. Acad. Sci. USA, 81, 3998-4002; Geysen et al., (1985) Proc. Nat. Acad. Sci. USA, 82, 178-182; Van der Zee R. et al., (1989) Eur. J. Immunol., 19, 43-47; Geysen H. M., (1990) Southeast Asian J. Trop. Med. Public Health, 21, 523-533; Multipin.RTM. Peptide Synthesis Kits de Chiron) and algorithms (De Groot A. et al., (1999) Nature Biotechnology, 17, 533-561), and in PCT Application Ser. No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The invention further comprises a complementary strand to a polynucleotide encoding an influenza antigen, epitope or immunogen. The complementary strand can be polymeric and of any length, and can contain deoxyribonucleotides, ribonucleotides, and analogs in any combination.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

Hybridization reactions can be performed under conditions of different "stringency." Conditions that increase stringency of a hybridization reaction are well known. See for example, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of the influenza polypeptides and functionally equivalent fragments thereof which may enhance, decrease or not significantly affect properties of the polypeptides encoded thereby. These functionally equivalent variants, derivatives, and fragments display the ability to retain influenza activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the influenza polynucleotide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993;90: 5873-5877.

Another example of a mathematical algorithm used for comparison of sequences is the algorithm of Myers & Miller, CABIOS 1988;4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses the influenza polynucleotides contained in a vector molecule or an expression vector and operably linked to a promoter element and optionally to an enhancer.

The vector is advantageously a poxvirus, particularly a vaccinia virus or an avipox virus, such as fowlpox virus and canarypox virus. Advantageously, the virus is a canarypox virus. Advantageous canarypox strains may be an attenuated strain. The vector can express at least one epitope from Kentucky strains, Newmarket strains and/or Ohio strains. Advantageous canarypox constructs include, but are not limited to, vCP 1529, vCP 1533 and vCP 2242. Recombinant avipox viruses (see, e.g., U.S. Pat. Nos. 5,505,941 and 5,756,103), such as an attenuated recombinant canarypox virus, for instance ALVAC, or an attenuated fowlpox virus, for instance TROVAC, are especially advantageous. In one advantageous embodiment, the recombinant ALVAC vaccine described by Edlund Toulemonde et al., Vet Rec. 2005 Mar. 19;156(12): 367-71 may be used as a canine influenza vaccine. Other viruses that may be used in methods of the invention include, but are not limited to, vaccinia viruses, such as an attenuated vaccinia virus, for instance NYVAC, adenoviruses, such as canine adenoviruses (CAV), and herpesviruses, such as canine herpesvirus (CHV) or a feline herpesvirus (FHV).

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector needs not be capable of replication in the ultimate target cell or subject. The term includes cloning vectors also included are viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an influenza antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. an influenza peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745, 051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16,1986; WO 90/01543; W091/11525; WO 94/16716; WO 96/39491; WO 98/33510; EP 265785; EP 0 370 573; Andreansky et al., Proc. Natl. Acad. Sci. USA 1996;93:11313-11318; Ballay et al., EMBO J. 1993;4:3861-65; Felgner et al., J. Biol. Chem. 1994;269:2550-2561; Frolov et al., Proc. Natl. Acad. Sci. USA 1996;93:11371-11377; Graham, Tibtech 1990;8:85-87; Grunhaus et al., Sem. Virol. 1992;3:237-52; Ju et al., Diabetologia 1998;41:736-739; Kitson et al., J. Virol. 1991;65: 3068-3075; McClements et al., Proc. Natl. Acad. Sci. USA 1996;93:11414-11420; Moss, Proc. Natl. Acad. Sci. USA 1996;93:11341-11348; Paoletti, Proc. Natl. Acad. Sci. USA 1996;93:11349-11353; Pennock et al., Mol. Cell. Biol. 1984; 4:399-406; Richardson (Ed), Methods in Molecular Biology 1995;39, "Baculovirus Expression Protocols," Humana Press Inc.; Smith et al. (1983) Mol. Cell. Biol. 1983;3:2156-2165; Robertson et al., Proc. Natl. Acad. Sci. USA 1996;93:11334-11340; Robinson et al., Sem. Immunol. 1997;9:271; and Roizman, Proc. Natl. Acad. Sci. USA 1996;93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., human adenovirus, canine adenovirus), herpesvirus (e.g. canine herpesvirus), baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-influenza peptides or fragments thereof to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of influenza antigens, epitopes or immunogens. Advantageously, the vector contains and expresses a polynucleotide that includes, consists essentially of, or consists of a polynucleotide coding for (and advantageously expressing) an influenza antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an influenza antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of an influenza antigen, epitope or immunogen, the vector or vectors expressing the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a-suitable host cell, polynucleotides from different canine influenza isolates encoding the same proteins and/or for different proteins, but advantageously the same proteins. Preparations containing one or more vectors containing, consisting essentially of or consisting of polynucleotides encoding, and advantageously expressing, advantageously in vivo, an influenza antigen, fusion protein or an epitope thereof. The invention is also directed at mixtures of vectors that contain, consist essentially of, or consist of coding for, and express, different influenza antigens, epitopes or immunogens, e.g., an influenza antigen, epitope or immunogen from different species such as, but not limited to, humans, pigs, in addition to avian species including chicken, ducks and geese.

According to one embodiment of the invention, the expression vector is a viral vector, in particular an in vivo expression vector. In an advantageous embodiment, the expression vector is an adenovirus vector. Advantageously, the adenovirus is a human Ad5 vector, an E1-deleted and/or an E3-deleted adenovirus.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. No. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mentionis made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter 13L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

In a particular embodiment the viral vector is an adenovirus, such as a human adenovirus (HAV) or a canine adenovirus (CAV).

In one embodiment the viral vector is a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus is propagated in E1-expressing 293 (F. Graham et al J. Gen. Virol. 1977, 36, 59-72) or PER cells, in particular PER.C6 (F. Falloux et al Human Gene Therapy 1998, 9, 1909-1917). The human adenovirus can be deleted in the E3 region, in particular from about nucleotide 28592 to about nucleotide 30470. The deletion in the E1 region can be done in combination with a deletion in the E3 region (see, e.g. J. Shriver et al. Nature, 2002, 415, 331-335, F. Graham et al Methods in Molecular Biology Vol. 7: Gene Transfer and Expression Protocols Edited by E. Murray, The Human Press Inc, 1991, p. 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from Promega Corp. The CMV-IE promoter is advantageously of murine or human origin. The promoter of the elongation factor 1α can also be used. A muscle specific promoter can also be used (X. Li et al Nat. Biotechnol. 1999, 17, 241-245). Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the b-globin gene, the intron isolated from the immunoglobulin gene, a splicing sequence from the SV40 early gene or the chimeric intron sequence isolated from the pCI vector from Promege Corp. comprising the human β-globin gene donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and /or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid-M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an influenza antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Advantageous host cells include, but are not limited to, baby hamster kidney (BHK) cells, colon carcinoma (Caco-2) cells, COS7 cells, MCF-7 cells, MCF-10A cells, Madin-Darby canine kidney (MDCK) lines, mink lung (Mv1Lu) cells, MRC-5 cells, U937 cells and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of an influenza antigen, epitope or immunogen in a target cell. Determination of the therapeutically effective amount is routine experimentation for one of ordinary skill in the art. In one embodiment, the formulation comprises an expression vector comprising a polynucleotide that expresses an influenza antigen, epitope or immunogen and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

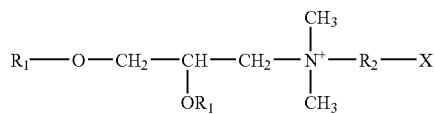

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95: about 5 to about 5: about 95, more advantageously about 1: about 1, e.g., 1:1.

The DMRIE or DMRIE-DOPE adjuvant:plasmid weight ratio can be between about 50: about 1 and about 1: about 10, such as about 10: about 1 and about 1: about 5, and advantageously about 1: about 1 and about 1: about 2, e.g., 1:1 and 1:2.

The invention also provides for inactivated canine influenza vaccines. As used herein, the term "inactivated vaccine" means a vaccine composition containing an infectious organism or pathogen that is no longer capable of replication or growth. Inactivation may be accomplished by a variety of methods sufficient to prevent replication or growth of the organism while maintaining its immunogenicity.

The inactivated vaccine may be an inactivated form of an isolate of an influenza virus from an affected dog. The virus may be isolated from the alveoli or lung of an affected dog. In another embodiment, the inactivated vaccine may be an inactivated equine influenza. In an advantageous embodiment, the equine influenza is a Kentucky or Newmarket equine influenza. The inactivated vaccine may be an inactivated version of any one of the influenza strains described above.

An inactivated vaccine may be prepared as well from the harvested culture fluid. The virus may be produced either by inoculation of 10-11-day embryonated eggs (J. Violay et al U.S. Pat. No. 6,048,537) or by inoculation of BHK-21 cell culture (C. Ross et al Archiv. Für die gesamte Virusforschung 1970, 30, 82-88; T. Tolstova et al Acta Virol. 1966, 10, 315-321; Ho. Merten et al Adv. Exp. Med. Biol. 1996, 397, 141-

151), of MDCK cell culture (J. Tree et al Vaccine 2001, 19, 3444-3450; Y. Ghendon et al Vaccine 2005, 23, 4678-4684; R. Brands et al Dev. Biol. Stand. 1999, 98, 93-100; R. Youil et al J Virol. Methods 2004, 120, 23-31), of Vero cell culture (O. Kistner et al Vaccine 1998, 16, 960-968; E. Govorkova et al J. Virol. 1996, 70, 5519-5524). The allantoic fluid or the cell culture supernatant can be clarified by low centrifugation and/or filtration. The virus can be concentrated by ultrafiltration and can be purified by zonal centrifugation on sucrose gradient (J. Violay et al U.S. Pat. No. 6,048,537; O. Kistner et al idem), by gel filtration (D. Nayak et al J. Chromatogr. B Analyt. Technol. Biomed. Life Sci. 2005, 823, 75-81; S. Tomita et al Kitasato Arch. Exp. Med. 1971, 44, 185-196).

Inactivation may be achieved by treating the viruses by any of the methods commonly employed to make inactivated vaccines. These methods include but are not limited to formaldehyde treatment (O. Kistner et al idem; A. Garcia et al Avian Diseases 1998, 42, 248-256), betapropriolactone treatment (B. Bdowsky et al Vaccine 1991, 9, 398-402 and Vaccine 1993, 11, 343-348; N. Keverin et al Arch. Virol. 2000, 145, 1059-1066), ethylene-imine treatment (D. Swayne et al Avian Diseases 2001, 45, 355-365), treatment with organic solvents, treatment with detergents, treatment with Tween-ether or treatment with Triton X-100 (J. Vilay et al idem) for allantoic fluid. For the inactivation the concentration can be about 0.01-0.2% w/v for the formaldehyde; about 0.03-0.2% w/v for the betapropiolactone; about 0.5-20 mM for ethylene-imine. The methods recited herein serve as art-known examples for inactivating virus. Inactivated virus vaccines are usually administered mixed with an adjuvant. The inactivated vaccine can be administered to the animal by any of a plurality of methods which include but are not limited to inoculation intramuscularly or subcutaneously, spraying, ocularly, nasally, orally, or in ovo.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778-780, Jun. 4, 1960.

With regard to structure, the acrylic or methacrylic acid polymers and EMA are preferably formed by basic units having the following formula:

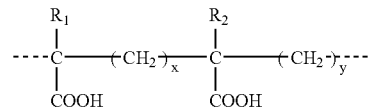

in which:
$R_1$ and $R_2$, which can be the same or different, represent H or $CH_3$
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon a (IFN α), interferon β (IFN β), interferon γ, (IFN γ), interleukin-1α (IL-1α), interleukin-1β

(IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β (TNF β), and transforming growth factor β (TGF β). It is understood that cytokines can be co-administered and/or sequentially administered with the immunogenic or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to dogs).

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of therapeutic and/or pharmaceutical compositions based on a plasmid vector, a dose can comprise, consist essentially of or consist of, in general terms, about in 1 µg to about 2000 µg, advantageously about 50 µg to about 1000 µg and more advantageously from about 100 µg to about 800 µg of plasmid expressing the influenza antigen, epitope or immunogen. When the therapeutic and/or pharmaceutical compositions based on a plasmid vector is administered with electroporation the dose of plasmid is generally between about 0.1 µg and 1 mg, advantageously between about 1 µg and 100 µg, advantageously between about 2 µg and 50 µg. The dose volumes can be between about 0.1 and about 2 ml, advantageously between about 0.2 and about 1 ml. These doses and dose volumes are suitable for the treatment of canines and other mammalian target species such as equines and felines.

The therapeutic and/or pharmaceutical composition contains per dose from about $10^4$ to about $10^{11}$, advantageously from about $10^5$ to about $10^{10}$ and more advantageously from about $10^6$ to about $10^9$ viral particles of recombinant adenovirus expressing an influenza antigen, epitope or immunogen. In the case of therapeutic and/or pharmaceutical compositions based on a poxvirus, a dose can be between about $10^2$ pfu and about $10^9$ pfu. The pharmaceutical composition contains per dose from about $10^5$ to $10^9$, advantageously from about $10^6$ to $10^8$ pfu of poxvirus or herpesvirus recombinant expressing the influenza antigen, epitope or immunogen.

The dose volume of compositions for target species that are mammals, e.g., the dose volume of canine compositions, based on viral vectors, e.g., non-poxvirus-viral-vector-based compositions, is generally between about 0.1 to about 2.0 ml, preferably between about 0.1 to about 1.0 ml, and more preferably between about 0.5 ml to about 1.0 ml.

With inactivated compositions of the virus or organism or pathogen produced on the new cell culture, the animal may be administered approximately $10^4$-$10^9$ equivalent $CCID_{50}$ (titer before inactivation), advantageously approximately $10^5$-$10^8$ equivalent $CCID_{50}$ in a single dosage unit. The volume of one single dosage unit can be between 0.2 ml and 5.0 ml and advantageously between 0.5 ml and 2.0 ml and more advantageously about 2.0 ml. One or more administrations can be done; e.g. with two injections at 2-4 weeks interval, and advantageously with a boost about 3 weeks after the first injection.

In an advantageous embodiment, an animal, advantageously a dog, is vaccinated with two doses of inactivated vaccine at about 3 to 4 week intervals via the subcutaneous route, although an intramuscular route is also contemplated. Blood samples may be collected on the day of the first and/or second vaccination and about 2 to 4 weeks after the second vaccination to determine the levels of anti-influenza virus specific antibodies by methods known to one of skill in the art, for example, virus neutralization, hemagglutination inhibition, ELISA or single radial heamolysis (SRH) tests.

The efficacy of the inactivated vaccines may be tested about 2 to 4 weeks after the second immunization by challenging animals, advantageously dogs, with a virulent strain of influenza, advantageously the influenza H3N8 strain. The animal may be challenged by spray, intra-nasally, intra-tracheally and/or orally. The challenge viral may be about $10^{5-8}$ EID50 in a volume depending upon the route of administration. For example, if the administration is by spray, a virus suspension is aerosolized to generate about 1 to 100 µm droplets, if the administration is intra-nasal, intra-tracheal or oral, the volume of the challenge virus is about 0.5 ml, 1-2 ml and 5-10 ml, respectively. Animals may be observed daily for 14 days following challenge for clinical signs, for example, fever, cough, nasal, ocular discharge, respiratory distress, anorexia and lethargy. In addition, groups of animals may be euthanized and evaluated for pathological findings of pulmonary and pleural hemorrhage, tracheitis, bronchitis, bronchiolitis, and bronchopneumonia. Tracheal swabs may be collected from all animals post challenge days 1-14 for virus isolation. The presence or absence of viral antigens in respiratory tissues may be evaluated by immunohistochemistry, for example, on days 3, 7 and 10 post-challenge. Blood samples may be collected post-challenge (e.g., on days 7 and 14 post-challenge) and may be analyzed for the presence of anti-influenza H3N8 virus specific antibody.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Biojector or Vitajet apparatus (Bioject, Oreg., USA)). Another approach to administer plasmid compositions is to use electroporation (see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158). In another embodiment, the therapeutic composition is delivered to the animal by gene gun or gold particle bombardment. In an advantageous embodiment, the animal is a vertebrate. In a more advantageous embodiment, the vertebrate is a dog.

One embodiment of the invention is a method of eliciting an immune response against influenza in an animal, comprising administering a formulation for delivery and expression of a recombinant poxvirus influenza vaccine or inactivated influenza vaccine in an effective amount for eliciting an immune response. Still another embodiment of the invention is a method of inducing an immunological or protective response against influenza in an animal, comprising administering to the animal an effective amount of a formulation for delivery and expression of an influenza antigen, epitope or immunogen wherein the formulation comprises recombinant poxvirus influenza vaccine or inactivated influenza vaccine and a pharmaceutically or veterinarily acceptable carrier, vehicle or excipient.

The invention relates to a method to elicit, induce or stimulate the immune response of an animal, advantageously a vertebrate. In one embodiment, the vertebrate is a dog but may also be a cat.

Another embodiment of the invention is a kit for performing a method of inducing an immunological or protective response against influenza in an animal comprising a recombinant influenza poxvirus vaccine or an inactivated influenza vaccine and instructions for performing the method of delivery in an effective amount for eliciting an immune response in the animal.

The invention will now be further described by way of the following non-limiting examples.

EXAMPLE 1

Vaccination Of Dogs With Canarypox Expressing H3 Genes

A study was conducted in which dogs were vaccinated dogs on days 0 and 21 with a canarypox expressing H3 genes from Kentucky (CP1529) and Newmarket (CP1533) equine influenza. The construction of CP1529 and CP1533 is described in Examples 1 (c5 locus), 4 and 5 of International Patent Publication WO99/44633, the disclosure of which is incorporated by reference. The nucleotide sequence of the donor plasmids pJT004 and pJT005 are presented in FIGS. 1 and 2.

Sera was collected and tested against H3N8 influenza viruses and the other viruses. As shown in Table 1, canarypox expressing hemagglutinin H3 genes induced a substantial amount of antibodies which specifically reacted with H3N8 strains but not with H1N1 or H7N7. Importantly antibodies were detectable within two weeks after the first immunization.

Accordingly, a canarypox expressing an influenza HA gene is immunogenic in dogs.

TABLE 1

Vaccination of dogs with canarypox expressing H3 hemaglutinin genes

| Antigen | Bleed | VACCINATED GROUP | | | | | CONTROL GROUP | | | | |
|---|---|---|---|---|---|---|---|---|---|---|---|
| N/1/93 (H3N8) | D0 | 0 | 0 | 0 | 0 | 0 | 0 | 0 | 0 | 0 | 0 |
|  | D14 | 0 | 63.8 | 69.9 | 31.4 | 96.7 | n.s. | n.s. | n.s. | n.s. | n.s. |
|  | D21 | 104.1 | 91.4 | 121.5 | 74.6 | 121.5 | n.s. | n.s. | n.s. | n.s. | n.s. |
|  | D36 | 106 | 96.7 | 111.7 | 69.9 | 123.6 | n.s. | n.s. | n.s. | n.s. | n.s. |
|  | D51 | 76.2 | 55.1 | 74.6 | 38.3 | 69.9 | n.s. | n.s. | n.s. | n.s. | n.s. |
| N/2/93 (H3N8) | D0 | 0 | 0 | 0 | 0 | 0 | 0 | 0 | 0 | 0 | 0 |
|  | D14 | 0 | 25.1 | 59.4 | 29.2 | 60.8 | n.s. | n.s. | n.s. | n.s. | n.s. |
|  | D21 | 86.2 | 71.4 | 102.2 | 65.3 | 406 | n.s. | n.s. | n.s. | n.s. | n.s. |
|  | D36 | 82.8 | 74.6 | 96.7 | 62.3 | 100.4 | n.s. | n.s. | n.s. | n.s. | n.s. |
|  | D51 | 52.3 | 37.1 | 66.8 | 26.1 | 57.9 | n.s. | n.s. | n.s. | n.s. | n.s. |
| Pr/56 (H7N7) | D0 | 0 | 0 | 0 | 0 | 0 | 0 | 0 | 0 | 0 | 0 |
|  | D14 | 0 | 19.3 | 0 | 24.1 | 0 | n.s. | n.s. | n.s. | n.s. | n.s. |
|  | D21 | 0 | 0 | 0 | 0 | 0 | n.s. | n.s. | n.s. | n.s. | n.s. |
|  | D36 | 0 | 0 | 0 | 0 | 0 | n.s. | n.s. | n.s. | n.s. | n.s. |
|  | D51 | 0 | 0 | 0 | 0 | 0 | n.s. | n.s. | n.s. | n.s. | n.s. |
| PR8 (H1N1) | D0 | 0 | 0 | 0 | 0 | 0 | 0 | 0 | 0 | 0 | 0 |
|  | D14 | 0 | 16.7 | 0 | 19.3 | 0 | n.s. | n.s. | n.s. | n.s. | n.s. |
|  | D21 | 0 | 0 | 0 | 0 | 0 | n.s. | n.s. | n.s. | n.s. | n.s. |
|  | D36 | 0 | 0 | 0 | 0 | 0 | n.s. | n.s. | n.s. | n.s. | n.s. |
|  | D51 | 0 | 0 | 0 | 0 | 0 | 0 | 0 | 0 | 0 | 0 | n.s. = no sample

EXAMPLE 2

Contruction of the Donor Plasmid pALVAC CS H6p-Synthetic EIV H3 HA, pJY1571.1)

The HA gene was derived from equine influenza virus (EIV) H3N8 Ohio 03 strain isolated from a horse in 2003. The HA gene was synthetic with codon optimization for expression in mammlian cells. The amino acid sequence of EIV Ohio 03 strain HA was compared to that of New Market strain H3 HA and is presented in FIG. 3.

The purpose was the construction of an ALVAC donor plasmid for generation of an ALVAC recombinant expressing codon optimized EIV H3 HA (Ohio 03). The plasmid name was pALVAC C5 H6p-synthetic EIV H3 HA, pJY1571.1. The plasmid backbone is pALVAC C5 H6p. The promoter was a H6 promoter.

The description of plasmid construction was as follows and presented schematically in FIG. 4A. The synthetic EIV H3 HA (Ohio 03) was isolated from a plasmid pEIV H3N8 HA by EcoRV/Xhol digestion, and ligated to EcoRV/Xhol digested donor plasmid pALVAC C5 H6p to create pALVAC C5 H6p-Synthetic EIV H3 HA. In the resulting plasmid, there are multiple cloning sites consisting of Xhol, Xba I, Cla I and Sma I between the HA ORF and the T5AT sequence which serves as the transcription termination signal. To bring the HA ORF and the T5AT sequence close together, those cloning sites were then subsequently removed by ligation of re-filled Xhol site with Sma 1 site. The resulting plasmid pJY1571.1 was then sequenced and confirmed to contain the correct sequence. A diagram of the resulting plasmid is presented in FIG. 4B. The predicted amino acid sequence of EIV H3 HA is shown in FIG. 5A and the nucleotide sequence of arms and insert with translation is shown in FIG. 5B.

EXAMPLE 3

Construction of the Recombinant Canarypox vCP2242

The purpose of this example was the generation and characterization of ALVAC recombinant containing EIV H3N8 codon optimized HA inserted at C5 loci of ALVAC (vCP2242). The parental virus was ALVAC, the donor plasmid was pJY1571.1, the insertion site was a C5 Locus, the promoter was a H6 promoter and cells for in vitro recombination were primary chicken embryo fibroblast cells (1° CEF).

The in vitro recombination (IVR) was performed by transfection of 1° CEF cells with 15 µg of Not I-linearized donor plasmid pJY1571.1. The transfected cells were subsequently infected with ALVAC as rescue virus at MOI of 10. After 24 hr, the transfected-infected cells were harvested, sonicated and used for recombinant virus screening.

Recombinant plaques were screened based on the plaque lift hybridization method using a 821 bp EIV syn HA specific probe labeled with horse radish peroxidase (HRP) according to the manufacturer's protocol. After four sequential rounds of plaque purification, the recombinant designated as vCP2242 was generated and confirmed by hybridization as 100% positive for the EIV syn HA insert and 100% negative for the C5 ORF.

Figure 6:
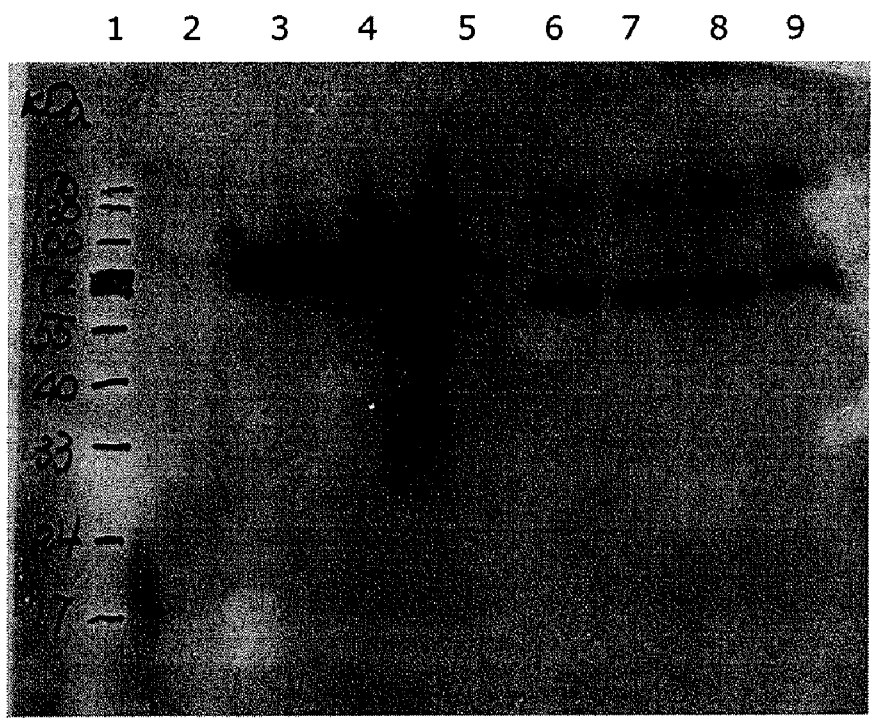
FIG. 6 illustrates a vCP2242 Western blot analysis. A 1/1,000 dilution of pooled anti-EIV antibody was used for the analysis. Lane 1: 5 µl Fermentas Prestain protein marker, lane 2: 15 µl ALVAC cell pellet, lane 3: 15 µl vCP2242. cell pellet, lane 4: 15 µl vCP2242. cell pellet, lane 5: 15 µl vCP1533 cell pellet, lane 6: space, lane 7: 40 µl ALVAC supernatant, lane 8: 40 µl vCP2242. supernatant, lane 9: 40 µl vCP2242. supernatant and lane 10: 40 µl vCP1533 supernatant.

Expression analysis and sequence analysis were performed. Expression analysis was performed by Western blot. Primary CEF cells were infected with vCP2242 stock at MOI of 10 and incubated at 37 C. for 26.5 hrs. The cells and culture supernatant were then harvested. Sample proteins were separated on a 10% SDS-PAGE gel, transferred to Immobilon nylon membrane, and probed with a pool of monoclonal mouse anti-EIV HA antibodies (anti Eq/AK/91: 124-1D9-1, 124-3E3-3, 124-4F3-2 and H3N8 A Eq/miami/63 pool at 1/1,000 dilution). Peroxidase-conjugated goat anti-mouse antiserum was used as a secondary antibody and the bands were visualized using luminol reagents. vCP2242 showed a protein expression profile with a 80 kDa protein expressed in cell pellet, but not in the culture medium as presented in FIG. 6.

Results of the sequence analysis demonstrated that the sequences of the EIV syn HA and C5L and C5R of ALVAC were correct.

EXAMPLE 4

Kentucky Equine Influenza Nucleotide Sequences

DEFINITION Influenza A virus (A/equine/Kentucky/5/02 (H3N8)) nonstructural protein gene, complete cds.

```
ACCESSION AY855345; SEQ ID NO: 8
  1 agcaaaagca gggtgacaaa aacataatgg attccaacac tgtgtcaagc tttcaggtag 61 actgttttct ttggcatgtc cgcaaacgat tcgcagacca agaactgggt gatgccccat 121 tccttgaccg gcttcgccga gaccagaagt ccctaagggg aagaggtatc actcttggtc 181 tggacatcga aacagccact catgcaggaa agcagatagt ggagcagatt ctggaaaagg 241 aatcagatga ggcacttaaa atgaccattg cctctgttcc tacttcacgc tacttaactg 301 acatgactct tgatgagatg tcaagagact ggttcatgct catgcccaag caaaaagtaa 361 caggctccct atgtataaga atggaccagg caatcatgga taagaacatc atacttaaag 421 caaactttag tgtgattttc gaaaggctgg aaacactaat actacttaga gccttcaccg 481 aagaaggagc agtcgttggc gaaatttcac cattaccttc tcttccagga catactaatg 541 aggatgtcaa aaatgcaatt ggggtcctca tcggaggact taaatggaat gataatacgg 601 ttagaatctc tgaaactcta cagagattcg cttggagaag cagtcatgag aatgggagac 661 cttcattccc ttcaaagcag aaatgaaaaa tggagagaac aattaagcca gaaatttgaa 721 gaaataagat ggttgattga agaagtgcga catagattga aaaatacaga aaatagtttt 781 gaacaaataa catttatgca agccttacaa ctattgcttg aagtagaaca agagataaga 841 actttctcgt ttcagcttat ttaatgataa aaaacaccct tgtttctact
```

DEFINITION Influenza A virus (A/equine/Kentucky/5/02 (H3N8)) matrix protein gene, complete cds.

```
ACCESSION AY855344; SEQ ID NO: 9
   1 agcaaaagca ggtagatatt taaagatgag tcttctgacc gaggtcgaaa cgtacgttct
  61 ctctatcgta ccatcaggcc ccctcaaagc cgagatcgcg cagagacttg aagatgtctt
 121 tgcagggaag aacaccgatc ttgaggcact catggaatgg ctaaagacaa gaccaatcct
 181 gtcacctttg actaaaggga ttttaggatt tgtattcacg ctcaccgtgc ccagtgagcg
 241 aggactgcag cgtagacgct ttgtccaaaa tgcccttagt ggaaacggag atccaaacaa
 301 catggacaga gcagtaaaac tgtacaggaa gcttaaaaga gaaataacat ccatggggc
 361 aaaagaggtg gcactaagct attccactgg tgcactagcc agctgcatgg gactcatata
 421 caacagaatg gaactgtga caaccgaagt ggcatttggc ctggtatgcg ccacatgtga
 481 acagattgct gattcccagc atcgatctca caggcagatg gtgacaacaa ccaacccatt
 541 aatcagacat gaaaacagaa tggtattagc cagtaccacg gctaaagcca tggaacagat
 601 ggcaggatca agtgagcagg cagcagaggc catggaggtt gctagtaagg ctaggcagat
 661 ggtacaggca atgagaacca ttgggaccca ccctagctcc agtgccggtt tgaaagatga
 721 tctccttgaa aatttacagg cctaccagaa acggatggga gtgcaaatgc agcgattcaa
 781 gtgatcctct cgttattgca gcaagtatca ttgggatctt gcacttgata ttgtggattc
 841 ttgatcgtct tttcttcaaa ttcatttatc gtcgccttaa atacgggttg aaaagagggc
 901 cttctacgga aggagtacct gagtctatga gggaagaata tcggcaggaa cagcagaatg
 961 ctgtggatgt tgacgatggt cattttgtca acatagagct ggagtaaaaa actaccttgt
1021 ttctact
```

DEFINITION Influenza A virus (A/equine/Kentucky/5/02 (H3N8)) neuraminidase gene, complete cds.

```
ACCESSION AY855343; SEQ ID NO: 10
   1 agcaaaagca ggagtttaaa atgaatccaa atcaaaagat aatagcaatt ggatttgcat
  61 cattggggat attaatcatt aacgtcattc tccatgtagt cagcattata gtaacagtac
 121 tggtcctcaa taacaatgga acaggtctga actgcaaagg gacgatcata agagagtaca
 181 atgaaacagt aagagtagaa aaaattactc aatggtataa taccagtgca attaagtaca
 241 tagagagacc tccaaatgaa tactacatga acaacaccga accactttgt gaggcccaag
 301 gctttgcacc attttccaaa gataatggaa tacgaattgg gtcgagaggc catgtttttg
 361 tgataagaga accttttgta tcatgttcgc cctcagaatg tagaacctt ttcctcacac
 421 agggctcatt actcaatgac aaacattcta acggcacagt aaaggaccga agtccatata
 481 ggactttgat gagtgtcaaa atagggcaat cacctaatgt gtatcaagct aggtttgaat
 541 cggtggcatg gtcagcaaca gcatgccatg atggaaaaaa atggatgaca gttggagtca
 601 cagggcccga caatcaagca attgcagtag tgaactatgg aggtgttccg gttgatatta
 661 ttaattcatg ggcaggggat atcttaagaa cccaagaatc atcatgcacc tgcattaaag
 721 gagactgtta ttgggtaatg actgatggac cggcaaatag gcaagctaaa tataggatat
 781 tcaaagcaaa agatggaaga gtaattggac agactgatat aagtttcaat ggggacacac
 841 tagaggagtg ttcttgttac cccaatgaag gaaggtgga atgcatatgc agggacaatt
 901 ggactggaac aaatagacca attctggtaa tatcttctga tctatcgtac acagttggat
```

-continued

```
 961 atttgtgtgc tggcattccc actgacactc ctaggggaga ggatagtcaa ttcacaggct 1021 catgtacaag acctttggga aataaaggat acggtgtaaa aggtttcggg tttcgacaag 1081 gaactgacgt atgggccgga aggacaatta gtaggacttc aagatcagga ttcgaaataa 1141 taaaaatcag gaatggttgg acacagaaca gtaaagacca aatcaggagg caagtgatta 1201 tcgatgaccc aaattggtca ggatatagcg gttctttcac attgccggtt gaactaacaa 1261 aaaagggatg tttggtcccc tgtttctggg ttgaaatgat tagaggtaaa cctgaagaaa 1321 caacaatatg gacctctagc agctccattg tgatgtgtgg agtagatcat aaaattgcca 1381 gttggtcatg gcacgatgga gctattcttc cctttgacat cgataagatg taatttacga 1441 aaaaactcct tgtttctact
```

DEFINITION Influenza A virus (A/equine/Kentucky/5/02
(H3N8)) nucleoprotein gene, complete cds.

```
ACCESSION AY855342; SEQ ID NO: 11
   1 agcaaaagca gggtagataa tcactcactg agtgacatca aagtcatggc gtctcaaggc 61 accaaacgat cctatgaaca gatggaaact gatgggaac gccagaatgc aactgaaatc 121 agagcatctg tcggaaggat ggtgggagga atcggccggt tttatgttca gatgtgtact 181 gagcttaaac taaacgacca tgaagggcgg ctgattcaga acagcataac aatagaaagg 241 atggtacttt cggcattcga cgaaagaaga aacaagtatc tcgaggagca tcccagtgct 301 ggaaaagacc ctaagaaaac gggaggcccg atatacagaa ggaaagatgg gaaatggatg 361 agggaactca tcctccatga taagaagaa atcatgagaa tctggcgtca ggccaacaat 421 ggtgaagacg ctactgctgg tcttactcat atgatgatct ggcactccaa tctcaatgac 481 accacatacc aaagaacaag ggctcttgtt cggactggga tggatcccag aatgtgctct 541 ctgatgcaag gctcaaccct cccacggaga tctggagccg ctggtgctgc agtaaaaggt 601 gttggaacaa tggtaatgga actcatcaga atgatcaaac gcggaataaa tgatcggaat 661 ttctggagag gtgaaaatgg tcgaaggacc agaattgctt atgaaagaat gtgcaatatc 721 ctcaaaggga aatttcagac agcagcacaa cgggctatga tggaccaggt gagggaaggc 781 cgcaatcctg gaaacgctga gattgaggat ctcattttct tagcacgatc agcacttatt 841 ttgagaggat cagtagccca taaatcatgc ctacctgcct gtgtttatgg ccttgcagta 901 accagtgggt atgactttga gaaggaagga tactctctgg ttggaattga tccttcaaa 961 ctactccaga acagtcaaat tttcagtcta atcagaccaa agaaaaccc agcacacaag 1021 agccagttgg tgtggatggc atgccattct gcagcatttg aggacctgag agttttgaat 1081 ttcattagag gaaccaaagt aatcccaaga ggacagttaa caaccagagg agttcaaatt 1141 gcttcaaatg aaaacatgga gacaatagat tctagcacac ttgaactgag aagcaaatat 1201 tgggcaataa ggaccagaag tggaggaaac accagtcaac agagagcatc tgcaggacag 1261 ataagtgtgc aacctacttt ctcagtacag agaaatcttc cctttgagag agcaaccatt 1321 atggctgcat tcactggtaa cactgaaggg aggacttccg acatgagaac ggaaatcata 1381 aggatgatgg aaagtgccaa atcagaagat gtgtctttcc aggggcgggg agtcttcgag 1441 ctctcggacg aaaaggcaac gaacccgatc gtgccttcct ttgacatgag caatgaaggg 1501 tcttatttct tcggagacaa tgctgaggaa tttgacagtt aaagaaaaat acccttgttt 1561 ctact
```

DEFINITION Influenza A virus (A/equine/Kentucky/5/02 (H3N8)) hemagglutinin precursor, gene, complete cds.

```
ACCESSION AY855341; SEQ ID NO: 12
   1 agcaaaagca ggggatattt ctgtcaatca tgaagacaac cattattttg atactactga
  61 cccattgggc ctacagtcaa aacccaatca gtggcaacaa cacagccaca ttgtgtctgg
 121 gacaccatgc agtagcaaat ggaacattgg taaaaacaat aagtgatgat caaattgagg
 181 tgacaaatgc tacagaatta gttcagagca tttcaatggg gaaaatatgc aacaactcat
 241 atagaattct agatggaaga aattgcacat taatagatgc aatgctagga gaccccact
 301 gtgacgtctt tcagtatgag aattgggacc tctttataga aagaagcagc gctttcagca
 361 attgctaccc atatgacatc cctgactatg catcgctccg atccattgta gcatcctcag
 421 gaacattgga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 agctatacat ctgggggatt catcacccga gctcaaatca gagcagaca aaattgtaca
 661 tccaagaatc aggacgagta acagtctcaa caaaagaag tcaacaaaca ataatcccta
 721 acatcggatc tagaccgtgg gtcagaggtc aatcaggcag ataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatctc caacgacaag ccattccaaa
 961 atgtgaacaa agttacatat ggaaaatgcc ccaagtatat caggcaaaac actttaaagt
1021 tggccactgg gatgaggaat gtaccagaaa agcaaatcag aggaatcttt ggagcaatag
1081 cgggattcat cgaaaacggc tgggaaggaa tggttgatgg gtggtatggg ttccgatatc
1141 aaaactctga aggaacaggg caagctgcag atctaaagag cactcaagca gccatcgacc
1201 agattaatgg aaagttaaac agagtgattg aaagaaccaa tgagaaattc catcaaatag
1261 agaaggaatt ctcagaagta aaggaagaa ttcaggactt ggagaaatat gtagaagaca
1321 ccaaaataga cctatggtcc tacaatgcag aattgctggt ggctctagaa aatcaacata
1381 caattgactt aacagatgca gaaatgaata aattattcga gaagactaga cgccagttaa
1441 gagaaaacgc agaagacatg ggaggtggat gtttcaagat ttaccacaaa tgtgataatg
1501 catgcattgg atcaataaga aatgggacat atgaccatta catatacaga gatgaagcat
1561 taaacaaccg atttcaaatc aaaggtgttg agttgaaatc aggctacaaa gattggatac
1621 tgtggatttc attcgccata tcatgcttct taatttgcgt tgttctattg ggtttcatta
1681 tgtgggcttg ccaaaaaggc aacatcagat gcaacatttg catttgagta aactgatagt
1741 taaaaacacc cttgtttcta ct
```

DEFINITION Influenza A virus (A/equine/Kentucky/5/02 (H3N8)) PA polymerase gene, complete cds.

```
ACCESSION AY855340; SEQ ID NO: 13
   1 agcgaaagca ggtactgatc caaaatggaa gactttgtgc gacagtgctt caatccaatg
  61 atcgtcgagc ttgcggaaaa ggcaatgaaa gaatatggag aggacccgaa aatcgaaaca
 121 aacaaatttg cagcaatatg cactcacttg gaagtctgct tcatgtactc ggatttccac
 181 tttattaatg aactgggtga gtcagtggtc atagagtctg tgacccaaa tgctcttttg
```

```
 241 aaacacagat tgaaatcat tgaggggaga gatcgaacaa tggcatggac agtggtaaac
 301 agcatctgca acaccacaag agctgaaaaa cctaaatttc ttccagattt atacgactat
 361 aaggagaaca gatttgttga aattggtgtg acaaggagag aagttcacat atactacctg
 421 gagaaggcca acaaaataaa gtctgagaaa acacatatcc acattttctc atttacagga
 481 gaggaaatgg ctacaaaagc ggactatact cttgatgaag agagtagagc caggatcaag
 541 accagactat tcactataag acaagaaatg gccagtagag gcctctggga ttcctttcgt
 601 cagtccgaga gaggcgaaga gacaattgaa gaaagatttg aaatcacagg gacgatgcgc
 661 aagcttgcca attacagtct cccaccgaac ttctccagcc ttgaaaattt tagagtctat
 721 gtggatggat tcgaaccgaa cggctgcatt gagagtaagc tttctcaaat gtccaaagaa
 781 gtaaatgcca gaatcgaacc attttcaaag acaacacccc gaccactcaa aatgccaggt
 841 ggtccaccct gccatcagcg atctaaattc ttgctaatgg atgctctgaa actgagcatt
 901 gaggacccaa gtcacgaggg agagggaata ccactatatg atgcaatcaa atgcatgaaa
 961 actttctttg gatggaaaga gcccagtatt gttaaaccac atgaaaaggg tataaacccg
1021 aactatctcc aaacttggaa gcaagtatta agagaaatac aagaccttga gaacgaagaa
1081 aggaccccca agaccaagaa tatgaaaaaa acaagccaat gaaatgggc actaggtgaa
1141 aatatgcac agagaaagt ggattttgag gattgtaaag acatcagtga tttaaaacag
1201 tatgacagcg atgagccaga aacaaggtct cttgcaagtt ggattcaaag tgagttcaac
1261 aaagcttgtg agctgacaga ttcaagctgg atagagctcg atgaaattgg ggaggatgtc
1321 gccccaatag aatacattgc gagcatgagg agaaattatt ttactgctga gatttcccat
1381 tgtagagcaa cagaatatat aatgaaagga gtgtacatca acactgctct actcaatgca
1441 tcctgtgctg cgatggatga atttcaatta attccgatga taagtaaatg caggaccaaa
1501 gaagggagaa ggaaaacaaa tttatatgga ttcataataa agggaaggtc ccatttaaga
1561 aatgatactg acgtggtgaa ctttgtaagt atggaatttt ctctcactga tccaagattt
1621 gagccacaca atgggaaaaa atactgcgtt ctagaaattg agacatgct tctaaggact
1681 gctgtaggtc aagtgtcaag acccatgttt ttgtatgtaa ggacaaatgg aacctctaaa
1741 attaaaatga atggggaat ggaaatgagg cgctgcctcc ttcagtctct gcaacagatt
1801 gaaagcatga tcgaagctga gtcctcagtc aaagaaaagg acatgaccaa gaatttttt
1861 gagaacaaat cagagacatg gcctatagga gagtccccca aaggagtgga agagggctca
1921 atcgggaagg tttgcaggac ttattagca aaatctgtgt ttaacagttt atatgcatct
1981 ccacaactgg aagggtttc agctgaatct aggaaattac ttctcattgt tcaggctctt
2041 agggataacc tggaacctgg aacctttgat attggggggt tatatgaatc aattgaggag
2101 tgcctgatta atgatccctg ggttttgctt aatgcatctt ggttcaactc cttccttaca
2161 catgcactga gtagttgtg gcaatgctac tatttgctat ccatactgtc caaaaaagta
2221 ccttgtttct act
```

DEFINITION Influenza A virus (A/equine/Kentucky/5/02 (H3N8)) PB1 polymerase 1 gene, complete cds.

ACCESSION AY855339; SEQ ID NO: 14

```
   1 agcgaaagca ggcaaaccat ttgaatggat gtcaatccga ctctactttt cttaaaggtg
  61 ccagcgcaaa atgctataag cacaacattc ccttatactg gagatcctcc ctacagtcat
```

-continued

```
 121 ggaacaggga caggatacac catggatact gtcaacagaa cacaccaata ttcagaaaag
 181 gggaaatgga caacaaacac tgagattgga gcaccacaac ttaatccaat cgatggacca
 241 cttcctgaag acaatgaacc aagtgggtac gcccaaacag attgtgtatt ggaagcaatg
 301 gctttccttg aagaatccca tcccggaatc tttgaaaatt cgtgtcttga acgatggag
 361 gtgattcagc agacaagagt ggacaaacta acacaaggcc gacaaactta tgattggacc
 421 ttgaatagga tcaacctgc cgcaacagca cttgctaata caattgaagt gttcagatca
 481 aatggtctga cttccaatga atcagggagg ttgatggact tcctcaaaga tgtcatggag
 541 tccatgaaca aggaagaaat ggaaataaca acacacttcc aacgaaagag aagagtaaga
 601 gacaacatga caaagagaat ggtaacacag agaaccatag ggaagaaaaa acaacgatta
 661 aacagaaaga gttatctaat cagaacatta accctaaaca caatgaccaa ggacgctgag
 721 agagggaaat tgaaacgacg agcaatcgca accccaggga tgcagataag aggatttgta
 781 tattttgttg aaacactagc ccgaagaata tgtgaaaagc ttgaacaatc aggattgcca
 841 gttggcggta atgagaaaaa ggccaaactg ctaatgtcg tcagaaaaat gatgactaat
 901 tcccaagaca ctgaactctc cttcaccatc actggggaca ataccaaatg gaatgaaaat
 961 cagaacccac gcatattcct ggcaatgatc acatacataa ctagaaacca gccagaatgg
1021 ttcagaaatg ttctaagcat tgcaccgatt atgttctcaa ataaaatggc aagactgggg
1081 aaaggatata tgtttgaaag caaaagtatg aaactgagag ctcaaatacc agcagaaatg
1141 ctagcaagca ttgacctgaa atatttcaat gattcaacaa aaagaaat taaaaagata
1201 cgaccacttc tggttgacgg gactgcttca ctgagtcctg gcatgatgat gggaatgttc
1261 aacatgttga gcactgtgct gggtgtatcc atattaaacc tgggccagag gaaatacaca
1321 aagaccacat actggtggga tggtctgcaa tcatccgatg actttgcttt gatagtgaat
1381 gcgcctaatc atgaaggaat acaagctgga gtagacagat tctatagaac ttgcaaactg
1441 gtcgggatca acatgagcaa aaagaagtcc tacataaata gaaccggaac attcgaattc
1501 acaagctttt tctaccggta tggttttgta gccaatttca gcatggaact acccagtttt
1561 ggggtttccg gaataaatga atctgcagac atgagcattg gagtgacagt catcaaaaac
1621 aacatgataa ataatgatct cggtcctgcc acggcacaaa tggcactcca actcttcatt
1681 aaggattacc ggtacacata ccggtgccat agaggtgata cccagataca aaccagaaga
1741 tcttttgagt tgaagaaact gtgggaacag actcgatcaa agactggtct actggtatca
1801 gatggggtc aaacctata taacatcaga aacctacaca tcccggaagt tgtttaaaa
1861 tgggagctaa tggatgaaga ttataagggg aggctatgca atccattaaa tccttcgtt
1921 agtcacaaag aaattgaatc agtcaacagt gcagtagtaa tgcctgcgca tggccctgcc
1981 aaaagcatgg agtatgatgc tgttgcaaca cacactctt ggatccccaa gaggaaccgg
2041 tccatattga cacaagccaa aggggaata ctcgaagatg agcagatgta tcagaaatgc
2101 tgcaacctgt ttgaaaaatt cttccccagc agctcataca gaagaccagt cggaatttct
2161 agtatggttg aggccatggt gtccagggcc cgcattgatg cacgaattga cttcgaatct
2221 ggacggataa agaaggatga gttcgctgag atcatgaaga tctgttccac cattgaagag
2281 ctcagacggc aaaaatagtg aatttagctt gatcttcatg aaaaaatgcc ttgtttctac
2341 t
```

DEFINITION Influenza A virus (A/equine/Kentucky/5/02 (H3N8)) PB2 polymerase 2 gene, complete cds.

```
ACCESSION AY855338; SEQ ID NO: 15
   1 agcgaaagca ggtcaaatat attcaatatg gagagaataa aagaactgag agatctgatg
  61 ttacaatccc gcacccgcga gatactaaca aaaactactg tggaccacat ggccataatc
 121 aagaaataca catcaggaag acaagagaag aaccctgcac ttaggatgaa atggatgatg
 181 gcaatgaaat acccaattac agcagataag aggataatgg agatgattcc tgagagaaat
 241 gaacagggac aaacccttg gagcaaaacg aacgatgctg gctcagaccg cgtaatggta
 301 tcacctctgg cagtgacatg gtggaatagg aatggaccaa caacgagcac aattcattat
 361 ccaaaagtct acaaaactta ttttgaaaag gttgaaagat tgaaacacgg aacctttggc
 421 cccgttcatt ttaggaatca agtcaagata agacgaagag ttgatgtaaa ccctggtcac
 481 gcggacctca gtgccaaaga agcacaagat gtgatcatgg aagttgtttt cccaaatgaa
 541 gtgggagcca gaattctaac atcggaatca caactaacaa taccaaaga gaaaaggaa
 601 gaacttcagg actgcaaaat tgctcccttg atggtagcat acatgctaga aagagagttg
 661 gtccgaaaaa caaggttcct cccagtggca ggcggaacaa gcagtgtata cattgaagtg
 721 ttgcatctga ctcagggaac atgctgggag caaatgtaca ccccaggagg agaagttaga
 781 aacgatgata ttgatcaaag tttaattatt gcagcccgga acatagtgag aagagcgaca
 841 gtatcagcag atccactagc atccctactg gaaatgtgcc acagtacaca gattggtgga
 901 ataaggatgg tagacatcct taagcagaat ccaacagagg aacaagctgt ggatatatgc
 961 aaagcagcaa tgggattgag aattagctca tcattcagct ttggtggatt caccttcaaa
1021 agaacaagtg gatcatcagt caagagagaa gaagaaatgc ttacgggcaa ccttcaaaca
1081 ttgaaaataa gagtgcatga gggctatgaa gaattcacaa tggtcggaag aagagcaaca
1141 gccattctca gaaaggcaac cagaagattg attcaattga tagtaagtgg gagagatgaa
1201 caatcaattg ctgaagcaat aattgtagcc atggtgtttt cgcaagaaga ttgcatgata
1261 aaagcagttc gaggcgattt gaactttgtt aatagagcaa atcagcgttt gaaccccatg
1321 catcaactct tgaggcattt ccaaaaagat gcaaaagtgc ttttccaaaa ttggggaatt
1381 gaacccatcg acaatgtaat gggaatgatt ggaatattgc ctgacatgac cccaagcacc
1441 gagatgtcat tgagaggagt gagagtcagc aaaatgggag tggatgagta ctccagcact
1501 gagagagtgg tggtgagcat tgaccgtttt ttaagagttc gggatcaaag gggaaacata
1561 ctactgtccc ctgaagaagt cagtgaaaca caaggaacgg aaaagctgac aataatttat
1621 tcgtcatcaa tgatgtggga gattaatggt cccgaatcag tgttggtcaa tacttatcaa
1681 tggatcatca ggaactggga aattgtaaaa attcagtggt cacaggaccc cacaatgtta
1741 tacaataaga tagaatttga gccattccag tccctggtcc ctaggccac cagaagccaa
1801 tacagcggtt tcgtaagaac cctgtttcag caaatgcgag atgtacttgg aacatttgat
1861 actgctcaaa taataaaact cctcccttt gccgctgctc ctccggaaca gagtaggatg
1921 cagttctctt ctttgactgt taatgtaaga ggatcgggaa tgaggatact tgtaagaggc
1981 aattccccag tgttcaacta caataaagcc actaaaaggc tcacagtcct cggaaaggat
2041 gcaggtgcgc ttactgagga cccagatgaa ggtacggctg gagtagaatc tgctgttcta
2101 agagggtttc tcattttagg taaagaaaac aagagatatg cccagcact aagcatcaat
2161 gaactaagca aacttgcaaa aggggagaaa gccaatgtac taattgggca aggggacgta
2221 gtgttggtaa tgaaacggaa acgtgactct agcatactta ctgacagcca gacagcgacc
```

-continued

```
2281 aaaaggattc ggatggccat caattagtgt tgaattgttt aaaaacgacc ttgtttctac
2341 t
```

DEFINITION Influenza A virus (A/equine/Kentucky/1/91 (H3N8)) hemagglutinin precursor (HA) gene, complete cds.

```
ACCESSION L39918; SEQ ID NO: 16
    1 agcaaaagca ggggatattt ctgtcaatca tgaagacaac cattattttg atactactga
   61 cccattgggt ctacagtcaa aacccaacca gtggcaacaa cacagccaca ttatgtctgg
  121 gacaccatgc agtagcaaat ggaacattgg taaaaacaat aactgatgac caaattgagg
  181 tgacaaatgc tactgaatta gttcagagca tttcaatagg gaaaatatgc aacaactcat
  241 atagagttct agatggaaga aattgcacat taatagatgc aatgctagga gacccccact
  301 gtgatgtctt tcagtatgag aattgggacc tcttcataga aagaagcagc gctttcagca
  361 gttgctaccc atatgacatc cctgactatg catcgctccg gtccattgta gcatcctcag
  421 gaacattgga attcacagca gagggattca catggacagg tgtcactcaa aacggaagaa
  481 gtggatcctg caaaaggggga tcagccgata gtttctttag ccgactgaat tggctaacaa
  541 aatctggaaa ctcttacccc acattgaatg tgacaatgcc taacaataaa aatttcgaca
  601 aactatacat ctggggggatt catcacccga gctcaaacga gagcagaca aaattgtaca
  661 tccaagaatc aggacgagta acagtctcaa caaaaagaag tcaacaaaca ataatcccta
  721 acatcggatc tagaccgtgg gtcaggggtc aatcaggcag gataagcata tactggacca
  781 ttgtaaaacc tggagatatc ctaatgataa acagtaatgg caacttagtt gcaccgcggg
  841 gatattttaa attgaaaaca gggaaaagct ctgtaatgag atcagatgca cccatagaca
  901 tttgtgtgtc tgaatgtatt acaccaaatg gaagcatccc caacgacaaa ccatttcaaa
  961 atgtgaacaa agttacatat ggaaaatgcc ccaagtatat caggcaaaac actttaaagc
 1021 tggccactgg gatgaggaat gtaccagaaa agcaaatcag aggaatcttt ggagcaatag
 1081 cgggattcat agaaaacggc tgggaaggaa tggttgatgg gtggtatgga ttccgatatc
 1141 aaaactcgga aggaacagga caagctgcag atctaaagag cactcaagca gccatcgacc
 1201 agatcaatgg aaaattaaac agagtgattg aaaggaccaa tgagaaattc catcaaatag
 1261 agaaggaatt ctcagaagta gaagggagaa tccaggattt ggagaagtat gtagaagaca
 1321 ccaaaataga cctatggtcc tacaatgcag aattgctggt ggctctagaa aatcaacata
 1381 caattgactt aacagatgca gaaatgaata attattcga gaagactaga cgccagttaa
 1441 gagaaaacgc ggaagacatg ggaggtggat gtttcaagat ataccacaaa tgtgataatg
 1501 catgcattgg atcaataaga aatgggacat atgaccatta catatacaga gatgaagcat
 1561 taaacaaccg gttcaaatc aaaggtgttg agttgaaatc aggctacaaa gattggatac
 1621 tgtggatttc attcgccata tcatgcttct taatttgcgt tgttctattg ggtttcatta
 1681 tgtgggcttg ccaaaaaggc aacatcagat gcaacatttg catttgagta aactgatagt
 1741 taaaaacacc cttgtttcta ct
```

DEFINITION Influenza A virus (A/equine/Kentucky/1/92 (H3N8)) hemagglutinin precursor (HA) gene, complete cds.

```
ACCESSION L39917; SEQ ID NO: 17
   1 agcaaaagca ggggatattt ctgtcaatca tgaagacaac cattattttg atactactga
  61 cccattgggt ctacagtcaa aacccaacca gtggcaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagggttct agatggaaga aattgcacat taatagatgc aatgctagga gacccccact
 301 gtgatgtctt tcagtatgag aattgggacc tcttcataga aagaagcagc gctttcagca
 361 attgctaccc atatgacatc cctgactatg catcgctccg gtccattgta gcatcctcag
 421 gaacattaga attcacagca gagggattca catggacagg tgtcactcaa aacggaagaa
 481 gtggagcctg caaaaggggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacat gagcagaca aaattgtata
 661 tccaagaaac aggacgagta acagtctcaa caaaagaag tcaacaaaca ataatcccta
 721 acatcggatc tagaccgtgg gtcagggggtc aatcaggcag gataagcata tactggacca
 781 ttgtaaaacc tggagatatc ctaatgataa acagcaatgg caacttagtt gcaccgcggg
 841 gatattttaa attgagaaca gggagaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaaatatat caggcaaaac actttaaagc
1021 tggccactgg gatgaggaat gtaccagaaa agcaaatcag aggaatcttt ggagcaatag
1081 cgggattcat agaaaacggc tgggaaggaa tggttgatgg gtggtatgga ttccgatatc
1141 aaaactcgga aggaacagga caagctgcag atctaaagag cactcaagca gccatcgacc
1201 agatcaatgg aaaattaaac agagtgattg aaaggaccaa tgagaaattc catcaaatag
1261 agaaggaatt ctcagaagta gaagggagaa tccaggattt ggagaagtat gtagaagaca
1321 ccaaaataga cctatggtcc tacaatgcag aattgctagt ggctctagaa atcaacata
1381 caattgactt aacagacgca gaaatgaata aattattcga gaagactaga cgccagttaa
1441 gagaaaacgc ggaagacatg ggaggtggat gtttcaagat ttaccacaaa tgtgataatg
1501 catgcattgg atcaataaga aatgggacat atgaccatta catatacaga gatgaagcat
1561 taaacaaccg atttcaaatc aaaggtgttg aattaaaatc aggctacaaa gattggatac
1621 tgtggatttc attcgccata tcatgcttct taatttgtgt tgttctattg ggtttcatta
1681 tgtgggcttg ccaaaaaggc aacatcagat gcaacatttg catttgagta aactgatagt
1741 taaaaacacc cttgtttcta ct
```

DEFINITION Influenza A virus (A/equine/1/90 (H3N8)) hemagglutinin precursor (HA) gene, complete cds.

```
ACCESSION L39915; SEQ ID NO: 18
   1 agcaaaagca ggggatattt ctgtcaatca tgaaaacaac cattattttg atactactga
  61 cccattgggt ctacagtcaa aacccaacca gtggcaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg aaaaatatgc aacaactcat
```

-continued

```
 241 ataggttct agatggaaga aattgcacat taatagatgc aatgctagga gaccctcact
 301 gtgatgtctt tcagtatgag aattgggacc tcttcataga aagaagcagc gctttcagca
 361 attgctaccc atatgacatc cctgactatg catcgctccg gtccattgta gcatcctcag
 421 gaacattaga attcacagca gagggattca catggacagg tgtcactcaa aacggaggaa
 481 gtggagcctg caaaagagga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacaa tgagcagaca aaattgtata
 661 tccaagaatc aggacgagta acagtctcaa caaaaagaag tcaacaaaca ataatccta
 721 acatcggatc tagaccgtgg gtcaggggtc aatcaggcag gataagcata tactggacca
 781 ttgtaaaacc tggagatatc ctaatgataa acagtaatgg caacttagtt gcaccgcggg
 841 gatattttaa attgagaaca gggaaaagct ctgtaatgag atcagatgca cccatagaca
 901 cttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag aggaatcttt ggagcaatag
1081 cgggattcat agaaaacggc tgggaaggaa tggttgatgg gtggtatgga ttccgatatc
1141 aaaactcgga aggaacagga caagctgcag atctaaagag cactcaagca gccatcgacc
1201 agatcaatgg aaaattaaac agagtgattg aaaggaccaa tgagaaattc catcaaatag
1261 agaaggaatt ctcagaagta aagggagaa tcaaggactt ggagaagtat gtagaagaca
1321 ccaaaataga cctatggtcc tacaatgcag aattgctggt ggctctagaa aatcaacata
1381 caattgactt aacagatgca gaaatgaata aattattcga gaagactaga cgccagttaa
1441 gagaaaacgc ggaagacatg ggaggtggat gtttcaagat ctaccacaaa tgtgataatg
1501 catgcattgg atcaataaga aatgggacat atgaccatta catatacaaa gatgaagcat
1561 taaacaaccg atttcaaatc aaaggtgttg agttgaaatc aggctacaaa gattggatac
1621 tgtggatttc attcgccata tcatgcttct taatttgcgt tgttctattg ggtttcatta
1681 tgtgggcttg ccaaaaaggc aacatcagat gcaacatttg catttgagta aactgatagt
1741 taaaaacacc cttgtttcta ct
```

DEFINITION Influenza A virus (A/equine/Kentucky/1/94 (H3N8)) hemagglutinin precursor (HA) gene, complete cds.

ACCESSION L39914; SEQ ID NO: 19
```
   1 agcaaaagca ggggatattt ctgtcaatca tgaagacaac cattattttg atactactga
  61 cccattgggt ctacagtcaa aacccaacca gtggcaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagagttct agatggaaga aattgcacat taatagatgc aatgctagga gacccccact
 301 gtgatgtctt tcagtatgag aattgggacc tcttcataga aagaagcagc gctttcagca
 361 attgctaccc atatgacatc cctgactatg catcgctccg gtccattgta gcatcctcag
 421 gaacattgga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
```

-continued

```
 601 aactatacat ctgggggatt catcacccga gctcaaacca acagcaaaca gaattgtaca
 661 tccaagaatc aggacgagta acagtctcaa caaaagaag tcaacaaacg ataatcccta
 721 atatcggatc tagaccgtgg gtcaggggtc aatcaggcag gataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg aagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag aggaatcttt ggagcaatag
1081 cgggattcat agaaaacggc tgggaaggaa tggttgatgg gtggtatgga ttccgatatc
1141 aaaactcgga aggaacagga caagctgcag atctaaagag cactcaagca gccatcgacc
1201 agattaatgg aaaattaaac agagtgattg aaaggaccaa tgagaaattc catcaaatag
1261 agaaggaatt ctcagaagta aagggggaaa tccaggactt ggagaagtat gtagaagaca
1321 ccaaaataga ccctatggtcc tacaatgcag aattgctggt ggctctagaa aatcaacata
1381 caattgactt aacagatgca gaaatgaata aattattcga gaagactaga cgccagttaa
1441 gagaaaacgc ggaagacatg ggaggtggat gtttcaagat ttaccacaaa tgtgataatg
1501 catgcattgg atcaataaga aatgggacat atgaccatta catatacaga gatgaagcat
1561 taaacaaccg atttcaaatc aaaggtgttg agttgaaatc aggctacaaa gattggatac
1621 tgtggatttc attcgccata tcatgcttct taatttgcgt tgttctattg ggtttcatta
1681 tgtgggcttg ccaaaaaggc aacatcagat gcaacatttg catttgagta aactgatagt
1741 taaaaacacc cttgtttcta ct
```

DEFINITION Influenza A virus (A/equine/Kentucky/1/81 (H3N8)) nucleoprotein (NP) gene, complete cds.[35]

```
ACCESSION AY291288; SEQ ID NO: 20
   1 agcaaaagca gggtagataa tcactcactg agtgacatca aagtcatggc gtctcaaggc
  61 accaaacgat cttatgagca gatggaaact ggtgggaac gccagaatgc aactgaaatc
 121 agagcatctg ttggaaggat ggtgggagga atcggccggt tctatgttca aatgtgtact
 181 gagcttaaac tcaacgacca tgaagggcgg ctgattcaga acagcataac aatagaaagg
 241 atggtacttt cggcattcga cgaaagaaga aacaagtacc tcgaggagca tcccagtgct
 301 gggaaagacc ccaagaaaac gggaggcccg atatacagaa ggagagatgg gaaatggatg
 361 agagaactca tcctccatga taaagaagaa atcatgagga tctggcgtca ggccaacaat
 421 ggtgaagacg ctactgctgg tcttactcat atgatgatct ggcactccaa tctcaatgac
 481 accacctacc aaagaacaag ggctcttgtt cgggctggga tggatcccag aatgtgctct
 541 ctgatgcaag gatcaactct cccacgagag tctggagctg ccggtgctgc agtgaagggt
 601 gttggaacaa tggtaatgga actcatcagg atgatcaaac gcgggataaa tgatcgaaac
 661 ttctggagag gtgaaaatgg tcgaagaacc agaattgctt atgaaagaat gtgcaacatc
 721 ctcaagggga aattccaaac agcagcacaa cgagcaatga tggaccaagt gaggggagc
 781 cgcaatcctg gaaatgctga gattgaggat ctcatttttct ggcacgatc agcactcatt
 841 ctgagaggat cagtagccca taatcatgc ctacctgcct gtgtttatgg ccttgcagta
 901 gccagtgggt atgactttga aaagaggga tactctctgg ttggaattga tcctttcaaa
```

-continued

```
 961 ctactccaga acagccaaat tttcagtcta atcagaccga agaaaatcc agcacacaag 1021 agccagctgg tgtggatggc atgccattct gcagcatttg aggacctgag agtttcgaat 1081 ttcattagag gaaccaaagt aatcccaaga ggacagttag caaccagggg agtgcaaatt 1141 gcttcaaatg aaaacatgga gacaatagat tctagcacac tcgaactgag gagcagatat 1201 tgggcaataa ggaccaggag tgggggggaac accagtcaac agagagcatc tgcaggacag 1261 ataagtgtgc aacccacttt ctcagtgcag agaaatcttc cctttgaaag agcaaccatt 1321 atggctgcat tcactggaaa cactgagggg aggacttccg acatgagaac ggaaatcata 1381 aggatgatgg aaaatgccag atcagaagat gtgtctttcc aggggcgggg agtcttcgag 1441 ctctcggacg aaaaggcaac gaacccgatc gtgccttcct ttgacatgag caatgaaggg 1501 tcttatttct cggagacaa tgctgaggag tttgacagtt aaagaaaaat accttgttt 1561 ctact
```

DEFINITION Influenza A virus (A/Equine/Kentucky/1/92 (H3N8)) gene for hemagglutinin precursor, partial cds.

ACCESSION D30683; SEQ ID NO: 21

```
   1 gtcaatcatg aagacaacca ttattttgat actactgacc cattgggtct acagtcaaaa 61 cccaaccagt ggcaacaaca cagccacatt atgtctggga caccatgcag tagcaaatgg 121 aacattggta aaaacaataa ctgatgacca aattgaggtg acaaatgcta ctgaattagt 181 tcagagcatt tcatagggga aaatatgcaa caactcatat agggttctag atggaagaaa 241 ttgcacatta atagatgcaa tgctaggaga ccccactgt gatgtctttc agtatgagaa 301 ttgggaccctc ttcatagaaa gaagcagcgc tttcagcaat tgctacccat atgacatccc 361 tgactatgca tcgctccggt ccattgtagc atcctcagga acattagaat tcacagcaga 421 gggattcaca tggacaggtg tcactcaaaa cggaggaagt ggagcctgca aaggggatc 481 agccgatagt ttctttagcc gactgaattg gctaacaaaa tctggaaact cttaccccac 541 attgaatgtg acaatgccta acaataaaaa tttcgacaaa ctatacatct ggggggattca 601 tcacccgagc tcaaacaatg agcagacaaa attgtatatc caagaaacag gacgagtaac 661 agtctcaaca aaaagaagtc aacaaacaat aatccctaac atcggatcta accgtgggt 721 caggggtcaa tcaggcagga taagcatata ctggaccatt gtaaaacctg gagatatcct 781 aatgataaac agcaatggca acttagttgc accgcgggga tattttaaat tgagaacagg 841 gagaagctct gtaatgagat cagatgcacc catagacatt tgtgtgtctg aatgtattac 901 accaaatgga agcatcccca cgacaaacc atttcaaaat gtgaacaaag ttacatatgg 961 aaaatgcccc aaatatatca ggcaaaacac tttaaagctg ccactgggga tgaggaatgt 1021 accagaaaag caaatcagag gaatctttgg agcaatagcg ggattcatag aaaacggctg 1081 ggaaggaatg gttgat
```

DEFINITION Influenza A virus (A/equine/Kentucky/1/97 (H3N8)) hemagglutinin precursor (HA1) mRNA, partial cds.

ACCESSION AF197249; SEQ ID NO: 22

```
   1 agcaaaagca ggggatattt ctgtcaatca tgaagacaac cattattttg atactactga 61 cccattgggc ctacagtcaa aacccaatca gtggcaacaa cacagccaca ttgtgtctgg 121 gacaccatgc agtagcaaat ggaacattgg taaaaacaat aactgatgat caaattgagg
```

-continued

```
 181 tgacaaatgc tactgaatta gttcagagca tttcaatggg gaaaatatgc aacaactcat
 241 atagagttct agatggaaga aattgcacat taatagatgc aatgctagga gaccccact
 301 gtgatgtctt tcagtatgag aattgggacc tctttataga aagaagcagc gctttcagca
 361 attgctaccc atatgacatc cctgactatg catcgctccg gtccattgta gcatcctcag
 421 gaacattgga attcacagca gagggattca catggacagg tgtcactcaa aacggaagaa
 481 gtggagcctg caaaaggggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca agagcagaca aaattgtaca
 661 tccaagaatc aggacgagta acagtctcaa caaaaagaag tcaacaaaca ataatcccta
 721 acatcggatc tagaccgtgg gtcagggggtc aatcaggcag ataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatctc caacgacaaa ccattccaaa
 961 atgtgaacaa agttacatat ggaaaatgcc ccaagtatat caggcaaaac actttaaagc
1021 tggccactgg gatgaggaat gaaccagaaa agcaaatcag a
```

DEFINITION Influenza A virus (A/equine/Kentucky/1/96 (H3N8)) hemagglutinin precursor (HA1) mRNA, partial cds.

```
ACCESSION AF197248; SEQ ID NO: 23
   1 agcaaaagca ggggatattt ctgtcaatca tgaagacaac cattattttg atactactga
  61 cccattgggt ctacagtcaa aacccaacca gtggcaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagagttct agatggaaga aattgcacat taatagatgc aatgctagga gaccccact
 301 gtgatgtctt ccagtatgag aattgggacc tcttcataga aagaagcagc gctttcagca
 361 attgctaccc atatgacatc cctgactatg catcgctccg gtccattgta gcatcctcag
 421 gaacattaga attcacagca gagggattca catggacagg tgtcactcaa aacggaagaa
 481 gtggagcctg caaaaggggga tcagccgata gtttctttag ccgactgaat tggctaacaa
 541 aatctggaaa ctcttacccc acattgaatg tgacaatgcc taacaataaa aatttcgaca
 601 aactatacat ctggggggatt catcacccga gctcaaacca aaagcagaca gaattgtaca
 661 tccaagaatc aggacgagta acagtctcaa caaaaagaag tcaacaaacg ataatcccta
 721 atatcggatc tagaccgtgg gttaggggtc aatcaggcag ataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag a
```

DEFINITION Influenza A virus (A/equine/Kentucky/9/95 (H3N8)) hemagglutinin precursor (HA1) mRNA, partial cds.

ACCESSION AF197247; SEQ ID NO: 24
```
   1 agcaaaagca ggggatattt ctgtcaatca tgaagacaac cattattttg atactactga
  61 cccattgggt ctacagtcaa aacccaacca gtggaaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 atagagttct agatggaaga aattgcacat taatagatgc aatgctagga gaccccact
 301 gtgatgtctt ccagtatgag aattgggacc tcttcataga aagaagcagc gctttcagca
 361 attgctaccc atatgacatc cctgactatg catcgctccg gtccattgta gcatcctcag
 421 gaacattgga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca aaagcagaca gaattgtaca
 661 tccaagaatc aggacgagta acagtctcaa caaaaagaag tcaacaaacg ataatcccta
 721 atatcggatc tagaccgtgg gtcaggggtc aatcaggcag ataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
 961 atgtgaacaa agttacatat ggaaaatgcc ccaagtatat caggcaaaac actttaaagc
1021 tggccactgg gatgaggaat gtaccagaaa agcaaatcag a
```

DEFINITION Influenza A virus (A/equine/Kentucky/1/98 (H3N8)) hemagglutinin precursor (HA1) mRNA, partial cds.

ACCESSION AF197241; SEQ ID NO: 25
```
   1 agcaaaagca ggggatattt ctgtcaatca tgaagacaac cattattttg atactactga
  61 cccattgggt ctacagtcaa aacccaacca gtggaaacaa cacagccaca ttatgtctgg
 121 gacaccatgc agtagcaaat ggaacattgg taaaaacaat aactgatgac caaattgagg
 181 tgacaaatgc tactgaatta gttcagagca tttcaatagg gaaaatatgc aacaactcat
 241 ataaagttct agatggaaga aattgcacat taatagatgc aatgctagga gaccccact
 301 gtgatgtctt ccagtatgag aattgggacc tcttcataga aagaagcagc gctttcagca
 361 attgctaccc atatgacatc cctgactatg catcgctccg gtccattgta gcatcCtcag
 421 gaacattaga attcacagca gagggattca catggacagg tgtcactcaa aacggaagaa
 481 gtggagcctg caaaagggga tcagccgata gtttctttag ccgactgaat tggctaacaa
 541 aatctggaaa ctcttacccc acattgaatg tgacaatgcc taacaataaa aatttcgaca
 601 aactatacat ctgggggatt catcacccga gctcaaacca acagcagaca gaattgtaca
 661 tccaagaatc aggacgagta acagtctcaa caaaaagaag tcaacaaacg atagtcccta
 721 atatcggatc tagaccgtgg gttaggggtc aatcaggcag ataagcata tactggacca
 781 ttgtaaaacc tggagatatc ctaatgataa acagtaatgg caacttagtt gcaccgcggg
 841 gatattttaa attgaaaaca gggaaaagct ctgtaatgag atcagatgca cccatagaca
 901 tttgtgtgtc tgaatgtatt acaccaaatg gaagcatccc caacgacaaa ccatttcaaa
```

-continued

```
 961 atgtgaacaa agttacatat ggaaaatgcc ccaagtatat caggcaaaac actttaaagc 1021 tggccactgg gatgaggaat ataccagaaa agcaaatcag a
```

DEFINITION Influenza A virus (A/eq/Kentucky/81(H3N8))
hemagglutinin mRNA, complete cds.

```
ACCESSION U58195; SEQ ID NO: 26
    1 agcaaaagca ggggatactt tctgtcaatc atgaagacaa ccattatttt gatactactg 61 acccattggg tctacagtca aacccaacc agtggcaaca cacagccac actatgtctg 121 ggacaccatg cagtagcaaa tggaacattg gtaaaaacaa taactgatga ccaaattgag 181 gtgacaaatg ctactgaatt agttcagagc acttcaatag ggaaaatatg caacaaccca 241 tatagggttc tagatggaag aaactgcaca ttaatagatg caatgctagg agatccccac 301 tgtgatgttt ttcagtatga gaattgggac ctcttcatag aaagaagcag cgctttcagc 361 aattgctacc catatgacat ccctgactat gcatcgctcc ggtctattgt ggcatcttca 421 ggaacattag aattcacagc agagggattc acatggacag tgtcactca aaacggagga 481 agtggagcct gcagaagggg gtcagccgat agtttcttta gccgactgaa ttggctaaca 541 aaatctggaa attcttaccc cacattgaat gtaacaatgc taacaataa caatttcgat 601 aaactataca tctgggggat ccatcacccg agcacaaaca tgagcagac aaaattgtat 661 atccaagaat cagggcgagt aacagtctca acaaaaagaa gtcaacaaac aataatcccc 721 aacatcggat ctagaccgtg ggtcaggggt caatcaggca ggataagcat atattggacc 781 attgtgaaac ctggagatat cctaatgata acagtaatg gcaacttagt tgcaccgcgg 841 ggatatttta aaatgcgaac agggaaaagc tctgtaatga gatcagatgc acccatagac 901 acttgtgtgt ccgagtgtat tacaccaaat ggaagcatcc ccaacgacaa accatttcaa 961 aatgtgaaca agttacata tggaaaatgc cccaagtata tcaagcagaa tactttgaag 1021 ctggccactg ggatgaggaa tgtaccagaa aagcaaatca gaggaatctt ggagcaata 1081 gcgggattca tagaaaacgg ctgggaagga atggttgatg ggtggtatgg attccgatat 1141 cagaattcgg aaggaacagg acaagctgca gatctaaaga gcactcaagc agccatcgac 1201 cagatcaatg gaaaattgaa cagagtgatt gaaaggacca atgagaaatt ccatcaaata 1261 gagaaggaat tctcagaagt agaagggaga atccaggact ggagaagta tgtagaagac 1321 accaaaatag acctatggtc ctacaatgca gagttactgg tggctctaga aaatcaacat 1381 acgattgact aacagatgc agaaatgaat aaattattcg agaagactag cgccagtta 1441 agagaaaacg cggaagacat ggggggtgga tgtttcaaga tttatcacaa atgtgataat 1501 gcatgcattg gatcaataag aaatgggaca tatgaccatt acatatacag agatgaagca 1561 ttaaacaacc gatttcaaat taaggtgtt gaattgaaat caggctacaa agattggata 1621 ctgtggattt cattcgccat atcatgcttc ttaatttgcg ttgttctatt gggtttcatc 1681 atgtgggctg ccaaaaagg caacatcaga tgcaacattt gcatttgagt aaactgataa 1741 ttaaaaacac ccttgtttct act
```

DEFINITION Influenza A virus (A/equine/Kentucky/2/86 (H3N8)) membrane protein M1 and membrane protein M2 genes, complete cds.

ACCESSION M63540; SEQ ID NO: 27

```
   1 agcaaaagca ggtagatatt taaagatgag tcttctaacc gaggtcgaaa cgtacgttct
  61 ctctattgta ccatcaggcc ccctcaaagc cgagatcgcg cagagacttg aagatgtctt
 121 tgcagggaag aacaccgatc ttgaggcact catggaatgg ctaaagacaa gaccaatcct
 181 gtcacctctg actaaaggga ttttaggatt tgtgttcacg ctcaccgtgc ccagtgagcg
 241 aggactgcaa cgtagacgct ttgtccaaaa tgcccttagt ggaaacggag atccaaataa
 301 catggacaga gcagtaaaac tgtacaagaa gcttaaaaga gaataacat tccatggggc
 361 aaaagaggtg gcactcagct attccactgg tgcactagcc agctgcatgg gactcatata
 421 caacagaatg gggactgtga caaccgaagt ggcatttggc ctggtatgcg ccacatgtga
 481 acagattgct gattcccagc atcgatctca caggcagatg gtgacaacaa ccaacccact
 541 aatcagacat gaaaacagaa tggtactagc cagtaccaca gctaaaacca tggagcaggt
 601 ggcagggtcg agtgagcagg cagcagaggc catggaggtt gctagtaagg ccaggcagat
 661 ggtgcaggca atgaggacca ttgggaccca ccctagctcc agtgccggtt tgaaagatga
 721 tcttcttgaa aatttgcagg cctaccagaa acggatggga gtgcaaatgc agcggttcaa
 781 gtgatcctct cgttattgca gcaagtatca ttgggatctt gcacttgata ttgtggattc
 841 ttgatcgcct tttcttcaaa ttcatttatc gtctccttaa atacggtttg aaaagagggc
 901 cttctacgga aggagtacct gagtctatga gggaagaata tcggcaggaa cagcagaatg
 961 ctgtggatgt tgacgatggt catttgtca acatagagct ggagtaaaaa actaccttgt
1021 ttctact
```

DEFINITION Influenza A virus isolate A/equine/Kentucky/ 76 nonstructural protein, complete cds.

ACCESSION M80971; SEQ ID NO: 28

```
   1 agcaaaagca gggtgacaaa aacataatgg attccaacac tgtgtcaagc tttcaggtag
  61 actgtttct ttggcatgtc cgcaaacgat ttgcagacca agaactgggt gatgccccat
 121 tccttgaccg gcttcgccga gaccagaagt ccctaaaagg aagaggcagc actcttggtc
 181 tggacatcga aacagccact cgtgcaggaa agcagatagt ggagcggatt ctggaagagg
 241 agtcagatga ggcacttaaa atgaccattg cctctgttcc tgcttcacgc tacttaactg
 301 acatgactct tgatgagatg tcaagagact ggttcatgct catgcccaag cagaaagtaa
 361 caggctccct atgtataagg atggaccagg caatcatgga taagaacatc atactaaaag
 421 caaactttag tgtgattttc gaaaggctgg agacactaat actacttaga gctttcaccg
 481 aagaaggagc agtcgttggc gaaatttcac cattgccttc tcttccagga catactaatg
 541 aggatgtcaa aaatgcaatt ggggtcctca tcggaggact aaatggaat gataacacag
 601 ttagaatctc tgaaactcta cagagattcg cttggagaag cagtcatgag aatgggagac
 661 cttcattccc tccaaagcag aaacgaaaaa tggcgagaac aattgagtca gaagtttgaa
 721 gaaataaggt ggttgattga agaagtgcga catagattga aaaatacaga aaatagtttt
 781 gaacaaataa catttatgca agccttacaa ctattgcttg aagtagaaca agagataaga
 841 actttctcgt ttcagcttat ttaatgataa aaaacaccct tgtttctact
```

DEFINITION Influenza A virus (A/eq/Kentucky/92(H3N8))
matrix proteins M1 and M2 (M) gene, complete cds.

```
ACCESSION AF001683; SEQ ID NO: 29
   1 atgagtcttc tgaccgaggt cgaaacgtac gttctctcta tcgtaccatc aggcccctc 61 aaagccgaga tcgcgcagag acttgaagat gtctttgcag ggaagaacac cgatcttgag 121 gcactcatgg aatggctaaa gacaagacca atcctgtcac ctctgactaa agggatttta 181 ggattcgtat tcacgctcac cgtgcccagt gagcgaggac tgcagcgtag acgctttgtc 241 caaaatgccc ttagtggaaa cggagatcca acaacatgg acagagcagt aaaactgtac 301 aggaaactta aaagagaaat aacattccat ggggcaaaag aggtggcact cagctattcc 361 actggtgcac tagccagctg catgggactc atatacaaca gaatgggaac tgtgacaacc 421 gaagtggcat ttggcctagt atgcgccaca tgtgaacaga ttgctgattc ccagcatcga 481 tctcacaggc agatggtgac aacaaccaac ccattaatca gacatgaaaa cagaatggta 541 ttagccagta ccacggctaa agccatggag cagatggcag ggtcgagtga gcaggcagca 601 gaggccatgg aggttgctag taaggctagg cagatggtac aggcaatgag gaccattggg 661 acccacccta gctccagtgc cggtttgaaa atgatctcc ttgaaaattt gcaggcctac 721 cagaaacgga tgggagtgca aatgcagcga ttcaagtgat cctctcgtta ttgcagcaag 781 tatcattggg atcttgcact tgatattgtg gattcttgat cgccttttct tcaaattcat 841 ttatcgtcgc cttaaatacg ggttgaaaag agggccttct acggaaggag tacctgagtc 901 tatgagggaa gaatatcggc aggaacagca gaatgctgtg gatgttgacg atggtcattt 961 tgtcaacata gagctggagt aa
```

DEFINITION Influenza A virus (A/eq/Kentucky/81(H3N8))
matrix proteins M1 and M2 (M) gene, complete cds.

```
ACCESSION AF001676; SEQ ID NO: 30
   1 atgagtcttc taaccgaggt cgaaacgtac gttctctcta tcgtaccatc aggcccctc 61 aaagccgaga tcgcgcagag acttgaagat gtctttgcag ggaagaacac cgatcttgag 121 gcactcatgg aatggctaaa gacaagacca atcctgtcac ctctgactaa agggatttta 181 ggatttgtgt tcacgctcac cgtgcccagt gagcgaggac tgcagcgtag acgctttgtc 241 caaaatgccc ttagtggaaa cggagatcca acaacatgg acagagcagt aaaactgtac 301 aggaagctta aaagagaaat aacattccat ggggcaaaag aggtggcact cagctattcc 361 actggtgcac tagccagctg catgggactc atatacaaca gaatggggac tgtgacaacc 421 gaagtggcat ttggcctggt atgcgccaca tgtgaacaga ttgctgattc ccagcatcga 481 tctcacaggc agatggtgac aacaaccaac ccactaatca gacatgaaaa cagaatggta 541 ctagccagta ccacagctaa agccatggaa cagatggcag ggtcgagtga gcaggcagca 601 gaggccatgg aggttgctag taaggccagg cagatggtac aggcaatgag gaccattggg 661 acccacccta gctccagtgc cggtttgaaa gatgatcttc ttgaaaattt gcaggcctac 721 cagaaacgga tgggagtgca aatgcagcga ttcaagtgac cctctcgtta ttgcagcaag 781 tatcattggg atcttgcact tgatattgtg gattcttgat cgccttttct tcaaattcat 841 ttatcgtcgc cttaaatacg gtttgaaaag agggccttct acggaaggag tacctgagtc 901 tatgagggaa gaatatcggc aggaacagca gaatgctgtg gatgttgacg atggtcattt 961 tgtcaacata gagctggagt aa
```

DEFINITION Influenza A virus (A/eq/Kentucky/92(H3N8)) nonstructural proteins NS1 and NS2 (NS) gene, complete cds.

```
ACCESSION AF001671; SEQ ID NO: 31
   1 atggattcca acactgtgtc aagctttcag gtagactgtt ttctttggca tgtccgcaaa 61 cgattcgcag accaagaact gggtgatgcc ccattccttg accggcttcg ccgagaccag 121 aagtccctaa aaggaagagg tagcactctt ggtctggaca tcgaaacagc cactcgtgca 181 ggaaagcaga tagtggagca gattctggaa gaggaatcag atgaggcact taaaatgacc 241 attgcctctg ttcctgcttc acgctactta actgacatga ctcttgatga gatgtcaaga 301 gactggttca tgctcatgcc caagcagaaa gtaacaggct ccctatgtat aagaatggac 361 caggcaatca tggataagaa catcatactt aaagcaaact ttagtgtgat tttcgaaagg 421 ctggaaacac taatactact tagagccttc accgaagaag gagcagtcgt tggcgaaatt 481 tcaccattgc cttctcttcc aggacatact aatgaggatg tcaaaaatgc aattggggtc 541 ctcatcggag gacttaaatg gaatgataat acggttagaa tctctgaaac tctacagaga 601 ttcgcttgga gaagcagtca tgagaatggg agaccttcat tccctccaaa gcagaaacga 661 aaaatggaga gaacaattga gccagaagtt tgaagaaata agatggttga ttgaagaagt 721 gcgacataga ttgaaaaata cagaaaatag ttttgaacaa ataacattta tgcaagcctt 781 acaactattg cttgaagtag aacaagagat aagaactttc tcgtttcagc ttatttaa
```

DEFINITION Influenza A virus (A/eq/Kentucky/1/88 (H3N8)) nonstructural proteins NS1 and NS2 (NS) gene, complete cds.

```
ACCESSION AF001664; SEQ ID NO: 32
   1 atggattcca acactgtgtc aagctttcag gtagactgtt ttctttggca tgtccgcaaa 61 cgatttgcag accaagaact gggtgatgcc ccattccttg accggcttcg ccgagaccag 121 aagtccctaa aaggaagagg cagcactctt ggtctggaca tcgaaacagc cactcgtgca 181 ggaaagcaga tagtggagca gattctggaa gaggaatcag atgaggcact taaaatgacc 241 attgcctctg ttcctgcttc acgctactta actgacatga ctcttgatga gatgtcaaga 301 gactggttca tgctcatgcc caagcagaaa gtaacaggct ccctatgtat aaggatggac 361 caggcaatca tggataagaa catcatacta aaagcaaact ttagtgtgat tttcgaaagg 421 ctggagacac taatactact tagagccttc accgaagaag gagcagtcgt tggcgaaatt 481 tcaccattgc cttctcttcc aggacatact aatgaggatg tcaaaaatgc aattggggtc 541 ctcatcggag gacttaaatg gaatgataat acagttagag tctctgaaac tctacagaga 601 ttcgcttgga gaagcagtca tgagaatggg agaccttcat tccctccaaa gcagaaacga 661 aaaatggcga gaacaattga gccagaagtt tgaagaaata agatggttga ttgaagaagt 721 gcgacataga ttgaaaaata cagaaaatag ttttgaacaa ataacattta tgcaagcctt 781 acaactattg cttgaagtag aacaagagat aagaactttc tcgtttcagc ttatttaa
```

DEFINITION Influenza A/equine/Kentucky/2/86 (H3N8) nucleoprotein (seg 5) mRNA, complete cds.

```
ACCESSION M30751; SEQ ID NO: 33
   1 agcaaaagca gggtagataa tcactcactg agtgacatca aagtcatggc gtctcaaggc
  61 accaaacgat cttatgagca gatggaaact ggtggggaac gccagaatgc aactgaaatc
 121 agagcatctg tcggaaggat ggtgggagga atcggccggt tctatgttca gatgtgtact
 181 gagcttaaac tcaacgacca tgaagggcgg ctgattcaga acagcataac aatagaaagg
 241 atggtacttt cggcattcga cgaaagaaga aacaagtacc tcgaggagca tcccagtgct
 301 gggaaagacc ccaagaaaac gggaggcccg atatacagaa ggaaagatgg gaaatggatg
 361 agagaactca tcctccatga taaagaagaa atcatgagga tctggcgtca ggccaacaat
 421 ggtgaagacg ctactgctgg tcttactcat atgatgatct ggcactccaa tctcaatgac
 481 accacatacc aaagaacaag ggctcttgtt cgggctggga tggatcccag aatgtgctct
 541 ctgatgcaag atcaaccct cccacggaga tctggagctg ccggtgctgc agtaaaaggt
 601 gttggaacaa tggtaatgga actcatcagg atgatcaaac gcgggataaa tgatcgaaat
 661 ttctggagag gtgaaaatgg tcgaagaacc agaattgctt atgaaagaat gtgcaatatc
 721 ctcaaaggga aattccaaac agcagcacaa cgggcaatga tggaccaagt gagggagggc
 781 cgcaatcctg gaaatgctga gattgaggat ctcatttttct ggcacgatc agcactcatt
 841 ttgagaggat cagtagccca taaatcatgc ctacctgcct gtgtttatgg ccttgcagta
 901 gccagtgggt atgactttga aaggaagga tactctctgg ttggaattga tcctttcaaa
 961 ctactccaga cagccaaat tttcagtcta atcagaccga agaaaaatcc agcacacaag
1021 agccagttgg tgtggatggc atgccattct gcagcatttg aggacctgag agttttgaat
1081 ttcattagag gaaccaaagt aatcccaaga ggacagttag caaccagagg agtgcaaatt
1141 gcttcaaatg aaaacatgga gacaatagat tctagcacac tcgaactgag gagcagatat
1201 tgggcaataa ggaccaggag tggagggaac accagtcaac agagagcatc tgcaggacag
1261 ataagtgtgc aacccacttt ctcagtgcag agaaatcttc cctttgaaag agcaaccatt
1321 atggctgcat tcactgggaa cactgagcgg aggacttccg acatgagaac ggaaatcata
1381 aggatgatgg aaaatgccag atcagaagat gtgtcttttcc aggggcgggg agtcttcgag
1441 ctctcggacg aaaaggcaac gaacccgatc gtgccttcct ttgacatgag caatgaaggg
1501 tcttatttct tcggagacaa tgctgaggag tttgacagtt aaagaaaaat acccttgttt
1561 ctact
```

DEFINITION Influenza A/Equine/Kentucky/2/86 (H3N8), PB2 polymerase, complete cds.

```
ACCESSION M73526 M36049; SEQ ID NO: 34
   1 agcaaaagca ggtcaaatat attcaatatg gagagaataa agaactgag agatctaatg
  61 tcacagtccc gcacccgcga gatactaaca aaaactactg tggaccatat ggccataatc
 121 aagaaataca catcaggaag acaagagaag aaccccgcac ttaggatgaa gtggatgatg
 181 gcaatgaaat acccaattac agcagataag aggataatgg aaatgattcc tgagagaaat
 241 gaacagggc aaacccttg gagcaaaacg aacgatgctg gctcagaccg cgtaatggta
 301 tcacctctgg cagtgacatg gtggaatagg aatggaccaa caacgagcac aattcattat
 361 ccaaaagtct acaaaactta ttttgaaaaa gttgaaaggt taaacacgg aacctttggc
```

-continued

```
 421 cccgttcatt ttaggaatca agtcaagata agacggagag ttgacgtaaa ccctggtcac
 481 gcggacctca gtgccaaaga agcacaagat gtgatcatgg aagttgtttt cccaaatgaa
 541 gtgggagcca gaattctaac atcggaatca caactaacaa taaccaaaga gaaaaagaa
 601 gaacttcagg actgcaaaat tgccccttg atggtagcat acatgctaga aagagagttg
 661 gtccgaaaaa caaggttcct cccagtggct ggcggaacaa gcagtgtata cattgaggtg
 721 ttgcatctga ctcagggaac gtgctgggaa caaatgtaca ccccaggagg agaagttaga
 781 aacgatgaca ttgatcaaag tttaattatt gctgcccgga acatagtgaa aagagcgaca
 841 gtatcagcag atccactagc atccctgctg gagatgtgcc acagtacaca gattggtgga
 901 ataaggatgg tagacatcct taagcagaat ccaacgagg aacaagctgt ggatatatgc
 961 aaagcagcaa tggggttaag aattagctca tcattcagct ttggtggatt caccttaag
1021 agaacaagtg gatcatcagt caagagagaa gaagaaatgc ttacgggcaa ccttcaaaca
1081 ttgaaaataa gagtgcatga gggctatgaa gaattcacaa tggtcggaag aagagcaaca
1141 gccattctca gaaagacaac cagaagattg attcaattga tagtaagtgg gagagatgaa
1201 cagtcaattg ctgaagcaat aattgtagcc atggtgtttt cgcaagaaga ttgcatgata
1261 aaagcagttc gaggcgattt gaacttcgtt aatagagcaa atcagcgctt gaaccccatg
1321 catcaactct tgaggcattt ccaaaaggat gcaaaagtgc ttttccagaa ttgggggatt
1381 gaacccatcg acaatgtgat gggaatgatc ggaatattgc ccgacatgac cccaagcacc
1441 gagatgtcat tgagaggagt gagagtcagc aaaatgggag tggatgagta ctccagcact
1501 gagagagtgg tggtgagcat tgaccgtttt ttaagagttc gggatcaaag gggaaacata
1561 ctactgtccc ctgaagaggt cagtgaaaca caaggaacgg aaaagctgac aataatttat
1621 tcatcatcaa tgatgtggga gattaatggt cccgagtcag tgttggtcaa tacttatcaa
1681 tggatcatca gaaactggga aattgtgaaa attcaatggt cacaggatcc cacaatgtta
1741 tacaataaga tagaatttga gccattccag tccctggtcc ctaggccac cagaagccaa
1801 tacagcggtt tcgtaaggac cctgtttcag caaatgcgag atgtacttgg aacatttgac
1861 actgctcaaa taataaaact cctcccttt gccgctgctc ctccggaaca gagtagaatg
1921 cagttctctt ctttgactgt taatgtaaga ggatcgggaa tgaggatact tgtaagaggc
1981 aattcccag tgttcaacta caacaaagcc actaagaggc tcacagtcct cggaaaggat
2041 gcaggtgcgc ttactgaaga cccagatgaa ggtacggctg gagtagaatc tgctgttctg
2101 agagggtttc tcatcttagg taaagaaaac aagagatatg gcccagcact aagcatcaat
2161 gaactgagca aacttacaaa aggggagaaa gctaatgtgc taattgggca aggggacgtg
2221 gtgttggtaa tgaaacggaa acgtgactct agcatactta ctgacagtca gacagcgacc
2281 aaaaggattc ggatggccat caattagtgt tgaattgttt aaaaacgacc ttgtttctac
2341 t
```

55
DEFINITION Influenza A/equine/Kentucky/1/87 (H3N8)
hemagglutinin (HA) RNA (seg. 4), complete cds.

```
ACCESSION M24728 J04336; SEQ ID NO: 35
   1 agcaaaagca ggggatattt ctgtcaatca tgaagacaac cattgttttg atactactga
  61 cccattgggt ctacagtcaa aacccaacca gtggcaacaa cacagccaca ttatgtctgg
 121 gacaccatgc agtagcaaat ggaacactgg taaaaacaat aactgatgac cagattgagg
```

-continued

```
 181 tgacaaatgc tactgaatta gttcagagca tttcaatagg gaaaatatgc aacaactcat
 241 atagggttct agatggaaga aattgcacat taatagatgc aatgctagga gacccccact
 301 gtgatgtttt tcngtatgag aattgggacc tcttcataga agaagcagc gctttcagca
 361 attgctaccc atatgacatc cctgactatg catcgctccg gtctattgtg gcatcctcag
 421 gaacattaga attcacagca gagggattca catggacagg tgtcactcaa aacggaagaa
 481 gtggagcctg caaaagggga tcagccgata gtttctttag ccgactgaat tggctaacaa
 541 aatctggaaa ttcttacccc acattgaatg tgacaatgcc taacaataac aatttcgata
 601 aactatacat ctgggggatt catcacccga gctcaaacaa tgagcagaca aaattgtata
 661 tccaagaatc aggacgagta acagtctcaa caaaagaag tcaacaaaca ataatcccca
 721 acatcggatc tagaccgtgg gtcaggggtc aatcaggcag ataagcata tattggacca
 781 ttgtgaaacc tggagatatc ctaatgataa acagtaatgg caacttagtt gcaccgcggg
 841 gatatttcaa attgagaaca gggaaaagct ctgtaatgag atcagatgca cccatagaca
 901 cttgtgtgtc tgaatgtatt acaccaaatg gaagcatccc caacgacaaa ccattccaaa
 961 atgtgaacaa agttacatat ggaaaatgcc ccaagtatat caggcaaaac actttgaagc
1021 tggccactgg gatgaggaat gtaccagaaa agcaaatcag aggaatcttt ggagcaatag
1081 cgggattcat agaaaacggc tgggaaggaa tggttgatgg gtggtatgga ttccgatatc
1141 aaaattcgga aggaacagga caagctggag atctaaagag cactcaagca gccatcgacc
1201 agatcaatgg aaaattaaac agagtgattg aaaggaccaa tgagaaattc atcaaaatag
1261 agaaggaattctcagaagta gaagggagaa tccaggactt ggagaagtat gtagaagaca
1321 ccaaaataga cctatggtcc tacaatgcag aattgctggt ggctctagaa atcaacata
1381 caattgactt aacagatgca gaaatgaata aattattcga gaagactagg cgccagttaa
1441 gagaaaacgc ggaagacatg ggaggtggat gtttcaggat ttaccacaaa tgtgataatg
1501 catgcattgg atcaataaga atgggacat atgaccatta catatacaga gatgaagcat
1561 taaacaaccg atttcaaatt aaaggtgttg agttgaaatc aggctacaaa gattggatac
1621 tgtggatttc attcgccata tcatgcttct taatttgcgt tgttctattg ggtttcatta
1681 tgtgggcttg ccaaaaaggc aacatcagat gcaacatttg catttgagta aactgatagt
1741 taaaaacacc cttgtttcta ct
```

DEFINITION Influenza A/equine/Kentucky/2/86 (H3N8)
hemagglutinin (HA) RNA (seg. 4), complete cds.

```
ACCESSION M24727 J04336; SEQ ID NO: 36
   1 agcaaaagca ggggatattt ctgtcaatca tgaagacaac cattattttg atactactga
  61 cccattgggt ctacagtcaa aacccaacca gtggcaacaa cacagccaca ttatgtctgg
 121 gacaccatgc agtagcaaat ggaacattgg taaaacaat aactgatgac caaattgagg
 181 tgacaaatgc tactgaatta gttcagagca tttcaatagg gaaaatatgc aacaactcat
 241 atagggttct agatggaaga aattgcacat taatagatgc aatgctagga gacccccact
 301 gtgatgtttt tcngtatgag aattgggacc tcttcataga agaagcagc gcttccagca
 361 attgctaccc atatgacatc cctgactatg catcgctccg gtctattgtg gcatcctcag
 421 gaacattaga attcacagca gagggattca catggacagg tgtcactcaa aacggaagaa
 481 gtggagcctg caaaagggga tcagccgata gtttctttag ccgactgaat tggctaacaa
```

-continued

```
 541 aatctggaaa ttcttacccc acattgaatg tgacaatgcc taacaataac aatttcgata 601 agctatacat ctgggggatc catcacccga gctcaaacaa tgagcagaca aaattgtata 661 tccaagaatc aggacgagta acagtctcaa caaaaagaag tcaacaaaca ataatcccca 721 acatcggatc tagaccgtgg gtcaggggtc aatcaggcag ataagcata tattggacca 781 ttgtgaaacc tggagatatc ctaataataa acagtaatgg caacttagtt gcaccgcggg 841 gatatttcaa attgcgaaca gggaaaagct ctgtaatgag atcagatgca cccatagaca 901 cttgtgtgtc tgaatgtatt acaccaaatg gaagcatccc caacgacaaa ccatttcaaa 961 atgtgaacaa agttacatat ggaaaatgcc ccaagtatat caggcaaaac actttgaagc 1021 tggccactgg gatgaggaat gtaccagaaa agcaaatcag aggaatcttt ggagcaatag 1081 cgggattcat agaaaacggc tgggaaggaa tggttgatgg gtggtatgga ttccgatatc 1141 aaaactcgga aggaacagga caagctggag atctaaagag cactcaagca gccatcgacc 1201 agatcaatgg aaaattgaac agagtgattg aaaggaccaa tgagaaattc catcaaatag 1261 agaaggaatt ctcagaagta gaagggagaa tccaggactt ggagaagtat gtagaagaca 1321 ccaaaataga cctatggtcc tacaatgcag agttgctggt ggctctagaa aatcaacata 1381 caattgactt aacagatgca gaaatgaata aactattcga gaagactagg cgccagttaa 1441 gagaaaacgc ggaagacatg ggaggtggat gtttcaagat ttatcacaaa tgtgataatg 1501 catgcattgg atcaataaga aatgggacat atgaccatta catatacaga gatgaagcat 1561 taaacaaccg atttcaaatt aaaggtgtag agctgaaatc aggctacaaa gattggatac 1621 tgtggatttc attcgccata tcatgcttct taatttgcgt tgttctattg ggtttcatta 1681 tgtgggcttg ccaaaaaggc aacatcagat gcaacatttg catttgagta aactgatagt 1741 taaaaacacc cttgtttcta ct
ks
```

EXAMPLE 5

Newmarket Equine Influenza Nucleotide Sequences

DEFINITION Influenza A virus (A/equine 2/Suffolk/89 (H3N8)) NS1 gene.

```
ACCESSION X80060; SEQ ID NO: 37
  1 atggattcca acactgtgtc aagctttcag gtagactgtt ttctttggca tgtccgcaaa 61 cgatttgcag accaagaact gggtgatgcc ccattccttg accggcttcg ccgagaccag 121 aagtccctaa aaggaagagg tagcactctt ggtctggaca tcgaaacagc cactcgtgca 181 ggaaagcaga tagtggagca gattctggaa gaggaatcag atgaggcatt taaaatgacc 241 attgcctctg ttcctgcttc acgctactta actgacatga ctcttgatga gatgtcaaga 301 gactggttca tgctcatgcc caagcagaaa gtaacaggct ccctatgtat aagaatggac 361 caggcaatca tggataagaa catcatactt aaagcaaact ttagtgtgat tttcgaaagg 421 ctggagacac taatactact cagggccttc accgaagaag gagcagtcgt tggcgaaatt 481 tcaccattgc cttctcttcc aggacatact aatgaggatg tcaaaaatgc aattggggtc 541 ctcatcggag gacttaaatg gaatgataat acggttagag tctctgaaac tctacagaga 601 ttcgcttgga gaagcagtca tgagaatggg agaccttcat tccctccaaa gcagaaacga 661 aaaatggaga gaacaattga gtcagaagtt tga
```

DEFINITION Influenza A virus (A/eq/Newmarket/93/ (H3N8)) HA1 gene for HAY subunit of haemagglutinin, genomic RNA.

```
ACCESSION X85089; SEQ ID NO: 38
   1 atgaagacaa ccattatttt gatactactg acccattggg tctacagtca aacccaacc
  61 agtggcaaca acacagccac attatgtctg ggacaccatg cagtagcaaa tggaacattg
 121 gtaaaaacaa taactgatga ccaaattgag gtgacaaatg ctactgaatt agtccagagc
 181 atttcaatag ggaaaatatg caacaactca tatagggttc tagatggaag aaattgcaca
 241 ttaatagatg caatgctagg agaccccat tgtgatgatt ttcagtatga aattgggac
 301 ctcttcatag aaagaagcag cgctttcagc aattgctacc catatgacat ccctgactat
 361 gcatcgctcc ggtccattgt agcatcctca ggaacattag aattcacagc agagggttc
 421 acatggacag tgtcactca aaacggagga agtggagcct gcaaaagggg atcagccgat
 481 agtttcttta gccgactgaa ttggctaaca aaatctggaa attcttaccc catattgaat
 541 gtgacaatgc ctaacaataa aaatttcgat aaactataca tctggggat tcatcacccg
 601 agctcaaaca aagagcagac aaaattatat atccaagaat caggacgagt aacagtctca
 661 acagaaagaa gtcaacaaac agtaatccct aacatcggat ctaggccgtg ggtcaggggt
 721 caatcaggca ggataagcat atactggacc attgtaaaac ctggagatat tctaatgata
 781 aacagtaatg caacttagt tgcaccgcgg ggatatttta aattgagaac agggaaaagc
 841 tctgtaatga gatcagatgc actcatagac acttgtgtgt ctgaatgtat tacaccaaat
 901 ggaagcatcc ccaacgacaa accatttcaa aatgtgaaca aaattacata tggaaaatgc
 961 cccaagtata tcaggcaaaa cactttaaag ctggccactg ggatgaggaa tgtaccagaa
1021 aagcaaatca ga
```

DEFINITION Influenza A virus (A/eq/Newmarket/93/ (H3N8)) HA1 gene for HAY subunit of haemagglutinin, genomic RNA.

```
ACCESSION X85088; SEQ ID NO: 39
   1 atgaagacaa ccattatttt gatactactg acccattggg tctacagtca aacccaacc
  61 agtggcaaca acacagccac attatgtctg ggacaccatg cagtagcaaa tggaacattg
 121 gtaaaaacaa taactgatga ccaaattgag gtgacaaatg ctactgaatt agttcagagc
 181 atttcaatag ggaaaatatg caacaactca tatagagttc tagatggaag aaattgcaca
 241 ttaatagatg caatgctagg agaccccac tgtgatgtct ttcagtatga aattgggac
 301 ctcttcatag aaagaagcag cgctttcagc aattgctacc catatgacat ccctgactat
 361 gcatcgctcc ggtccattgt agcatcctca ggaacattgg aattcacagc agagggattc
 421 acatggacag tgtcactca aaacggaaga agtggagcct gcaaaagggg atcagccgat
 481 agtttcttta gccgactgaa ttggctaaca aaatctggaa actcttaccc cacattgaat
 541 gtgacaatgc ctaacaataa aaatttcgac aaactataca tctggggat tcatcacccg
 601 agctcaaacc aacagcagac agaattgtac atccaagaat caggacgagt aacagtctca
 661 acaaaaagaa gtcaacaaac gataatccct aatatcggat ctagaccatg ggtcaggggt
 721 caatcaggca ggataagcat atactggacc attgtaaaac ctggagatat cctaatgata
 781 aacagtaatg caacttagt tgcaccgcgg ggatatttta aattgaaaac agggaaaagc
 841 tctgtaatga gatcagatgc acccatagac atttgtgtgt ctgaatgtat tacaccaaat
```

-continued

```
 901 ggaagcatcc ccaacgacaa accatttcaa aatgtgaaca aagttacata tggaaaatgc
 961 cccaagtata tcaggcaaaa cactttaaag ctggccactg ggatgaggaa tgtaccagaa
1021 aagcaaatca ga
```

DEFINITION Influenza A virus (A/eq/Sussex/89/(H3N8)) HAI gene for HAY subunit of haemagglutinin, genomic RNA.

```
ACCESSION X85090; SEQ ID NO: 40
   1 atgaagacaa ccattatttt gatactactg acccattggg tctacagtca aacccaacc
  61 agtggcaaca acacagccac attatgtctg ggacaccatg cagtagcaaa tggaacattg
 121 gtaaaaacaa taactgatga ccaaattgag gtgacaaatg ctactgaatt agttcagagc
 181 atttcaatag ggaaaatatg caacaactca tatagggttc tagatggaag aaattgcaca
 241 ttaatagatg caatgctagg agaccccac tgtgatgttt ttcagtatga aattgggac
 301 ctcttcatag aaagaagcag cgctttcagc aattgctacc catatgacat ccctgactat
 361 gcatcgctcc ggtccattgt agcatcctca ggaacattag aattcacagc agagggattc
 421 acatggacag gtgtcactca aaacggaaga agtggagcct gcaaaagggg atcagccgat
 481 agtttcttta gccgactgaa ttggctaaca aaatctggaa attcttaccc catattgaat
 541 gtgacaatgc ctaacaataa aaatttcgat aaactataca tctgggggat tcatcacccg
 601 agctcaaaca aagagcagac aaaattgtat atccaagaat caggacgagt aacagtctca
 661 acagaaagaa gtcaacaaac agtaatccct aacatcggat ctagaccgtg ggtcaggggt
 721 caatcaggca ggataagcat atactggacc attgtaaaac ctggagatat tctaatgata
 781 aacagtaatg caacttagt tgcaccgcgg ggatatttta aattgagaac agggaaaagc
 841 tctgtaatga gatcagatgc actcataggc acttgtgtgt ctgaatgtat tacaccaaat
 901 ggaagcatcc ccaacgacaa accatttcaa aatgtgaaca aagttacata tggaaaatgc
 961 cccaagtata tcaggcaaaa cactttaaag ctggccactg ggatgaggaa tgtaccagaa
1021 aagcaaatca ga
```

DEFINITION Influenza A virus (A/eq/Lambourn/92/(H3N8)) HAI gene for HAY subunit of haemagglutinin, genomic RNA.

```
ACCESSION X85087; SEQ ID NO: 41
   1 atgaagacaa ccattatttt gatactactg acccattggg tctacagtca aacccaacc
  61 agtggcaaca acacagccac attatgtctg ggacaccatg cagtagcaaa tggaacattg
 121 gtaaaaacaa taactgatga ccaaattgag gtgacaaatg ctactgaatt agttcagagc
 181 atttcaatag ggaaaatatg caacaactca tatagggttc tagatggaag aaattgcaca
 241 ttaatagatg caatgctagg agaccccat tgtgatgatt ttcagtatga aattgggac
 301 ctcttcatag aaagaagcag tgctttcagc aattgctacc catatggcat ccctgactat
 361 gcatcgctcc ggtccattgt agcatcctca ggaacattag aattcacagc agagggttc
 421 acatggacag gtgtcactca aaacggaaga agtggagcct gcaaaagggg atcagccgat
 481 agtttcttta gccgactcaa ttggctaaca aaatctggaa attcttaccc catattgaat
 541 gtgacaatgc ctaacaataa aaatttcgat aaactataca tctgggggat tcatcacccg
```

-continued

```
 601 agctcaaaca aagagcagac aaaattatat atccaagaat caggacgagt aacagtctca
 661 acagaaagaa gtcaacaaac agtaatccct aacatcggat ctaggccgtg ggtcaggggt
 721 caatcaggca ggataagcat atactggacc attgtaaaac ctggagatat tctaatgata
 781 aacaataatg gcaacttagt tgcaccgcgg ggatatttta aattgagaac agggaaaagc
 841 tctgtaatga gatcagatgc actcatagac acttgtgtgt ctgaatgtat tacaccaaat
 901 ggaagcatcc ccaacgacaa accatttcaa aatgtgaaca aagttacata tggaaaatgc
 961 cccaagtata tcaggcaaaa cactttaaag ctggccactg ggatgaggaa tataccagaa
1021 aagcaaatca ga
```

DEFINITION Influenza A virus (A/eq/Ella/89/(H3N8)) HAI gene for HAY subunit of haemagglutinin, genomic RNA.

```
ACCESSION X85086; SEQ ID NO: 42
   1 atgaagacaa ccattatttt gatactactg acccattggg tctacagtca aaacccaacc
  61 agtggcaaca acacagccac attatgtctg ggacaccatg cagtagcaaa tggaacattg
 121 gtaaaaacaa taactgatga ccaaattgag gtgacaaatg ctactgaatt agttcagagc
 181 atttcaatag ggaaaatatg caacaactca tatagggttc tagatggaag aaattgcaca
 241 ttaatagatg caatgctagg agaccccac tgtgatgttt ttcagtatga gaattgggac
 301 ctcttcatag aaagaagcag cgctttcagc aattgctacc catatgacat ctctgactat
 361 gcatcgctcc ggtccattgt agcatcctca ggaacattag aattcacagc agagggattc
 421 acatggacag gtgtcactca aaacggaaga agtggagcct gcaaaagggg atcagccgat
 481 agtttcttta gccgactgaa ttggctaaca aaatctggaa attcttaccc catattgaat
 541 gtgacaatgc ctaacaataa aaatttcgat aaactataca tctggggggat tcatcacccg
 601 agctcaaaca aagagcagac aaaattgtat atccaagaat caggacgagt aacagtctca
 661 acagaaagaa gtcaacaaac agtaatccct aacatcggat ctagaccgtg ggtcaggggt
 721 caatcaggca ggataagcat atactggacc attgtaaaac ctggagatat tctaatgata
 781 aacagtaatg gcaacttagt tgcaccgcgg ggatatttta aattgagaac agggaaaagc
 841 tctgtaatga gatcagatgc acccataggc acttgtgtgt ctgaatgtat tacaccaaat
 901 ggaagcatcc ccaacgacaa accatttcaa aatgtgaaca aagttacata tggaaaatgc
 961 cccaagtata tcaggcaaaa cactttaaag ctggccactg ggatgaggaa tgtaccagaa
1021 aagcaaatca ga
```

DEFINITION Influenza A virus (A/eq/Arundel/91/(H3N8)) HAI gene for HAY subunit of haemagglutinin, genomic RNA.

```
ACCESSION X85085; SEQ ID NO: 43
   1 atgaagacaa ccattatttt gatactactg acccattggg tctacagtca aaacccaacc
  61 agtggcaaca acacagccac attatgtctg ggacaccatg cagtagcaaa tggaacattg
 121 gtaaaaacaa taactgatga ccaaattgag gtgacaaatg ctactgaatt agttcagagc
 181 atttcaatag ggaaaatatg caacaactca tatagagttc tagatggaag aaattgcaca
 241 ttaatagatg caatgctagg agaccccac tgtgatgtct ttcagtatga gaattgggac
```

-continued

```
 301 ctcttcatag aaagaagcag cgctttcagc aattgctacc catatgacat ccctgactat
 361 gcatcgctcc ggtccattgt agcatcctca ggaacattag aattcacagc agagggattc
 421 acatggacag tgtcactca aaacggaaga agtggagcct gcaaaagggg atcagccgat
 481 agtttcttta gccgactgaa ttggctaaca aatctggaa attcttaccc catattgaat
 541 gtgacaatgc taacaataa aaatttcgat aaactataca tctggggat tcatcacccg
 601 agctcaaaca aagagcagac aaaattgtac atccaagaat caggacgagt aacagtctca
 661 acaaaaagaa gtcaacaaac aataatccct aacatcggat ctagaccgtg ggtcaggggt
 721 caatcaggca ggataagcat atactggacc attgtaaaac ctggagatat cctaatgata
 781 aacagtaatg gcaacttagt tgcaccgcgg ggatatttta aattgagaac agggaaaagc
 841 tctgtaatga gatcagatgc acccatagac atttgtgtgt ctgaatgtat tacaccaaat
 901 ggaagcatcc ccagcgacaa accatttcaa aatgtaaaca aagttacata tggaaaatgc
 961 cccaagtata tcaggcaaaa cactttaaag ctggccactg ggatgaggaa tgtaccagaa
1021 aagcaaatca ga
```

DEFINITION Influenza A virus (A/equine/Suffolk/89 (H3N8)) HA gene for haemagglutinin.

```
ACCESSION X68437; SEQ ID NO: 44
    1 ctgtcaatca tgaagacaac cattattttg atactactga cccattgggt ctacagtcaa
   61 aacccaacca gtggcaacaa cacagccaca ttatgtctgg acaccatgc agtagcaaat
  121 ggaacattgg taaaaacaat aactgatgac caaattgagg tgacaaatgc tactgaatta
  181 gttcagagca tttcaatagg gaaaatatgc aacaactcat atagggttct agatggaaga
  241 aattgcacat aatagatgc aatgctagga ccccccact gtgatgtttt tcagtatgag
  301 aattgggacc tcttcataga aagaagcagc gctttcagca attgctaccc atatgacatc
  361 cctgactatg catcgctccg gtccattgta gcatcctcag gaacattaga attcacagca
  421 gagggattca catggacagg tgtcactcaa aacggaagaa gtggagcctg caaaggggga
  481 tcagccgata gtttctttag ccgactgaat tggctaacaa atctggaaa ttcttacccc
  541 atattgaatg tgacaatgcc taacaataaa aatttcgata aactatacat ctgggggatt
  601 catcacccga gctcaaacaa agagcagaca aaattgtata tccaagaatc aggacgagta
  661 acagtctcaa cagaaagaag tcaacaaaca gtaatcccta acatcggatc tagaccgtgg
  721 gtcaggggtc aatcaggcag gataagcata tactggacca ttgtaaaacc tggagatatt
  781 ctaacgataa acagtaatgg caacttagtt gcaccgcggg gatattttaa attgagaaca
  841 gggaaaagct ctgtaatgag atcagatgca cccatagaca cttgtgtgtc tgaatgtatt
  901 acaccaaatg gaagcatccc caacgacaaa ccatttcaaa atgtgaacaa agttacatat
  961 ggaaaatgcc ccaagtatat caggcaaaac actttaaagc tggccaccgg gatgaggaat
 1021 gtaccagaaa agcaaatcag aggaatcttt ggagcaatag cgggattcat agaaaacggc
 1081 tgggaaggaa tggttgatgg gtggtatgga ttccgatatc aaaactcgga aggaacagga
 1141 caagctgcag atctaaagag cactcaagca gccatcgacc agatcaatgg aaaattaaac
 1201 agagtgattg aaaggaccaa tgagaaattc catcaaatag agaaggaatt ctcagaagta
 1261 gaagggagaa tccaggattt ggagaagtat gtagaagaca ccaaaataga cctatggtcc
 1321 tacaatgcag aattgctggt ggctctagaa aatcaacata caattgactt aacagatgca
```

-continued

```
1381 gaaatgaata aattattcga gaagactagg cgccagttaa gagaaaacgc ggaagacatg 1441 ggaggtggat gtttcaagat ttaccacaaa tgtgataatg catgcattgg atcaataaga 1501 aatgggacat atgaccatta catatacaga gatgaagcat aaacaaccg atttcaaatc 1561 aaaggtgttg agttgaaatc aggctacaaa gattggatac tgtggatttc attcgccata 1621 tcatgcttct taatttgcgt tgttctattg ggtttcatta tgtgggcttg ccaaaaaggc 1681 aacatcagat gcaacatttg catttgagta aactgatagt taaaaacacc cttgtttcta 1741 ct
```

DEFINITION Influenza A virus (A/equine/Newmarket/1/77
(H7N7)) gene for haemagglutinin.

```
ACCESSION X62554; SEQ ID NO: 45
   1 nnnnnnnnnn nnnnnnnnna aatgaacact cagattctaa tattagccat ttcggcattc 61 ctctgtgtac gtgcagataa aatctgccta ggacatcatg ctgtgtctaa tggaaccaaa 121 gtagacaccc ttactgaaaa gggaatagaa gtcgtcaatg caacagaaac agttgaacaa 181 aaaacatcc ccaagatctg ctcaaaaggg aaacagacta ttgaccttgg tcaatgtgga 241 ttactaggga ccactattgg tccccccaa tgcgaccaat tcttgaatt ctctgctaat 301 ttaataattg agagaagaga aggtgatgat atttgttatc caggcaaatt tgacaatgaa 361 gaaacattga cacaaatact cagaaaatcc ggaggaatta aaaggagaa tatgggattc 421 acatataccg gagtgagaac caatggagag actagcgcct gtagaaggtc aagatcttcc 481 ttttatgcag aaatgaaatg gctcctatct aacacagaca tggggtatt cccacaaatg 541 acaaaatcct acaagaacac taagaaggag ccagctctga atctgggg aatccaccac 601 tcaggatcaa ctgctgaaca gactagattg tatggaagtg aaacaagtt gataacagtt 661 tggagttcca ataccaaca atctttttgcc ccaaaccctg gaccaaggcc gcaaatgaat 721 ggccaatcag gaagaattga cttttactgg ctgatgttag atcccaatga tactgttaat 781 ttcagttttta atggggcctt tatagcacct gaccgcgcca gttttctaag aggtaaatct 841 ctaggaattc agagtgacgc acaacttgac aacaattgtg aaggtgaatg ttatcatatt 901 ggaggtacca taattagcaa cttgcccttt caaaacatta tagcagagc aattgggaaa 961 tgccccagat acgtaaagca aaaaagctta atgctagcaa ccggaatgaa aaatgttcct 1021 gaaaattcta cacacaaaca gttaactcat cacatgcgca aaaaagagg tttatttggt 1081 gcaatagcag gatttattga aaatggatgg gaaggattaa tagatggatg gtatggatac 1141 agacatcaga atgcacaagg agaaggaact gctgcagact acaaaagtac acaatctgct 1201 gtcaatcaaa taaccgggaa attaaacaga ctaatagaaa aaaccaacca gcaatttgaa 1261 ctaatagata tgaattcaa tgaaatagaa agcaaattg gcaatgttat taactggact 1321 agagattcta tcatcgaaat atggtcatat aatgcagaat tcctcgtggc agtggagaat 1381 caacacacta ttgatttaac tgattcagag atgaacaaat tatgtgaaaa ggtaagaaga 1441 cagctgagag aaaatgctga ggaagatggt aatggctgtt ttgaaatatt tcaccaatgt 1501 gacaatgatt gcatggccag cattagaaac aatacatat atcataaaaa atacagaaag 1561 gaggcaatac aaaacagaat tcagattgat gcagtaaagt tgagcagcgg ttacaaagaa
```

-continued

```
1621 ataatacttt ggtttagctt cggggcatca tgtttcttat ttcttgccat tgcaatggtt 1681 cttgctttca tatgcataaa aaatggaaac atgcggtgca ctatttgtat ataagtttga 1741 aaaaacaccc ttgtttctan n
```

DEFINITION Influenza A virus HA partial gene for haemagglutinin, genomic RNA, strain A/equine/Newmarket-Bob Champion/89(H3N8).

```
ACCESSION AJ223193; SEQ ID NO: 46
   1 agtcaaaacc caaccagtgg caacaacaca gccacattat gtctgggaca ccatgcagta 61 gcaaatggaa cattggtaaa acaataact gatgaccaaa ttgaggtgac aaatgctact 121 gaattagttc agagcatttc aatagggaaa atatgcaaca actcatatag ggttctagat 181 ggaagaaatt gcacattaat agatgcaatg ctaggagacc cccactgtga tgttttcag 241 tatgagaatt gggacctctt catagaaaga agcagcgctt tcagcaattg ctacccatat 301 gacatccctg actatgcatc gctccggtcc attgtagcat cctcaggaac attagaattc 361 acagcagagg gattcacatg gacaggtgtc actcaaaacg gaagaagtgg agcctgcaaa 421 aggggatcag ccgatagttt ctttagccga ctgaattggc taacaaaatc tggaaattct 481 taccccatat tgaatgtgac aatgcctaac aataaaaatt tcgataaact atacatctgg 541 gggattcatc acccgagctc aaacaaagag cagacaaaat tgtatatcca agaatcagga 601 cgagtaacag tctcaacaga aagaagtcaa caaacagtaa tccctaacat cggatctaga 661 ccgtgggtca ggggtcaatc aggcaggata agcatatact ggaccattgt aaaacctgga 721 gatattctaa tgataaacag taatggcaac ttagttgctc cgcggggata ttttaaattg 781 agaacaggga aaagctctgt aatgagatca gatgcaccca tagacacttg tgtgtctgaa 841 tgtattacac caaatggaag catccccaac gacaaaccat ttcaaaatgt gaacaaagtt 901 acatatggaa aatgccccaa gtatatcagg caaaacactt taaagctggc cactgggatg 961 aggaatgtac cagaaaagca aatcagagga atctttggag caatagaggg attcatagaa 1021 aacggctggg aaggaatggt tgatgggtgg tatggattcc gatatcaaaa ctcggaagga 1081 acaggacaag ctgcag
```

DEFINITION Influenza A virus (A/Equine/NewMarket/D64/79(H3N8)) gene for hemagglutinin precursor, partial cds.

```
ACCESSION D30677; SEQ ID NO: 47
   1 ctgtcaatca tgaagacaac cattattttg atactactga cccattgggt ctacagtcaa 61 aacccaacca gtggcaacaa cacagccaca ctatgtctgg acaccatgc agtagcaaat 121 ggaacattgg taaaacaat aactgatgac caaattgagg tgacaaatgc cactgaatta 181 gttcagagca cttcaatagg gaaaatatgc aacaacccat atagggttct agatggaaga 241 aactgcacat taatagatgc aatgctagga tcccccact gtgatgtttt tcagtatgag 301 aattgggacc tcttcataga aagaagcagc gctttcagca attgctaccc atatgacatc 361 cctgactatg catcgctccg gtctattgtg gcatcttcag gaacattaga attcacagca 421 gagggattca catggacagg tgtcactcaa aacggaagag tggcgcctg cagaagggga 481 tcagccgata gtttctttag ccgactgaat tggctaacaa aatctggaga ttcttacccc
```

-continued

```
 541 acattgaatg tgacaatgcc taacaataac aatttcgata aactatacat ctgggggatc
 601 catcacccga gcacaaacaa tgagcagaca aaattgtatg tccaagaatc agggcgagta
 661 acagtctcaa caaaaagaag tcaacaaaca ataatcccca acatcggatc tagaccgtgg
 721 gtcaggggtc aaccaggcag ataagcata tattggacca ttgtgaaacc tggagatatc
 781 ctaatgataa acgtaatgg caacttagtt gcaccgcggg gatatttcaa aatgcgaaca
 841 ggaaaaagct ctataatgag atcagatgca cccatagaca cttgtgtgtc cgagtgtatt
 901 acaccaaatg aagcatccc aacgacaaa ccatttcaaa atgtgaacaa agttacatat
 961 gggaaatgcc ccaagtatat caagcagaat actttgaagc tggccactgg gatgaggaat
1021 gtaccagaaa agcaaatcag aggaatcttt ggagcaatag cgggattcat agaaaatggc
1081 tgggag
```

DEFINITION Influenza A virus (A/eq/Newmarket/1/77 (H7N7)) matrix proteins M1 and M2 (M) gene, complete cds.

```
ACCESSION AF001686; SEQ ID NO: 48
  1 atgagtcttc tgaccgaggt cgaaacgtac gttctctcta tcgtaccatc aggcccctc
 61 aaagccgaga tcgcgcagag acttgaagat gtctttgcag gaaagaacac cgatcttgag
121 gcactcatgg aatggctaaa gacaagacca atcctgtcac ctctgactaa ggggatttta
181 ggatttgtgt tcacgctcac cgtgcccagt gagcgaggac tgcagcgtag acgctttgtc
241 caaaatgccc ttaatgggaa cggagatcca aacaacatgg acagagcagt aaaactgtac
301 aggaagctta aagggaaat aacattccat ggggcaaaag aggtggcact cagctattcc
361 actggtgcac tagccagctg catgggactc atatacaaca gaatggggac tgtgacaacc
421 gaagtggcat ttggcctggt atgcgccaca tgtgaacaga ttgctgattc ccagcaccga
481 tctcacagac agatggtgac aacaaccaac ccactaatca gacacgagaa cagaatggta
541 ctagccagta ccacagctaa agccatggag cagatggcag ggtcgagtga gcaggcagca
601 gaggccatgg aggttgctag tcaggccagg cagatggtgc aggcaatgag aaccattggg
661 acccacccta gctccagtgc cggtttgaaa atgatcttc ttgaaaattt gcaggcctac
721 cagaaacgga tgggagtgca aatgcagcga ttcaagtgat cctctcgtta ttgcagcaag
781 tatcattggg atcttgcact tgatattgtg gattcttgat cgtcttttct tcaaatgcat
841 ttatcgtcgt cttaaatacg gtttgaaaag agggccttct acggaaggag tacctgagtc
901 tatgagggaa gaatatcggc aggaacagca gagtgctgtg gatgttgacg atggtcattt
961 tgtcaacata gagctggagt aa
```

DEFINITION Influenza A virus (A/eq/Newmarket/79 (H3N8)) matrix proteins M1 and M2 (M) gene, complete cds.

```
ACCESSION AF001675; SEQ ID NO: 49
  1 atgagtcttc taaccgaggt cgaaacgtac gttctctcta tcgtaccatc aggcccctc
 61 aaagccgaga tcgcgcagag acttgaagat gtctttgcag ggaagaacac cgatcttgag
121 gcactcatgg aatggctaaa gacaagacca atcctgtcac ctctgactaa agggatttta
181 ggatttgtgt tcacgctcac cgtgcccagt gagcgaggac tgcagcgtag acgctttgtc
241 caaaatgccc ttagtggaaa cggagatcca aacaacatgg acagagcagt aaaactgtac
```

-continued

```
301 aggaagctta aaagagaaat aacattccat ggggcaaaag aggtggcact cagctattcc 361 actggtgcac tagccagctg catgggactc atatacaaca gaatggggac tgtgacaacc 421 gaagtggcat ttggcctggt atgcgccaca tgtgaacaga ttgctgattc ccagcatcga 481 tctcacaggc agatggtgac aacaaccaac ccactaatca gacatgaaaa cagaatggta 541 ctagccagta ccacagctaa agccatggag cagatggcag ggtcgagtga gcaggcagca 601 gaggccatgg aggttgctag taaggccagg cagatggtac aggcaatgag gaccattggg 661 acccacccta gctccagtgc cggtttgaaa gatgatcttc ttgaaaattt gcaggcctac 721 cagaaacgga tgggagtgca aatgcagcga ttcaagtgat cctctcgtta ttgcagcaag 781 tatcattggg atcttgcact tgatattgtg gattcttgat cgccttttct tcaaattcat 841 ttatcgtcgc cttaaatacg gtttgaaaag agggccttct acggaaggag tacctgagtc 901 tatgagggaa gaatatcggc aggaacagca gaatgctgtg gatgttgacg atggtcattt 961 tgtcaacata gagctggagt aa
```

DEFINITION Influenza A virus (A/eq/Newmarket/1/77 (H7N7)) nonstructural proteins NS1 and NS2 (NS) gene, complete cds.

ACCESSION AF001663; SEQ ID NO: 50

```
  1 atggattcca acactgtgtc aagctttcag gtagactgtt ttctttggca tgtccgcaaa
 61 cgatttgcag accaagaact gggtgatgcc ccattccttg accggcttcg ccgagaccag
121 aagtccctaa aaggaagagg cagcactctt ggtctggaca tcgaaacagc cactcatgca
181 ggaaagcaga tagtggagcg aattctggaa gaggaatcag atgaggcact taaaatgacc
241 atagcctctg ttcctacttc acgctactta actgacatga ctcttgatga gatgtcaaga
301 gactggttca tgctcatgcc caagcagaaa gtaacaggct ccctatgtat aaggatggac
361 caagcaatca tggataagaa catcatacta aaagcaaact ttagtgtgat tttcgaaagg
421 ctggagacac taatactact tagagctttc accgaagaag gagcagtcgt tggcgaaatt
481 tcaccattgc cttctcttcc aggacatact aatgaggatg tcaaaaatgc aattggggtc
541 ctcatcggag gacttaaatg gaatgataac acagttagag tctctgaaac tctacagaga
601 ttcgcttgga gaagcagtca tgagaatggg agaccttcat tccctccaaa gcagaaacga
661 aaaatggcga gaacaattga gtcagaagtt tgaagaaata aggtggttga ttgaagaagt
721 gagacataga ttgaaaaata cagaaaatag ttttgaacaa ataacattta tgcaagcctt
781 acaactattg cttgaagtag aacaagagat aagaactttc tcgtttcagc ttatttaa
```

DEFINITION Influenza A virus (A/eq/Newmarket/D63/79 (H3N8)) nonstructural proteins NS1 and NS2 (NS) gene, complete cds.

ACCESSION AF001662; SEQ ID NO: 51

```
  1 atggattcca acactgtgtc aagctttcag gtagactgtt ttctttggca tgtccgcaaa
 61 cgatttgcag accaagaact gggtgatgcc ccattccttg accggcttcg ccgagaccag
121 aagtccctaa aaggaagagg cagcactctt ggtctggaca tcgaaacagc cactcgtgca
181 ggaaagcaga tagtggagcg gattctggaa gaggagtcag atgaggcact taaaatgacc
241 attgcctctg ttcctgcttc acgctactta actgacatga ctcttgatga gatgtcaaga
```

```
                                      -continued
301 gactggttca tgctcatgcc caagcagaaa gtaacaggct ccctatgtat aaggatggac 361 caggcaatca tggataagaa catcatacta aaagcaaact ttagtgtgat tttcgaaagg 421 ctggagacac taatactact tagagccttc accgaagaag gagcagtcgt tggcgaaatt 481 tcaccattgc cttctcttcc aggacatact aatgaggatg tcaaaaatgc aattggggtc 541 ctcatcggag gacttaaatg gaatgataat acagttagag tctctgaaac tctacagaga 601 ttcgcttgga gaagcagtca tgaatgggg agaccttcat tccctccaaa gcagaaacga 661 aaaatggcga gaacaattga gccagaagtt tgaagaaata agatggttga ttgaagaagt 721 gcgacataga ttgaaaaata cagaaaatag tttttgaacaa ataacattta tgcaagcctt 781 acaactattg cttgaagtag aacaagagat aagaactttc tcgtttcagc ttatttaa
```

EXAMPLE 6

Efficacy of Inactivated Influenza Virus Vaccine in Canines

Vaccine active ingredient (AI) is produced either in 9-11 day-old embryonated chicken eggs or in continuous cell cultures such as MDCK cells.

Egg Production, Harvest and Purification. Vaccine AI production in embryonating chicken eggs is prepared by inoculation 0.1-0.25 ml of virus suspension containing 100-1000 EID50 (egg infectious dose) into the allantoic cavity. Allantoic fluid is harvested after incubation at 33-37° C. for 2-6 days and pooled. The virus pool is clarified by centrifugation at 1500-4000 g for 5-15 minutes and filtered through a 20 μm filter (1). The virus maybe concentrated by ultra-filtration using a 300 KDa membrane with a maximum concentration factor of 20 (2).

Further the concentrated virus is optionally purified by zonal ultra-centrifugation on a sucrose gradient followed by filtration of the virus containing fraction through a 0.5 μm membrane. This step can be repeated. The virus containing fraction is diluted in a suitable buffer such as a phosphate buffer (3).

Further purification consists of treatment with Tween/ether at 0.1% final concentration (w/v)) and 50% final concentration (w/w), respectively. The resulting solution is centrifuged and the aqueous phase is collected. This step can be repeated. The aqueous phase is treated with nitrogen to remove residual ether (4).

Cell Culture Production, Harvest and Purification. Active ingredient is prepared in cells (e.g. MDCK, BHK, PerC6 cells) by inoculation at a rate of MOI of 0.001-1 TCID50. Culture is harvested after incubation at 35-37 C. for 48-96 hrs when cytopathic effect (CPE) is approximately 50-90%. Culture is sonicated and centrifuged at 1500-4000 g for 5-15 minutes (1). The virus is concentrated by ultra-filtration using a 300 KD membrane with a max. concentration factor of 20 (2).

The virus is optionally purified by exclusion chromatography (Sepharose 6 fast flow)(3).

Inactivation. Virus (fraction 1, 2, 3 or 4) are inactivated by addition of formalin or beta-propiolactone to a final concentration of 0.05% (w/v) or 0.01% (w/v), respectively and the suspension is held respectively at 5° C. for 16-18 hours or at 20° C. for 25-36 hours with continuous agitation.

Active ingredient inactivation is confirmed by inoculation into embryonated chicken eggs or onto MDCK cells.

Preparation of Final Vaccine. Vaccine consists of the inactivated influenza virus and an adjuvant such as aluminium hydroxide, aluminum phosphate, Carbomer or oil-in-water emulsion, which may contain other immunostimulating components such as CpG (1-100 ug/dose). Vaccine typically contains 15-50 μg of hemagglutinin measured by single radial-immunodiffusion (SRD) or >400 haemagglutination Units The vaccine is administered either by subcutaneous or intramuscular route. Two doses are administered at an interval of 2-5 weeks to pups from 4 weeks of age. Duration of immunity: 6-12 months after a primary vaccination course.

Vaccination/Challenge Protocol. Dogs (less than 4 weeks old) are vaccinated with 2 doses of inactivated vaccine at 3-4 weeks interval via the subcutaneous route. Blood samples are collected on the day of the first and second vaccination and 2-4 weeks after second vaccination to determine the levels of anti-influenza virus specific antibodies using virus neutralization, hemagglutination inhibition, ELISA or Single Radial Heamolysis (SRH) tests.

Two to 4 weeks after $2^{nd}$ immunization dogs are challenged with a virulent strain of influenza H3N8 to determine efficacy of the vaccines.

Vaccinated and control dogs are challenged by the following route:

By spray: animals are placed into an enclosed container or a mask is placed on the nose of the dogs and the virus suspension is aerosolized to generate 1-100 μM droplets. Animals are kept in the aerosolization chambers for 30 minutes to allow inhalation of the aerosol.

Alternativelly thy can be challenged by one the following routes:

Intra-nasally: 0.5 ml containing $10^{5-8}$ EID50 of challenge virus is dropped to each nostril by the aid of dropper.

Intra-tracheally: 1-2 ml containing $10^{5-8}$ $EID_{50}$ virus is directly instilled into the trachea.

Orally: 5-10 ml containing $10^{5-8}$ EID50 of challenge virus is orally administered.

Animals are observed daily for 14 days following challenge for clinical signs including fever, cough, nasal, ocular discharge, respiratory distress, anorexia and lethargy. In addition, groups of animals are euthanized and evaluated for pathological findings of pulmonary and pleural hemorrhage, tracheitis, bronchitis, broncholilitis, and bronchopneumonia.

Tracheal swabs are collected from all animals post challenge days 1-14 for virus isolation.

Presence or absence of viral antigens in respiratory tissues is evaluated by immunohistochemistry on days 3, 7 and 10 post-challenge.

Blood samples are collected on days 7 and 14 post-challenge and are analyzed for the presence of anti-influenza H3N8 virus specific antibody.

The invention is further described by the following numbered paragraphs:

1. A method of eliciting an immune response against influenza in a canine, comprising administering a formulation comprising an avipox expression vector comprising a polynucleotide encoding an influenza antigen, epitope or immunogen and a pharmaceutically or veterinarily acceptable carrier, excipient or vehicle in an effective amount for eliciting an immune response.

2. A method of inducing an immune response against influenza in a canine, comprising administering a formulation comprising an avipox expression vector comprising a polynucleotide encoding an influenza antigen, epitope or immunogen and a pharmaceutically or veterinarily acceptable carrier, excipient or vehicle in an effective amount for inducing an immune response.

3. The method of paragraph 1 or 2, wherein the formulation further comprises an adjuvant.

4. The method of any one of paragraphs 1 to 3, wherein the influenza antigen, epitope or immunogen is a hemagglutinin, matrix protein, membrane protein, neuraminidase, nonstructural protein, nucleoprotein, polymerase or any fragment thereof.

5. The method of any one of paragraphs 1 to 4, wherein the influenza antigen, epitope or immunogen is isolated from a canine infected with influenza.

6. The method of paragraph 5 wherein the influenza antigen, epitope or immunogen is isolated from the broncho alveolar lavage and/or lung tissues of the canine.

7. The method of any one of paragraphs 1 to 4, wherein the influenza antigen, epitope or immunogen is isolated from an equine influenza.

8. The method of paragraph 7, wherein the equine influenza is an Ohio equine influenza, a Kentucky equine influenza or a Newmarket equine influenza.

9. The method of any one of paragraphs 1 to 8, wherein the avipox expression vector is an attenuated avipox expression vector.

10. The method of paragraph 9, wherein the avipox expression vector is a canarypox vector.

11. The method of paragraph 10, wherein the canarypox vector is ALVAC.

12. The method of paragraph 10 or 11, wherein the influenza antigen, epitope or immunogen is a hemagglutinin.

13. The method of paragraph 12, wherein the hemagglutinin is H3.

14. The method of paragraph 12 or 13, wherein the canarypox vector is CP1529 or CP1533.

15. A method of eliciting an immune response against influenza in a canine, comprising administering a formulation comprising an inactivated influenza vaccine and a pharmaceutically or veterinarily acceptable carrier, excipient or vehicle in an effective amount for eliciting an immune response.

16. A method of inducing an immune response against influenza in a canine, comprising administering a formulation comprising an inactivated influenza vaccine and a pharmaceutically or veterinarily acceptable carrier, excipient or vehicle in an effective amount for inducing an immune response.

17. The method of paragraph 15 or 16, wherein the formulation further comprises an adjuvant.

18. The method of any one of paragraph 15 to 17, wherein the inactivated influenza vaccine is an inactivated canine influenza.

19. The method of any one of paragraphs 15 to 17, wherein the inactivated influenza vaccine is an inactivated equine influenza.

20. The method of paragraph 19, wherein the equine influenza is an Ohio equine influenza, a Kentucky equine influenza or a Newmarket equine influenza.

21. The method of any one of paragraphs 15 to 20, wherein the inactivated influenza vaccine is inactivated with formalin or beta-propiolactone.

22. The method of any one of paragraphs 17 to 21, wherein the adjuvant is aluminum hydroxide, aluminum phosphate, a carbomer or an oil-water-emulsion.

23. The method of any one of paragraphs 17 to 22, wherein the adjuvant further comprises CpG.

24. The method of any one of paragraphs 15 to 23, wherein the administration is subcutaneous or intramuscular.

25. A kit for performing any one of the methods of paragraphs 1 to 24 comprising the vaccine of any one of paragraphs 1 to * and instructions for performing the method of any one of paragraphs 1 to 24.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting an immune response in a canine against an equine strain of influenza, comprising administering a composition comprising inactivated equine influenza serotype H3 and a pharmaceutically or veterinarily acceptable carrier, excipient or vehicle in an effective amount for eliciting the immune response.

2. The method of claim 1, wherein the composition further comprises an adjuvant.

3. The method of claim 1, wherein the equine influenza virus is selected from the group consisting of an Ohio equine influenza virus isolate, a Kentucky equine influenza virus isolate, a Newmarket equine influenza virus isolate or mixtures thereof.

4. The method of claim 2, wherein the equine influenza virus is selected from the group consisting of an Ohio equine influenza virus isolate, a Kentucky equine influenza virus isolate, a Newmarket equine influenza virus isolate or mixtures thereof.

5. The method of claim 3 wherein the equine influenza virus is Kentucky equine influenza virus.

6. The method of claim 4 wherein the equine influenza virus is Kentucky equine influenza virus.

7. The method of claim 3 wherein the equine influenza virus is Newmarket equine influenza virus.

8. The method of claim 4 wherein the equine influenza virus is Newmarket equine influenza virus.

9. The method of claim 3 wherein the equine influenza virus is Ohio equine influenza virus.

10. The method of claim 4 wherein the equine influenza virus is Ohio equine influenza virus.

11. The method of claim 2 wherein the adjuvant is aluminum hydroxide, aluminum phosphate, a carbomer, or an oil-water-emulsion, saponin or a combination thereof and optionally further comprises CpG.

12. The method of claim 4 wherein the adjuvant is aluminum hydroxide, aluminum phosphate, a carbomer, or an oil-water-emulsion, and optionally further comprises CpG.

13. The method of claim 6 wherein the adjuvant is aluminum hydroxide, aluminum phosphate, a carbomer, or an oil-water-emulsion, and optionally further comprises CpG.

14. The method of claim 8 wherein the adjuvant is aluminum hydroxide, aluminum phosphate, a carbomer, or an oil-water-emulsion, and optionally further comprises CpG.

15. The method of claim 10 wherein the adjuvant is aluminum hydroxide, aluminum phosphate, a carbomer, or an oil-water-emulsion, and optionally further comprises CpG.

16. The method of any one of claims 1-15 wherein the administering is subcutaneously or intramuscularly.

17. The method of any one of claims 1-15 wherein the equine influenza is inactivated with formalin, beta-propiolactone, ethylene-imine, Triton X-100, or Tween-ether.

18. The method of claim 17 wherein the administering is subcutaneously or intramuscularly.

* * * * *

UNITED STATES PATENT AND TRADEMARK OFFICE
CERTIFICATE OF CORRECTION

PATENT NO. : 7,425,336 B2  Page 1 of 1
APPLICATION NO. : 11/264622
DATED : September 16, 2008
INVENTOR(S) : Jules Maarten Minke, Kemal Karaca and Jiansheng Yao It is certified that error appears in the above-identified patent and that said Letters Patent is hereby corrected as shown below:

On the Title Page:

Item 73, please correct the assignee's name from "Mevial Limited" to --Merial Limited--.

Signed and Sealed this

Thirtieth Day of December, 2008

JON W. DUDAS
*Director of the United States Patent and Trademark Office*

SEQUENCE LISTING

```
<160> NUMBER OF SEQ ID NOS: 51

<210> SEQ ID NO 1
<211> LENGTH: 3959
<212> TYPE: DNA
<213> ORGANISM: Influenza A virus

<400> SEQUENCE: 1
gtattctaaa ctaggaatag atgaaattat gtgcaaagga gatacctta  gatatggatc      60 tgatttattt ggtttttcat aatcataatc taacaacatt ttcactatac tataccttct     120
tgcacaagtc gccattagta gtatagactt atactttgta accatagtat actttagcgc     180
gtcatcttct tcatctaaaa cagatttaca acaataatca tcgtcgtcat cttcatcttc     240
```

```
attaaagttt tcatattcaa taactttctt ttctaaaaca tcatctgaat caataaacat     300
agaacggtat agagcgttaa tctccattgt aaaatatact aacgcgttgc tcatgatgta     360
ctttttttc  attatttaga aattatgcat tttagatctt tataagcggc cgtgattaac     420
tagtcataaa acccgggat  cgattctaga ctcgagcggc cgccagtgtg atggatatct     480
gcagaattcg gctttggtcc ttactcaaat gcaaatgttg cacctgatgt tgcctttttg     540
gcaagcccac ataatgaaac ccaatagaac aacgcaaatt aagaagcatg atatggcgaa     600
tgaaatccac agtatccaat cttggtagcc tgatttcaac tcaacacttt tgatttgaaa     660
tcggttgttt aatgcttcat ctctgtatat gtaatggtca tatgtcccat tcttattga      720
tccaatgcat gcattatcac atttgtggta aatcttgaaa catccacctc ccatgtcttc     780
cgcgttttct cttaactggc gcctagtctt ctcgaataat ttattcattt ctgcatctgt     840
taagtcaatt gtatgttgat tttctagagc caccagcaat tctgcattgt aggaccatag     900
gtctattttg gtgtcttcta catacttctc caaatcctgg attctccctt ctacttctga     960
gaattccttt tctatttgat ggaatttctc attggtcctt tcaatcactc tgttaatttt    1020
tccattgatc tggtctatgg ctgcttgagt gctctttaga tctgcagctt gtcctgttcc    1080
ttccgagttt tgatatcgga atccatacca cccatcaacc attccttccc agccgttttc    1140
tatgaatccc gctattgctc caaagattcc tctgatttgc ttttctggta cattcctcat    1200
cccagtggcc agcttaaaag tgttttgcct gatatacttg gggcattttc catatgtaat    1260
tttgttcaca ttttgaaatg gtttgtcgtt ggggatgctt ccatttggtg taatacattc    1320
agacacacaa gtgtctatga gtgcatctga tctcattaca gagcttttcc ctgttctcaa    1380
tttaaaatat ccccgcggtg caactaagtt gccattactg tttatcatta gaatatctcc    1440
aggttttaca atggtccagt atatgcttat cctgcctgat tgaccctga  cccacggcct    1500
agatccgatg ttagggatta ctgtttgttg acttctttct gttgagactg ttactcgtcc    1560
tgattcttgg atatataatt ttgtctgctc tttgtttgag ctcgggtgat gaatccccca    1620
gatgtatagt ttatcgaaat ttttattgtt aggcattgtc acattcaata tggggtaaga    1680
atttccagat tttgttagcc aattcagtcg gctaaagaaa ctatcggctg atccccttt     1740
gcaggctcca cttcttccgt tttgagtgac acctgtccat gtgaacccct ctgctgtgaa    1800
ttctaatgtt cctgaggatg ctacaatgga ccggagcgat gcatagtcag ggatgtcata    1860
tgggtagcaa ttgctgaaag cgctgcttct ttctatgaag aggtcccaat tctcatactg    1920
aaaatcatca caatgggggt ctcctagcat tgcatctatt aatgtgcaat ttcttccatc    1980
tagaacccta tatgagttgt tgcatatttt ccctattgaa atgctctgga ctaattcagt    2040
agcatttgtc acctcaattt ggtcatcagt tattgttttt accaatgttc catttgctac    2100
tgcatggtgt cccagacata atgtggctgt gttgttgcca ctggttgggt ttgactgta     2160
gacccaatgg gtcagtagta tcaaaataat ggttgtcttc attacgatac aaacttaacg    2220
gatatcgcga taatgaaata atttatgatt atttctcgct ttcaatttaa cacaaccctc    2280
aagaaccttt gtatttattt tcacttttta agtatagaat aaagaagctc taattaatta    2340
acgagcagat agtctcgttc tcgccctgcc tgatgactaa ttaattaacc cggatccttt    2400
ttatagctaa ttagtcacgt accttgaga  gtaccacttc agctacctct tttgtgtctc    2460
agagtaactt tctttaatca attccaaaac agtatatgat tttccatttc tttcaaagat    2520
gtagtttaca tctgctccctt tgttgaaaag tagcctgagc acttcttttc taccatgaat   2580
```

-continued

```
tacagctggc aagatcaatt tttcccagtt ctggacattt tatttttttt aagtagtgtg   2640
ctacatattt caatatttcc agattgtaca gcgatcatta aaggagtacg tcccatgtta   2700
tccagcaagt cagtatcagc acctttgttc aatagaagtt taaccattgt taaattttta   2760
tttgatacgg ctatatgtag aggagttaac cgatccgtgt ttgaaatatc tacatccgcc   2820
gaatgagcca atagaagttt aaccaaatta actttgttaa ggtaagctgc caaacacaaa   2880
ggagtaaagc ctccgctgta aagaacattg tttacatagt tattcttcaa cagatctttc   2940
actattttgt agtcgtctct caacaccgca tcatgcagac aagaagttgt gcattcagta   3000
actacaggtt tagctccata cctcatcaag atttttatag cctcggtatt cttgaacatt   3060
acagccattt caagaggaga ttgtagagta ccatattccg tgttagggtc gaatccattg   3120
tccaaaaacc tatttagaga tgcattgtca ttatccatga tagcctcaca gacgtatatg   3180
taagccatct tgaatgtata attttgttgt tttcaacaac cgctcgtgaa cagcttctat   3240
actttttcat tttcttcatg attaatatag tttacggaat ataagtatac aaaaagttta   3300
tagtaatctc ataatatctg aaacacatac ataaaacatg gaagaattac acgatgtcgt   3360
tgagataaat ggctttttat tgtcatagtt tacaaattcg cagtaatctt catcttttac   3420
gaatattgca gaatctgttt tatccaacca gtgatttttg tataatataa ctggtatcct   3480
atcttccgat agaatgctgt tatttaacat ttttgcacct attaagttac atctgtcaaa   3540
tccatctttc caactgactt tatgtaacga tgcgaaatag catttatcac tatgtcgtac   3600
ccaattatca tgacaagatt ctcttaaata cgtaatctta ttatctcttg catattcgta   3660
atagtaattg taaagagtat acgataacag tatagatata cacgtgatat aaatatttaa   3720
ccccattcct gagtaaaata attacgatat tacatttcct tttattattt ttatgtttta   3780
gttatttgtt aggttataca aaaattatgt ttatttgtgt atatttaaag cgtcgttaag   3840
aataagctta gttaacatat tatcgcttag gttttgtagt atttgaatcc tttctttaaa   3900
tggattattt ttccaatgca tatttatagc ttcatccaaa gtataacatt taacattca    3959
```

```
<210> SEQ ID NO 2
<211> LENGTH: 3917
<212> TYPE: DNA
<213> ORGANISM: Influenza A virus

<400> SEQUENCE: 2
gtattctaaa ctaggaatag atgaaattat gtgcaaagga gataccttta gatatggatc     60
tgatttattt ggtttttcat aatcataatc taacaacatt ttcactatac tataccttct    120
tgcacaagtc gccattagta gtatagactt atactttgta accatagtat actttagcgc    180
gtcatcttct tcatctaaaa cagatttaca acaataatca tcgtcgtcat cttcatcttc    240
attaaagttt tcatattcaa taactttctt ttctaaaaca tcatctgaat caataaacat    300
agaacggtat agagcgttaa tctccattgt aaaatatact aacgcgttgc tcatgatgta    360
cttttttttc attatttaga aattatgcat tttagatctt tataagcggc cgtgattaac    420
tagtcataaa aacccgggat cgattctaga ctcgagggta cctcaaatgc aaatgttgca    480
tctgatgttg cctttttggc aagcccacat aatgaaaccc aatagaacaa cgcaaattaa    540
gaagcatgat atggcgaatg aaatccacag tatccaatct ttgtagcctg atttcaactc    600
aacacctttg atttgaaatc ggttgtttaa tgcttcatct ctgtatatgt aatggtcata    660
tgtcccattt cttattgatc caatgcatgc attatcacat ttgtggtaaa tcttgaaaca    720
tccacctccc atgtcttccg cgttttctct taactggcgt ctagtcttct cgaataattt    780
```

-continued

| | |
|---|---|
| attcatttct gcatctgtta agtcaattgt atgttgattt tctagagcca ccagcaattc | 840 |
| tgcattgtag gaccataggt ctattttggt gtcttctaca tacttctcca agtcctggat | 900 |
| tctcccttct acttctgaga attccttctc tatttgatgg aatttctcat tggtcctttc | 960 |
| aatcactctg tttaattttc cattaatctg gtcgatggct gcttgagtgc tctttagatc | 1020 |
| tgcagcttgt cctgttcctt ccgagttttg atatcggaat ccataccacc catcaaccat | 1080 |
| tccttcccag ccgttttcta tgaatcccgc tattgctcca aagattcctc tgatttgctt | 1140 |
| ttctggtaca ttcctcatcc cagtggccag ctttaaagtg ttttgcctga tatacttggg | 1200 |
| gcattttcca tatgtaactt tgttcacatt ttgaaatggt ttgtcgttgg ggatgcttcc | 1260 |
| atttggtgta atacattcag acacacaaat gtctatgggt gcatctgatc tcattacaga | 1320 |
| gcttttccct gttttcaatt taaaatatcc ccgcggtgca actaagttgc cattactgtt | 1380 |
| tatcattagg atatctccag gttttacaat ggtccagtat atgcttatcc tgcctgattg | 1440 |
| accccctgacc cacggtctag atccgatatt agggattatc gtttgttgac ttcttttttgt | 1500 |
| tgagactgtt actcgtcctg attcttggat gtacaattct gtttgctgtt ggtttgagct | 1560 |
| cgggtgatga atcccccaga tgtatagttt gtcgaaattt ttattgttag gcattgtcac | 1620 |
| attcaatgtg gggtaagagt ttccagattt tgttagccaa ttcagtcggc taaagaaact | 1680 |
| atcggctgat cccctttttgc aggctccact tcttccgttt tgagtgacac ctgtccatgt | 1740 |
| gaatccctct gctgtgaatt ccaatgttcc tgaggatgct acaatggacc ggagcgatgc | 1800 |
| atagtcaggg atgtcatatg ggtagcaatt gctgaaagcg ctgcttcttt ctatgaagag | 1860 |
| gtcccaattc tcatactgaa agacatcaca gtgggggtct cctagcattg catctattaa | 1920 |
| tgtgcaattt cttccatcta gaactctata tgagttgttg catattttcc ctattgaaat | 1980 |
| gctctgaact aattcagtag catttgtcac ctcaatttgg tcatcagtta ttgttttttac | 2040 |
| caatgttcca tttgctactg catggtgtcc cagacataat gtggctgtgt tgttgccact | 2100 |
| ggttgggttt tgactgtaga cccaatgggt cagtagtatc aaaataatgg ttgtcttcat | 2160 |
| tacgatacaa acttaacgga tatcgcgata atgaaataat ttatgattat ttctcgcttt | 2220 |
| caatttaaca caaccctcaa gaacctttgt atttatttttc actttttaag tatagaataa | 2280 |
| agaagctcta attaattaac gagcagatag tctcgttctc gccctgcctg atgactaatt | 2340 |
| aattaacccg gatccttttt atagctaatt agtcacgtac ctttgagagt accacttcag | 2400 |
| ctacctcttt tgtgtctcag agtaactttc tttaatcaat tccaaaacag tatatgattt | 2460 |
| tccatttctt tcaaagatgt agtttacatc tgctcctttg ttgaaaagta gcctgagcac | 2520 |
| ttcttttcta ccatgaatta cagctggcaa gatcaatttt tcccagttct ggacatttta | 2580 |
| ttttttttaa gtagtgtgct acatatttca atatttccag attgtacagc gatcattaaa | 2640 |
| ggagtacgtc ccatgttatc cagcaagtca gtatcagcac ctttgttcaa tagaagttta | 2700 |
| accattgtta aattttttatt tgatacggct atatgtagag gagttaaccg atccgtgttt | 2760 |
| gaaatatcta catccgccga atgagccaat agaagtttaa ccaaattaac tttgttaagg | 2820 |
| taagctgcca aacacaaagg agtaaagcct ccgctgtaaa gaacattgtt tacatagtta | 2880 |
| ttcttcaaca gatctttcac tattttgtag tcgtctctca acaccgcatc atgcagacaa | 2940 |
| gaagttgtgc attcagtaac tacaggttta gctccatacc tcatcaagat ttttatagcc | 3000 |
| tcggtattct tgaacattac agccatttca agaggagatt gtagagtacc atattccgtg | 3060 |
| ttagggtcga atccattgtc caaaaaccta tttagagatg cattgtcatt atccatgata | 3120 |

-continued

```
gcctcacaga cgtatatgta agccatcttg aatgtataat tttgttgttt tcaacaaccg    3180
ctcgtgaaca gcttctatac ttttcattt tcttcatgat taatatagtt tacggaatat    3240
aagtatacaa aaagtttata gtaatctcat aatatctgaa acacatacat aaaacatgga    3300
agaattacac gatgtcgttg agataaatgg ctttttattg tcatagttta caaattcgca    3360
gtaatcttca tcttttacga atattgcaga atctgtttta tccaaccagt gattttgta    3420 taatataact ggtatcctat cttccgatag aatgctgtta tttaacattt ttgcacctat    3480
taagttacat ctgtcaaatc catctttcca actgacttta tgtaacgatg cgaaatagca    3540
tttatcacta tgtcgtaccc aattatcatg acaagattct cttaaatacg taatcttatt    3600
atctcttgca tattcgtaat agtaattgta aagagtatac gataacagta tagatataca    3660
cgtgatataa atatttaacc ccattcctga gtaaaataat tacgatatta catttccttt    3720
tattattttt atgttttagt tatttgttag gttatacaaa aattatgttt atttgtgtat    3780
atttaaagcg tcgttaagaa taagcttagt taacatatta tcgcttaggt tttgtagtat    3840
ttgaatcctt tctttaaatg gattattttt ccaatgcata tttatagctt catccaaagt    3900
ataacattta acattca                                                   3917
```

<210> SEQ ID NO 3
<211> LENGTH: 565
<212> TYPE: PRT
<213> ORGANISM: Influenza A virus

<400> SEQUENCE: 3

```
Met Lys Thr Thr Ile Ile Leu Ile Leu Leu Thr His Trp Val Tyr Ser
  1               5                  10                  15

Gln Asn Pro Thr Ser Gly Asn Asn Thr Ala Thr Leu Cys Leu Gly His
             20                  25                  30

His Ala Val Ala Asn Gly Thr Leu Val Lys Thr Ile Thr Asp Asp Gln
         35                  40                  45

Ile Glu Val Thr Asn Ala Thr Glu Leu Val Gln Ser Ile Ser Ile Gly
     50                  55                  60

Lys Ile Cys Asn Asn Ser Tyr Arg Val Leu Asp Gly Arg Asn Cys Thr
 65                  70                  75                  80

Leu Ile Asp Ala Met Leu Gly Asp Pro His Cys Asp Asp Phe Gln Tyr
                 85                  90                  95

Glu Asn Trp Asp Leu Phe Ile Glu Arg Ser Ser Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Leu Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Asn Ser Tyr
                165                 170                 175

Pro Ile Leu Asn Val Thr Met Pro Asn Asn Lys Asn Phe Asp Lys Leu
            180                 185                 190

Tyr Ile Trp Gly Ile His His Pro Ser Ser Asn Lys Glu Gln Thr Lys
        195                 200                 205

Leu Tyr Ile Gln Glu Ser Gly Arg Val Thr Val Ser Thr Glu Arg Ser
    210                 215                 220

Gln Gln Thr Val Ile Pro Asn Ile Gly Ser Arg Pro Trp Val Arg Gly
```

```
                225                 230                 235                 240
Gln Ser Gly Arg Ile Ser Ile Tyr Trp Thr Ile Val Lys Pro Gly Asp
                245                 250                 255
Ile Leu Met Ile Asn Ser Asn Gly Asn Leu Val Ala Pro Arg Gly Tyr
                260                 265                 270
Phe Lys Leu Arg Thr Gly Lys Ser Ser Val Met Arg Ser Asp Ala Leu
                275                 280                 285
Ile Asp Thr Cys Val Ser Glu Cys Ile Thr Pro Asn Gly Ser Ile Pro
                290                 295                 300
Asn Asp Lys Pro Phe Gln Asn Val Asn Lys Ile Thr Tyr Gly Lys Cys
305                 310                 315                 320
Pro Lys Tyr Ile Arg Gln Asn Thr Leu Lys Leu Ala Thr Gly Met Arg
                325                 330                 335
Asn Val Pro Glu Lys Gln Ile Arg Gly Ile Phe Gly Ala Ile Ala Gly
                340                 345                 350
Phe Ile Glu Asn Gly Trp Glu Gly Met Val Asp Gly Trp Tyr Gly Phe
                355                 360                 365
Arg Tyr Gln Asn Ser Glu Gly Thr Gly Gln Ala Ala Asp Leu Lys Ser
            370                 375                 380
Thr Gln Ala Ala Ile Asp Gln Ile Asn Gly Lys Leu Asn Arg Val Ile
385                 390                 395                 400
Glu Arg Thr Asn Glu Lys Phe His Gln Ile Glu Lys Glu Phe Ser Glu
                405                 410                 415
Val Glu Gly Arg Ile Gln Asp Leu Glu Lys Tyr Val Glu Asp Thr Lys
                420                 425                 430
Ile Asp Leu Trp Ser Tyr Asn Ala Glu Leu Leu Val Ala Leu Glu Asn
                435                 440                 445
Gln His Thr Ile Asp Leu Thr Asp Ala Glu Met Asn Lys Leu Phe Glu
            450                 455                 460
Lys Thr Arg Arg Gln Leu Arg Glu Asn Ala Glu Asp Met Gly Gly Gly
465                 470                 475                 480
Cys Phe Lys Ile Tyr His Lys Cys Asp Asn Ala Cys Ile Gly Ser Ile
                485                 490                 495
Arg Asn Gly Thr Tyr Asp His Tyr Ile Tyr Arg Asp Glu Ala Leu Asn
                500                 505                 510
Asn Arg Phe Gln Ile Lys Ser Val Glu Leu Lys Ser Gly Tyr Lys Asp
            515                 520                 525
Trp Ile Leu Trp Ile Ser Phe Ala Ile Ser Cys Phe Leu Ile Cys Val
                530                 535                 540
Val Leu Leu Gly Phe Ile Met Trp Ala Cys Gln Lys Gly Asn Ile Arg
545                 550                 555                 560
Cys Asn Ile Cys Ile
                565

<210> SEQ ID NO 4
<211> LENGTH: 565
<212> TYPE: PRT
<213> ORGANISM: Influenza A virus

<400> SEQUENCE: 4

Met Lys Thr Thr Ile Ile Leu Ile Leu Leu Thr His Trp Ala Tyr Ser
 1                   5                  10                  15

Gln Asn Pro Ile Ser Gly Asn Asn Thr Ala Thr Leu Cys Leu Gly His
                20                  25                  30
```

-continued

```
His Ala Val Ala Asn Gly Thr Leu Val Lys Thr Ile Ser Asp Asp Gln
             35                  40                  45
Ile Glu Val Thr Asn Ala Thr Glu Leu Val Gln Ser Ile Ser Met Gly
         50                  55                  60
Lys Ile Cys Asn Asn Ser Tyr Arg Ile Leu Asp Gly Arg Asn Cys Thr
 65                  70                  75                  80
Leu Ile Asp Ala Met Leu Gly Asp Pro His Cys Asp Ala Phe Gln Tyr
                 85                  90                  95
Glu Asn Trp Asp Leu Phe Ile Glu Arg Ser Ser Ala Phe Ser Asn Cys
            100                 105                 110
Tyr Pro Tyr Asp Ile Pro Asp Tyr Ala Ser Leu Arg Ser Ile Val Ala
            115                 120                 125
Ser Ser Gly Thr Leu Glu Phe Thr Ala Glu Gly Phe Thr Trp Thr Gly
        130                 135                 140
Val Thr Gln Asn Gly Arg Ser Gly Ala Cys Lys Arg Gly Ser Ala Asp
145                 150                 155                 160
Ser Phe Phe Ser Arg Leu Asn Trp Leu Thr Lys Ser Gly Ser Ser Tyr
                165                 170                 175
Pro Thr Leu Asn Val Thr Met Pro Asn Asn Lys Asn Phe Asp Lys Leu
            180                 185                 190
Tyr Ile Trp Gly Ile His His Pro Ser Ser Asn Gln Glu Gln Thr Lys
            195                 200                 205
Leu Tyr Ile Gln Glu Ser Gly Arg Val Thr Val Ser Thr Lys Arg Ser
        210                 215                 220
Gln Gln Thr Ile Ile Pro Asn Ile Gly Ser Arg Pro Trp Val Arg Gly
225                 230                 235                 240
Gln Ser Gly Arg Ile Ser Ile Tyr Trp Thr Ile Val Lys Pro Gly Asp
                245                 250                 255
Ile Leu Met Ile Asn Ser Asn Gly Asn Leu Val Ala Pro Arg Gly Tyr
            260                 265                 270
Phe Lys Leu Lys Thr Gly Lys Ser Ser Val Met Arg Ser Asp Val Pro
            275                 280                 285
Ile Asp Ile Cys Val Ser Glu Cys Ile Thr Pro Asn Gly Ser Ile Ser
290                 295                 300
Asn Asp Lys Pro Phe Gln Asn Val Asn Lys Val Thr Tyr Gly Lys Cys
305                 310                 315                 320
Pro Lys Tyr Ile Arg Gln Asn Thr Leu Lys Leu Ala Thr Gly Met Arg
                325                 330                 335
Asn Val Pro Glu Lys Gln Ile Arg Gly Ile Phe Gly Ala Ile Ala Gly
            340                 345                 350
Phe Ile Glu Asn Gly Trp Glu Gly Met Val Asp Gly Trp Tyr Gly Phe
        355                 360                 365
Arg Tyr Gln Asn Ser Glu Gly Thr Gly Gln Ala Ala Asp Leu Lys Ser
    370                 375                 380
Thr Gln Ala Ala Ile Asp Gln Ile Asn Gly Lys Leu Asn Arg Val Ile
385                 390                 395                 400
Glu Arg Thr Asn Glu Lys Phe His Gln Ile Glu Lys Glu Phe Ser Glu
                405                 410                 415
Val Glu Gly Arg Ile Gln Asp Leu Glu Lys Tyr Val Glu Asp Thr Lys
            420                 425                 430
Ile Asp Leu Trp Ser Tyr Asn Ala Glu Leu Leu Val Ala Leu Glu Asn
        435                 440                 445
Gln His Thr Ile Asp Leu Thr Asp Ala Glu Met Asn Lys Leu Phe Glu
```

-continued

```
            450                 455                 460
Lys Thr Arg Arg Gln Leu Lys Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
                500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
530                 535                 540

Val Leu Leu Gly Phe Ile Met Trp Ala Cys Gln Lys Gly Asn Ile Arg
545                 550                 555                 560

Cys Asn Ile Cys Ile
                565

<210> SEQ ID NO 5
<211> LENGTH: 565
<212> TYPE: PRT
<213> ORGANISM: Influenza A virus

<400> SEQUENCE: 5

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
                20                  25                  30

His Ala Val Ala Asn Gly Thr Leu Val Lys Thr Ile Ser Asp Asp Gln
            35                  40                  45

Ile Glu Val Thr Asn Ala Thr Glu Leu Val Gln Ser Ile Ser Met Gly
        50                  55                  60

Lys Ile Cys Asn Asn Ser Tyr Arg Ile Leu Asp Gly Arg Asn Cys Thr
65                  70                  75                  80

Leu Ile Asp Ala Met Leu Gly Asp Pro His Cys Asp Ala Phe Gln Tyr
                85                  90                  95

Glu Asn Trp Asp Leu Phe Ile Glu Arg Ser Ser Ala Phe Ser Asn Cys
                100                 105                 110

Tyr Pro Tyr Asp Ile Pro Asp Tyr Ala Ser Leu Arg Ser Ile Val Ala
            115                 120                 125

Ser Ser Gly Thr Leu Glu Phe Thr Ala Glu Gly Phe Thr Trp Thr Gly
        130                 135                 140

Val Thr Gln Asn Gly Arg Ser Gly Ala Cys Lys Arg Gly Ser Ala Asp
145                 150                 155                 160

Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro Asn Ile Gly Ser Arg Pro Trp Val Arg Gly
225                 230                 235                 240

Gln Ser Gly Arg Ile Ser Ile Tyr Trp Thr Ile Val Lys Pro Gly Asp
                245                 250                 255
```

| | | | | | | | | | | | | |
|---|---|---|---|---|---|---|---|---|---|---|---|---|
|Ile|Leu|Met|Ile|Asn|Ser|Asn|Gly|Asn|Leu|Val|Ala|Pro|Arg|Gly|Tyr|
| | |260| | | |265| | | |270| | | |

Phe Lys Leu Lys Thr Gly Lys Ser Ser Val Met Arg Ser Asp Val Pro
              275                 280                 285

Ile Asp Ile Cys Val Ser Glu Cys Ile Thr Pro Asn Gly Ser Ile Ser
              290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Ile Arg Gly Ile Phe Gly Ala Ile Ala Gly
                340                 345                 350

Phe Ile Glu Asn Gly Trp Glu Gly Met Val Asp Gly Trp Tyr Gly Phe
            355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
                420                 425                 430

Ile Asp Leu Trp Ser Tyr Asn Ala Glu Leu Leu Val Ala Leu Glu Asn
            435                 440                 445

Gln His Thr Ile Asp Leu Thr Asp Ala Glu Met Asn Lys Leu Phe Glu
    450                 455                 460

Lys Thr Arg Arg Gln Leu Lys Glu Asn Ala Glu Asp Met Gly Gly Gly
465                 470                 475                 480

Cys Phe Lys Ile Tyr His Lys Cys Asp Asn Ala Cys Ile Gly Ser Ile
                485                 490                 495

Arg Asn Gly Thr Tyr Asp His Tyr Ile Tyr Arg Asp Glu Ala Leu Asn
                500                 505                 510

Asn Arg Phe Gln Ile Lys Gly Val Glu Leu Lys Ser Gly Tyr Lys Asp
            515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565

```
<210> SEQ ID NO 6
<211> LENGTH: 3973
<212> TYPE: DNA
<213> ORGANISM: Influenza A virus
<220> FEATURE:
<221> NAME/KEY: CDS
<222> LOCATION: (1800)..(3494)

<400> SEQUENCE: 6
ggaaacagct atgaccatga ttacgaattg cggccgcaat tctgaatgtt aaatgttata    60
ctttggatga agctataaat atgcattgga aaaataatcc atttaaagaa aggattcaaa   120
tactacaaaa cctaagcgat aatatgttaa ctaagcttat tcttaacgac gctttaaata   180
tacacaaata aacataattt ttgtataacc taacaaataa ctaaaacata aaataataa    240
```

-continued

```
aaggaaatgt aatatcgtaa ttattttact caggaatggg gttaaatatt tatatcacgt    300
gtatatctat actgttatcg tatactcttt acaattacta ttcgaatat gcaagagata     360
ataagattac gtatttaaga gaatcttgtc atgataattg ggtacgacat agtgataaat    420
gctatttcgc atcgttacat aaagtcagtt ggaaagatgg atttgacaga tgtaacttaa    480
taggtgcaaa aatgttaaat aacagcattc tatcggaaga taggatacca gttatattat    540
acaaaaatca ctggttggat aaaacagatt ctgcaatatt cgtaaaagat gaagattact    600
gcgaatttgt aaactatgac aataaaaagc catttatctc aacgacatcg tgtaattctt    660
ccatgtttta tgtatgtgtt tcagatatta tgagattact ataaactttt tgtatactta    720
tattccgtaa actatattaa tcatgaagaa aatgaaaaag tatagaagct gttcacgagc    780
ggttgttgaa acaacaaaa ttatacattc aagatggctt acatatacgt ctgtgaggct     840
atcatggata tgacaatgc atctctaaat aggttttggg acaatggatt cgaccctaac     900
acggaatatg gtactctaca atctcctctt gaaatggctg taatgttcaa gaataccgag    960
gctataaaaa tcttgatgag gtatggagct aaacctgtag ttactgaatg cacaacttct   1020
tgtctgcatg atgcggtgtt gagagacgac tacaaaatag tgaaagatct gttgaagaat   1080
aactatgtaa acaatgttct ttacagcgga ggctttactc ctttgtgttt ggcagcttac   1140
cttaacaaag ttaatttggt taaacttcta ttggctcatt cggcggatgt agatatttca   1200
aacacggatc ggttaactcc tctacatata gccgtatcaa ataaaaattt aacaatggtt   1260
aaacttctat tgaacaaagg tgctgatact gacttgctgg ataacatggg acgtactcct   1320
ttaatgatcg ctgtacaatc tggaaatatt gaaatatgta gcacactact taaaaaaaat   1380
aaaatgtcca gaactgggaa aaattgatct tgccagctgt aattcatggt agaaaagaag   1440
tgctcaggct acttttcaac aaaggagcag atgtaaacta catctttgaa agaaatggaa   1500
aatcatatac tgttttggaa ttgattaaag aaagttactc tgagcacaa aagaggtagc    1560
tgaagtggta ctctcaaagg tacgtgacta attagctata aaaaggatcc gggttaatta   1620
attagtcatc aggcagggcg agaacgagac tatctgctcg ttaattaatt agagcttctt   1680
tattctatac ttaaaaagtg aaaataaata caaaggttct tgagggttgt gttaaattga   1740
aagcgagaaa taatcataaa ttatttcatt atcgcgatat ccgttaagtt tgtatcgta    1799
atg aaa acc acc atc atc ctg atc ctg ctg acc cac tgg gcc tac agc    1847
Met Lys Thr Thr Ile Ile Leu Ile Leu Leu Thr His Trp Ala Tyr Ser
 1               5                  10                  15
cag aac cct atc agc ggc aac aac acc gcc acc ctg tgc ctg ggc cac    1895
Gln Asn Pro Ile Ser Gly Asn Asn Thr Ala Thr Leu Cys Leu Gly His
             20                  25                  30
cac gcc gtg gcc aac ggc acc ctg gtc aag acc atc agc gac gac cag    1943
His Ala Val Ala Asn Gly Thr Leu Val Lys Thr Ile Ser Asp Asp Gln
         35                  40                  45
atc gaa gtg acc aac gcc acc gag ctg gtg cag agc atc agc atg ggc    1991
Ile Glu Val Thr Asn Ala Thr Glu Leu Val Gln Ser Ile Ser Met Gly
     50                  55                  60
aag atc tgc aac aac agc tac cgc atc ctg gac ggc aga aac tgc acc    2039
Lys Ile Cys Asn Asn Ser Tyr Arg Ile Leu Asp Gly Arg Asn Cys Thr
 65                  70                  75                  80
ctg atc gac gcc atg ctg ggc gac ccc cac tgc gac gcc ttc cag tac    2087
Leu Ile Asp Ala Met Leu Gly Asp Pro His Cys Asp Ala Phe Gln Tyr
                 85                  90                  95
gag aac tgg gac ctg ttc atc gag agg agc agc gcc ttc agc aac tgc    2135
Glu Asn Trp Asp Leu Phe Ile Glu Arg Ser Ser Ala Phe Ser Asn Cys
            100                 105                 110
```

-continued

```
tac ccc tac gac atc cct gac tac gcc agc ctg aga agc atc gtg gcc      2183
Tyr Pro Tyr Asp Ile Pro Asp Tyr Ala Ser Leu Arg Ser Ile Val Ala
        115                 120                 125
agc agc ggc acc ctg gag ttc acc gcc gag ggc ttc acc tgg acc ggc      2231
Ser Ser Gly Thr Leu Glu Phe Thr Ala Glu Gly Phe Thr Trp Thr Gly
    130                 135                 140
gtg acc cag aac ggc aga agc ggc gcc tgc aag aga ggc agc gcc gac      2279
Val Thr Gln Asn Gly Arg Ser Gly Ala Cys Lys Arg Gly Ser Ala Asp
145                 150                 155                 160
agc ttc ttc agc cgc ctg aac tgg ctg acc aag agc ggc agc agc tac      2327
Ser Phe Phe Ser Arg Leu Asn Trp Leu Thr Lys Ser Gly Ser Ser Tyr
                165                 170                 175
ccc acc ctg aac gtg acc atg ccc aac aac aag aac ttc gac aag ctg      2375
Pro Thr Leu Asn Val Thr Met Pro Asn Asn Lys Asn Phe Asp Lys Leu
            180                 185                 190
tac atc tgg ggc atc cac cac ccc agc agc aac cag gag cag acc aag      2423
Tyr Ile Trp Gly Ile His His Pro Ser Ser Asn Gln Glu Gln Thr Lys
        195                 200                 205
ctg tac atc cag gag agc ggc aga gtg acc gtg tcc acc aag aga agc      2471
Leu Tyr Ile Gln Glu Ser Gly Arg Val Thr Val Ser Thr Lys Arg Ser
    210                 215                 220
cag cag acc atc atc ccc aac atc ggc agc aga cct tgg gtg cgc ggc      2519
Gln Gln Thr Ile Ile Pro Asn Ile Gly Ser Arg Pro Trp Val Arg Gly
225                 230                 235                 240
cag tcc ggc agg atc agc atc tac tgg acc atc gtg aag cct ggc gac      2567
Gln Ser Gly Arg Ile Ser Ile Tyr Trp Thr Ile Val Lys Pro Gly Asp
                245                 250                 255
atc ctg atg atc aac agc aac ggc aac ctg gtg gcc ccc aga ggc tac      2615
Ile Leu Met Ile Asn Ser Asn Gly Asn Leu Val Ala Pro Arg Gly Tyr
            260                 265                 270
ttc aag ctg aaa acc ggc aag agc agc gtg atg aga agc gac gtg ccc      2663
Phe Lys Leu Lys Thr Gly Lys Ser Ser Val Met Arg Ser Asp Val Pro
        275                 280                 285
atc gac atc tgc gtg tcc gag tgc atc acc cct aac ggc agc atc agc      2711
Ile Asp Ile Cys Val Ser Glu Cys Ile Thr Pro Asn Gly Ser Ile Ser
    290                 295                 300
aac gac aag ccc ttc cag aac gtg aac aaa gtg acc tac ggc aag tgc      2759
Asn Asp Lys Pro Phe Gln Asn Val Asn Lys Val Thr Tyr Gly Lys Cys
305                 310                 315                 320
ccc aag tac atc cgc cag aac acc ctg aag ctg gcc acc ggc atg aga      2807
Pro Lys Tyr Ile Arg Gln Asn Thr Leu Lys Leu Ala Thr Gly Met Arg
                325                 330                 335
aac gtg ccc gag aag cag atc aga ggc atc ttc ggc gcc atc gcc ggc      2855
Asn Val Pro Glu Lys Gln Ile Arg Gly Ile Phe Gly Ala Ile Ala Gly
            340                 345                 350
ttc atc gag aac ggc tgg gag ggc atg gtg gac ggc tgg tac ggc ttc      2903
Phe Ile Glu Asn Gly Trp Glu Gly Met Val Asp Gly Trp Tyr Gly Phe
        355                 360                 365
aga tac cag aac agc gag ggc acc ggc cag gcc gcc gac ctg aag agc      2951
Arg Tyr Gln Asn Ser Glu Gly Thr Gly Gln Ala Ala Asp Leu Lys Ser
    370                 375                 380
acc cag gcc gcc atc gac cag atc aac ggc aag ctg aac cgc gtg atc      2999
Thr Gln Ala Ala Ile Asp Gln Ile Asn Gly Lys Leu Asn Arg Val Ile
385                 390                 395                 400
gag cgc acc aac gag aag ttc cac cag atc gag aag gag ttc agc gaa      3047
Glu Arg Thr Asn Glu Lys Phe His Gln Ile Glu Lys Glu Phe Ser Glu
                405                 410                 415
gtg gag ggc aga atc cag gac ctg gag aag tac gtg gag gac acc aag      3095
Val Glu Gly Arg Ile Gln Asp Leu Glu Lys Tyr Val Glu Asp Thr Lys
```

|  |  |  |  |  |  |  |  |  |  |  |  |  |  |  |  |
|---|---|---|---|---|---|---|---|---|---|---|---|---|---|---|---|
|  |  |  |  | 420 |  |  |  | 425 |  |  |  | 430 |  |  |  |
| atc | gac | ctg | tgg | agc | tac | aac | gcc | gag | ctg | ctg | gtc | gcc | ctg | gag | aac |
| Ile | Asp | Leu | Trp | Ser | Tyr | Asn | Ala | Glu | Leu | Leu | Val | Ala | Leu | Glu | Asn |
|  |  | 435 |  |  |  | 440 |  |  |  | 445 |  |  |  |  |  |
| cag | cac | acc | atc | gac | ctg | acc | gac | gcc | gag | atg | aac | aag | ctg | ttc | gaa |
| Gln | His | Thr | Ile | Asp | Leu | Thr | Asp | Ala | Glu | Met | Asn | Lys | Leu | Phe | Glu |
|  | 450 |  |  |  |  | 455 |  |  |  |  | 460 |  |  |  |  |
| aag | acc | agg | cgc | cag | ctg | aag | gaa | aac | gcc | gag | gac | atg | ggc | ggc | ggc |
| Lys | Thr | Arg | Arg | Gln | Leu | Lys | Glu | Asn | Ala | Glu | Asp | Met | Gly | Gly | Gly |
| 465 |  |  |  |  | 470 |  |  |  |  | 475 |  |  |  |  | 480 |
| tgc | ttc | aag | atc | tac | cac | aag | tgc | gac | aac | gcc | tgc | atc | ggc | tcc | atc |
| Cys | Phe | Lys | Ile | Tyr | His | Lys | Cys | Asp | Asn | Ala | Cys | Ile | Gly | Ser | Ile |
|  |  |  |  | 485 |  |  |  | 490 |  |  |  | 495 |  |  |  |
| agg | aac | ggc | acc | tac | gac | cac | tac | atc | tac | agg | gac | gag | gcc | ctg | aac |
| Arg | Asn | Gly | Thr | Tyr | Asp | His | Tyr | Ile | Tyr | Arg | Asp | Glu | Ala | Leu | Asn |
|  |  |  | 500 |  |  |  | 505 |  |  |  | 510 |  |  |  |  |
| aac | cgc | ttc | cag | atc | aag | ggc | gtg | gag | ctg | aag | agc | ggc | tac | aag | gac |
| Asn | Arg | Phe | Gln | Ile | Lys | Gly | Val | Glu | Leu | Lys | Ser | Gly | Tyr | Lys | Asp |
|  |  | 515 |  |  |  | 520 |  |  |  | 525 |  |  |  |  |  |
| tgg | atc | ctg | tgg | atc | agc | ttc | gcc | atc | agc | tgc | ttc | ctg | atc | tgc | gtg |
| Trp | Ile | Leu | Trp | Ile | Ser | Phe | Ala | Ile | Ser | Cys | Phe | Leu | Ile | Cys | Val |
|  | 530 |  |  |  |  | 535 |  |  |  |  | 540 |  |  |  |  |
| gtg | ctg | ctg | ggc | ttc | atc | atg | tgg | gcc | tgc | cag | aag | ggc | aac | atc | cgc |
| Val | Leu | Leu | Gly | Phe | Ile | Met | Trp | Ala | Cys | Gln | Lys | Gly | Asn | Ile | Arg |
| 545 |  |  |  |  | 550 |  |  |  |  | 555 |  |  |  |  | 560 |
| tgc | aac | atc | tgc | atc | tgatgactcg | agggttttta | tgactagtta | atcacggccg |
| Cys | Asn | Ile | Cys | Ile |
|  |  |  |  | 565 |

|  |  |
|---|---|
| atc gac ctg tgg agc tac aac gcc gag ctg ctg gtc gcc ctg gag aac | 3143 |
| cag cac acc atc gac ctg acc gac gcc gag atg aac aag ctg ttc gaa | 3191 |
| aag acc agg cgc cag ctg aag gaa aac gcc gag gac atg ggc ggc ggc | 3239 |
| tgc ttc aag atc tac cac aag tgc gac aac gcc tgc atc ggc tcc atc | 3287 |
| agg aac ggc acc tac gac cac tac atc tac agg gac gag gcc ctg aac | 3335 |
| aac cgc ttc cag atc aag ggc gtg gag ctg aag agc ggc tac aag gac | 3383 |
| tgg atc ctg tgg atc agc ttc gcc atc agc tgc ttc ctg atc tgc gtg | 3431 |
| gtg ctg ctg ggc ttc atc atg tgg gcc tgc cag aag ggc aac atc cgc | 3479 |
| tgc aac atc tgc atc tgatgactcg agggttttta tgactagtta atcacggccg | 3534 |
| cttataaaga tctaaaatgc ataatttcta ataatgaaa aaagtacat catgagcaac | 3594 |
| gcgttagtat attttacaat ggagattaac gctctatacc gttctatgtt tattgattca | 3654 |
| gatgatgttt tagaaaagaa agttattgaa tatgaaaact ttaatgaaga tgaagatgac | 3714 |
| gacgatgatt attgttgtaa atctgtttta gatgaagaag atgacgcgct aaagtatact | 3774 |
| atggttacaa agtataagtc tatactacta atggcgactt gtgcaagaag gtatagtata | 3834 |
| gtgaaaatgt tgttagatta tgattatgaa aaaccaaata atcagatcc atatctaaag | 3894 |
| gtatctcctt tgcacataat ttcatctatt cctagtttag aatacctgca gccaagcttg | 3954 |
| gcactggccg tcgttttac | 3973 |

<210> SEQ ID NO 7
<211> LENGTH: 3973
<212> TYPE: DNA
<213> ORGANISM: Influenza A virus

<400> SEQUENCE: 7

| gtaaaacgac ggccagtgcc aagcttggct gcaggtattc taaactagga atagatgaaa | 60 |
| ttatgtgcaa aggagatacc tttagatatg gatctgattt atttggtttt tcataatcat | 120 |
| aatctaacaa catttttcact atactatacc ttcttgcaca agtcgccatt agtagtatag | 180 |
| acttatactt tgtaaccata gtatacttta gcgcgtcatc ttcttcatct aaaacagatt | 240 |
| tacaacaata atcatcgtcg tcatcttcat cttcattaaa gttttcatat tcaataactt | 300 |
| tcttttctaa aacatcatct gaatcaataa acatagaacg gtatagagcg ttaatctcca | 360 |
| ttgtaaaata tactaacgcg ttgctcatga tgtactttt ttcattattt agaaattatg | 420 |
| catttttagat cttataaagc ggccgtgatt aactagtcat aaaaaccctc gagtcatcag | 480 |
| atgcagatgt tgcagcggat gttgcccttc tggcaggccc acatgatgaa gcccagcagc | 540 |

```
accacgcaga tcaggaagca gctgatggcg aagctgatcc acaggatcca gtccttgtag    600
ccgctcttca gctccacgcc cttgatctgg aagcggttgt tcagggcctc gtccctgtag    660
atgtagtggt cgtaggtgcc gttcctgatg gagccgatgc aggcgttgtc gcacttgtgg    720
tagatcttga agcagccgcc gcccatgtcc tcggcgtttt ccttcagctg gcgcctggtc    780
ttttcgaaca gcttgttcat ctcggcgtcg gtcaggtcga tggtgtgctg gttctccagg    840
gcgaccagca gctcggcgtt gtagctccac aggtcgatct tggtgtcctc cacgtacttc    900
tccaggtcct ggattctgcc ctccacttcg ctgaactcct tctcgatctg gtggaacttc    960
tcgttggtgc gctcgatcac gcggttcagc ttgccgttga tctggtcgat ggcggcctgg   1020
gtgctcttca ggtcggcggc ctggccggtg ccctcgctgt tctggtatct gaagccgtac   1080
cagccgtcca ccatgccctc ccagccgttc tcgatgaagc cggcgatggc gccgaagatg   1140
cctctgatct gcttctcggg cacgtttctc atgccggtgg ccagcttcag ggtgttctgg   1200
cggatgtact tggggcactt gccgtaggtc actttgttca cgttctggaa gggcttgtcg   1260
ttgctgatgc tgccgttagg ggtgatgcac tcggacacgc agatgtcgat gggcacgtcg   1320
cttctcatca cgctgctctt gccggttttc agcttgaagt agcctctggg ggccaccagg   1380
ttgccgttgc tgttgatcat caggatgtcg ccaggcttca cgatggtcca gtagatgctg   1440
atcctgccgg actggccgcg cacccaaggt ctgctgccga tgttggggat gatggtctgc   1500
tggcttctct tggtggacac ggtcactctg ccgctctcct ggatgtacag cttggtctgc   1560
tcctggttgc tgctggggtg gtggatgccc agatgtaca gcttgtcgaa gttcttgttg   1620
ttgggcatgg tcacgttcag ggtggggtag ctgctgccgc tcttggtcag ccagttcagg   1680
cggctgaaga agctgtcggc gctgcctctc ttgcaggcgc gcttctgcc gttctgggtc   1740
acgccggtcc aggtgaagcc ctcggcggtg aactccaggg tgccgctgct ggccacgatg   1800
cttctcaggc tggcgtagtc agggatgtcg taggggtagc agttgctgaa ggcgctgctc   1860
ctctcgatga acaggtccca gttctcgtac tggaaggcgt cgcagtgggg gtcgcccagc   1920
atggcgtcga tcagggtgca gtttctgccg tccaggatgc ggtagctgtt gttgcagatc   1980
ttgcccatgc tgatgctctg caccagctcg gtggcgttgg tcacttcgat ctggtcgtcg   2040
ctgatggtct tgaccagggt gccgttggcc acggcgtggt ggcccaggca cagggtggcg   2100
gtgttgttgc cgctgatagg gttctggctg taggcccagt gggtcagcag gatcaggatg   2160
atggtggttt tcattacgat acaaacttaa cggatatcgc gataatgaaa taatttatga   2220
ttatttctcg ctttcaattt aacacaaccc tcaagaacct tgtatttat tttcactttt    2280
taagtataga ataaagaagc tctaattaat taacgagcag atagtctcgt tctcgccctg   2340
cctgatgact aattaattaa cccggatcct ttttatagct aattagtcac gtacctttga   2400
gagtaccact tcagctacct cttttgtgtc tcagagtaac tttctttaat caattccaaa   2460
acagtatatg attttccatt tctttcaaag atgtagttta catctgctcc tttgttgaaa   2520
agtagcctga gcacttcttt tctaccatga attcagctg gcaagatcaa ttttttccag    2580
ttctggacat tttatttttt ttaagtagtg tgctacatat ttcaatattt ccagattgta   2640
cagcgatcat taaggagta cgtcccatgt tatccagcaa gtcagtatca gcacctttgt    2700
tcaatagaag tttaaccatt gttaaatttt tatttgatac ggctatatgt agaggagtta   2760
accgatccgt gtttgaaata tctacatccg ccgaatgagc caatagaagt ttaaccaaat   2820
taactttgtt aaggtaagct gccaaacaca aaggagtaaa gcctccgctg taaagaacat   2880
```

-continued

```
tgtttacata gttattcttc aacagatctt tcactatttt gtagtcgtct ctcaacaccg    2940
catcatgcag acaagaagtt gtgcattcag taactacagg tttagctcca tacctcatca    3000
agatttttat agcctcggta ttcttgaaca ttacagccat ttcaagagga gattgtagag    3060
taccatattc cgtgttaggg tcgaatccat tgtccaaaaa cctatttaga gatgcattgt    3120
cattatccat gatagcctca cagacgtata tgtaagccat cttgaatgta aattttgtt     3180 gttttcaaca accgctcgtg aacagcttct atactttttc attttcttca tgattaatat    3240
agtttacgga atataagtat acaaaaagtt tatagtaatc tcataatatc tgaaacacat    3300
acataaaaca tggaagaatt acgcgatgtc gttgagataa atggctttt attgtcatag     3360 tttacaaatt cgcagtaatc ttcatctttt acgaatattg cagaatctgt tttatccaac    3420
cagtgatttt tgtataatat aactggtatc ctatcttccg atagaatgct gttatttaac    3480
atttttgcac ctattaagtt acatctgtca aatccatctt tccaactgac tttatgtaac    3540
gatgcgaaat agcattatc actatgtcgt acccaattat catgacaaga ttctcttaaa     3600
tacgtaatct tattatctct tgcatattcg taatagtaat tgtaaagagt atacgataac    3660
agtatagata tacacgtgat ataaatattt aaccccattc ctgagtaaaa taattacgat    3720
attacatttc cttttattat tttatgtttt tagttatttg ttaggttata caaaaattat    3780
gtttatttgt gtatatttaa agcgtcgtta agaataagct tagttaacat attatcgctt    3840
aggttttgta gtatttgaat cctttcttta aatggattat ttttccaatg catatttata    3900
gcttcatcca agtataaca tttaacattc agaattgcgg ccgcaattcg taatcatggt     3960
catagctgtt tcc                                                        3973
```

<210> SEQ ID NO 8  
<211> LENGTH: 890  
<212> TYPE: DNA  
<213> ORGANISM: Influenza A virus

<400> SEQUENCE: 8

```
agcaaaagca gggtgacaaa acataatgg attccaacac tgtgtcaagc tttcaggtag     60
actgttttct ttggcatgtc cgcaaacgat tcgcagacca agaactgggt gatgccccat    120
tccttgaccg gcttcgccga gaccagaagt ccctaagggg aagaggtatc actcttggtc    180
tggacatcga aacagccact catgcaggaa agcagatagt ggagcagatt ctggaaaagg    240
aatcagatga ggcacttaaa atgaccattg cctctgttcc tacttcacgc tacttaactg    300
acatgactct tgatgagatg tcaagagact ggttcatgct catgcccaag caaaaagtaa    360
caggctccct atgtataaga atggaccagg caatcatgga taagaacatc atacttaaag    420
caaactttag tgtgatttc gaaaggctgg aaacactaat actacttaga gccttcaccg    480
aagaaggagc agtcgttggc gaaatttcac cattaccttc tcttccagga catactaatg    540
aggatgtcaa aaatgcaatt ggggtcctca tcggaggact aaatggaat gataatacgg     600 ttagaatctc tgaaactcta cagagattcg cttggagaag cagtcatgag aatgggagac    660
cttcattccc ttcaaagcag aaatgaaaaa tggagagaac aattaagcca gaatttgaa    720 gaaataagat ggttgattga agaagtgcga catagattga aaaatacaga aaatagtttt    780
gaacaaataa catttatgca agccttacaa ctattgcttg aagtagaaca agagataaga    840
actttctcgt ttcagcttat ttaatgataa aaacaccct tgtttctact                 890
```

<210> SEQ ID NO 9  
<211> LENGTH: 1027

-continued

<212> TYPE: DNA
<213> ORGANISM: Influenza A virus

<400> SEQUENCE: 9
agcaaaagca ggtagatatt taaagatgag tcttctgacc gaggtcgaaa cgtacgttct 60
ctctatcgta ccatcaggcc ccctcaaagc cgagatcgcg cagagacttg aagatgtctt 120
tgcagggaag aacaccgatc ttgaggcact catggaatgg ctaaagacaa gaccaatcct 180
gtcacctttg actaaaggga ttttaggatt tgtattcacg ctcaccgtgc ccagtgagcg 240
aggactgcag cgtagacgct ttgtccaaaa tgcccttagt ggaaacggag atccaaacaa 300
catggacaga gcagtaaaac tgtacaggaa gcttaaaaga gaaataacat tccatggggc 360
aaaagaggtg gcactaagct attccactgg tgcactagcc agctgcatgg gactcatata 420
caacagaatg ggaactgtga caaccgaagt ggcatttggc ctggtatgcg ccacatgtga 480
acagattgct gattcccagc atcgatctca caggcagatg gtgacaacaa ccaacccatt 540
aatcagacat gaaaacagaa tggtattagc cagtaccacg gctaaagcca tggaacagat 600
ggcaggatca agtgagcagg cagcagaggc catggaggtt gctagtaagg ctaggcagat 660
ggtacaggca atgagaacca ttgggaccca ccctagctcc agtgccggtt tgaaagatga 720
tctccttgaa aatttacagg cctaccagaa acggatggga gtgcaaatgc agcgattcaa 780
gtgatcctct cgttattgca gcaagtatca ttgggatctt gcacttgata ttgtggattc 840
ttgatcgtct ttttcttcaaa ttcatttatc gtcgccttaa atacgggttg aaaagagggc 900
cttctacgga aggagtacct gagtctatga gggaagaata tcggcaggaa cagcagaatg 960
ctgtggatgt tgacgatggt cattttgtca acatagagct ggagtaaaaa actaccttgt 1020
ttctact 1027

<210> SEQ ID NO 10
<211> LENGTH: 1460
<212> TYPE: DNA
<213> ORGANISM: Influenza A virus

<400> SEQUENCE: 10
agcaaaagca ggagtttaaa atgaatccaa atcaaaagat aatagcaatt ggatttgcat 60
cattggggat attaatcatt aacgtcattc tccatgtagt cagcattata gtaacagtac 120
tggtcctcaa taacaatgga acaggtctga actgcaaagg gacgatcata agagagtaca 180
atgaaacagt aagagtagaa aaaattactc aatggtataa taccagtgca attaagtaca 240
tagagagacc tccaaatgaa tactacatga acaacaccga accactttgt gaggcccaag 300
gctttgcacc attttccaaa gataatggaa tacgaattgg gtcgagaggc catgtttttg 360
tgataagaga accttttgta tcatgttcgc cctcagaatg tagaaccttt ttcctcacac 420
agggctcatt actcaatgac aaacattcta acggcacagt aaaggaccga agtccatata 480
ggactttgat gagtgtcaaa atagggcaat cacctaatgt gtatcaagct aggtttgaat 540
cggtggcatg gtcagcaaca gcatgccatg atggaaaaaa atggatgaca gttggagtca 600
cagggcccga caatcaagca attgcagtag tgaactatgg aggtgttccg gttgatatta 660
ttaattcatg ggcaggggat atcttaagaa cccaagaatc atcatgcacc tgcattaaag 720
gagactgtta ttgggtaatg actgatggac cggcaaatag gcaagctaaa tataggatat 780
tcaaagcaaa agatggaaga gtaattggac agactgatat aagtttcaat gggggacaca 840
tagaggagtg ttcttgttac cccaatgaag ggaaggtgga atgcatatgc agggacaatt 900

-continued

| | |
|---|---|
| ggactggaac aaatagacca attctggtaa tatcttctga tctatcgtac acagttggat | 960 |
| atttgtgtgc tggcattccc actgacactc ctaggggaga ggatagtcaa ttcacaggct | 1020 |
| catgtacaag acctttggga aataaaggat acggtgtaaa aggtttcggg tttcgacaag | 1080 |
| gaactgacgt atgggccgga aggacaatta gtaggacttc aagatcagga ttcgaaataa | 1140 |
| taaaaatcag gaatggttgg acacagaaca gtaaagacca aatcaggagg caagtgatta | 1200 |
| tcgatgaccc aaattggtca ggatatagcg gttctttcac attgccggtt gaactaacaa | 1260 |
| aaaagggatg tttggtcccc tgtttctggg ttgaaatgat tagaggtaaa cctgaagaaa | 1320 |
| caacaatatg gacctctagc agctccattg tgatgtgtgg agtagatcat aaaattgcca | 1380 |
| gttggtcatg gcacgatgga gctattcttc cctttgacat cgataagatg taatttacga | 1440 |
| aaaaactcct tgtttctact | 1460 |

<210> SEQ ID NO 11
<211> LENGTH: 1565
<212> TYPE: DNA
<213> ORGANISM: Influenza A virus

<400> SEQUENCE: 11

| | |
|---|---|
| agcaaaagca gggtagataa tcactcactg agtgacatca aagtcatggc gtctcaaggc | 60 |
| accaaacgat cctatgaaca gatggaaact gatggggaac gccagaatgc aactgaaatc | 120 |
| agagcatctg tcggaaggat ggtgggagga atcggccggt tttatgttca gatgtgtact | 180 |
| gagcttaaac taaacgacca tgaagggcgg ctgattcaga acagcataac aatagaaagg | 240 |
| atggtacttt cggcattcga cgaaagaaga acaagtatc tcgaggagca tcccagtgct | 300 |
| ggaaaagacc ctaagaaaac gggaggcccg atatacagaa ggaaagatgg gaaatggatg | 360 |
| agggaactca tcctccatga taaagaagaa atcatgagaa tctggcgtca ggccaacaat | 420 |
| ggtgaagacg ctactgctgg tcttactcat atgatgatct ggcactccaa tctcaatgac | 480 |
| accacatacc aaagaacaag ggctcttgtt cggactggga tggatccag aatgtgctct | 540 |
| ctgatgcaag gctcaaccct cccacgagga tctggagccg ctggtgctgc agtaaaaggt | 600 |
| gttggaacaa tggtaatgga actcatcaga atgatcaaac gcggaataaa tgatcggaat | 660 |
| ttctggagag gtgaaaatgg tcgaaggacc agaattgctt atgaaagaat gtgcaatatc | 720 |
| ctcaaaggga aatttcagac agcagcacaa cgggctatga tggaccaggt gagggaaggc | 780 |
| cgcaatcctg aaacgctga gattgaggat ctcattttct tagcacgatc agcacttatt | 840 |
| ttgagaggat cagtagccca taaatcatgc ctacctgcct gtgtttatgg ccttgcagta | 900 |
| accagtgggt atgactttga aaggaaggga tactctctgg ttggaattga tcctttcaaa | 960 |
| ctactccaga acagtcaaat tttcagtcta atcagaccaa agaaaaaccc agcacacaag | 1020 |
| agccagttgg tgtggatggc atgccattct gcagcatttg aggacctgag agttttgaat | 1080 |
| ttcattagag gaaccaaagt aatcccaaga ggacagttaa caaccagagg agttcaaatt | 1140 |
| gcttcaaatg aaaacatgga gacaatagat tctagcacac ttgaactgag aagcaaatat | 1200 |
| tgggcaataa ggaccagaag tggaggaaac accgtcaac agagagcatc tgcaggacag | 1260 |
| ataagtgtgc aacctacttt ctcagtacag agaaatcttc cctttgagag agcaaccatt | 1320 |
| atggctgcat tcactggtaa cactgaaggg aggacttccg acatgagaac ggaaatcata | 1380 |
| aggatgatgg aaagtgccaa atcagaagat gtgtctttcc aggggcgggg agtcttcgag | 1440 |
| ctctcggacg aaaaggcaac gaacccgatc gtgccttcct tgacatgag caatgaaggg | 1500 |
| tcttatttct tcggagacaa tgctgaggaa tttgacagtt aaagaaaaat acccttgttt | 1560 | ctact                                                                   1565

<210> SEQ ID NO 12
<211> LENGTH: 1762
<212> TYPE: DNA
<213> ORGANISM: Influenza A virus

<400> SEQUENCE: 12
agcaaaagca ggggatattt ctgtcaatca tgaagacaac cattattttg atactactga      60
cccattgggc ctacagtcaa aacccaatca gtggcaacaa cacagccaca ttgtgtctgg     120
gacaccatgc agtagcaaat ggaacattgg taaaaacaat aagtgatgat caaattgagg     180
tgacaaatgc tacagaatta gttcagagca tttcaatggg gaaaatatgc aacaactcat     240
atagaattct agatggaaga aattgcacat taatagatgc aatgctagga gacccccact     300
gtgacgtctt tcagtatgag aattgggacc tctttataga agaagcagc gctttcagca     360
attgctaccc atatgacatc cctgactatg catcgctccg atccattgta gcatcctcag     420
gaacattgga attcacagca gagggattca catggacagg tgtcactcaa aacggaagaa     480
gtggagcctg caaaagggga tcagccgata gtttctttag ccgactgaat tggctaacaa     540
aatctggaaa ctcttacccc acattgaatg tgacaatgcc taacaataaa aatttcgaca     600
agctatacat ctgggggatt catcacccga gctcaaatca gagcagaca aaattgtaca     660
tccaagaatc aggacgagta acagtctcaa caaaaagaag tcaacaaaca ataatcccta     720
acatcggatc tagaccgtgg gtcagaggtc aatcaggcag ataagcata tactggacca     780
ttgtaaaacc tggagatatc ctaatgataa acagtaatgg caacttagtt gcaccgcggg     840
gatattttaa attgaaaaca gggaaaagct ctgtaatgag atcagatgca cccatagaca     900
tttgtgtgtc tgaatgtatt acaccaaatg gaagcatctc caacgacaag ccattccaaa     960
atgtgaacaa agttacatat ggaaaatgcc ccaagtatat caggcaaaac actttaaagt    1020
tggccactgg gatgaggaat gtaccagaaa agcaaatcag aggaatcttt ggagcaatag    1080
cgggattcat cgaaaacggc tgggaaggaa tggttgatgg tggtatggg ttccgatatc    1140
aaaactctga aggaacaggg caagctgcag atctaaagag cactcaagca gccatcgacc    1200
agattaatgg aaagttaaac agagtgattg aagaaccaa tgagaaattc catcaaatag    1260
agaaggaatt ctcagaagta aaggaagaa ttcaggactt ggagaaatat gtagaagaca    1320
ccaaaataga cctatggtcc tacaatgcag aattgctggt ggctctagaa atcaacata    1380
caattgactt aacagatgca gaaatgaata aattattcga gaagactaga cgccagttaa    1440
gagaaaacgc agaagacatg ggaggtggat gtttcaagat ttaccacaaa tgtgataatg    1500
catgcattgg atcaataaga aatgggacat atgaccatta catatacaga gatgaagcat    1560
taaacaaccg atttcaaatc aaaggtgttg agttgaaatc aggctacaaa gattggatac    1620
tgtggatttc attcgccata tcatgcttct taatttgcgt tgttctattg gtttcatta    1680
tgtgggcttg ccaaaaaggc aacatcagat gcaacatttg catttgagta aactgatagt    1740
taaaaacacc cttgtttcta ct                                              1762

<210> SEQ ID NO 13
<211> LENGTH: 2233
<212> TYPE: DNA
<213> ORGANISM: Influenza A virus

<400> SEQUENCE: 13

```
agcgaaagca ggtactgatc caaaatggaa gactttgtgc gacagtgctt caatccaatg     60
atcgtcgagc ttgcggaaaa ggcaatgaaa gaatatggag aggacccgaa atcgaaaca    120 aacaaatttg cagcaatatg cactcacttg gaagtctgct tcatgtactc ggatttccac    180
tttattaatg aactgggtga gtcagtggtc atagagtctg gtgacccaaa tgctcttttg    240
aaacacagat ttgaaatcat tgaggggaga gatcgaacaa tggcatggac agtggtaaac    300
agcatctgca acaccacaag agctgaaaaa cctaaatttc ttccagattt atacgactat    360
aaggagaaca gatttgttga aattggtgtg acaaggagag aagttcacat atactacctg    420
gagaaggcca caaaataaa gtctgagaaa acacatatcc acattttctc atttacagga    480
gaggaaatgg ctacaaaagc ggactatact cttgatgaag agagtagagc caggatcaag    540
accagactat tcactataag acaagaaatg gccagtagag gcctctggga ttcctttcgt    600
cagtccgaga gaggcgaaga gacaattgaa gaaagatttg aaatcacagg gacgatgcgc    660
aagcttgcca attacagtct cccaccgaac ttctccagcc ttgaaaattt tagagtctat    720
gtggatggat tcgaaccgaa cggctgcatt gagagtaagc tttctcaaat gtccaaagaa    780
gtaaatgcca gaatcgaacc attttcaaag acaacacccc gaccactcaa aatgccaggt    840
ggtccaccct gccatcagcg atctaaattc ttgctaatgg atgctctgaa actgagcatt    900
gaggacccaa gtcacgaggg agagggaata ccactatatg atgcaatcaa atgcatgaaa    960
actttctttg gatggaaaga gcccagtatt gttaaaccac atgaaaaggg tataaacccg   1020
aactatctcc aaacttggaa gcaagtatta agaaaatac aagaccttga gaacgaagaa   1080
aggaccccca agaccaagaa tatgaaaaaa acaagccaat tgaaatgggc actaggtgaa   1140 aatatgcac cagagaaagt ggattttgag gattgtaaag acatcagtga tttaaaacag   1200
tatgacagcg atgagccaga acaaggtct cttgcaagtt ggattcaaag tgagttcaac   1260
aaagcttgtg agctgacaga ttcaagctgg atagagctcg atgaaattgg ggaggatgtc   1320
gccccaatag aatacattgc gagcatgagg agaaattatt ttactgctga gatttcccat   1380
tgtagagcaa cagaatatat aatgaaagga gtgtacatca acactgctct actcaatgca   1440
tcctgtgctg cgatggatga atttcaatta attccgatga taagtaaatg caggaccaaa   1500
gaagggagaa ggaaaacaaa tttatatgga ttcataataa agggaaggtc ccatttaaga   1560
aatgatactg acgtggtgaa ctttgtaagt atggaatttt ctctcactga tccaagattt   1620
gagccacaca aatgggaaaa atactgcgtt ctagaaattg gagacatgct tctaaggact   1680
gctgtaggtc aagtgtcaag acccatgttt ttgtatgtaa ggacaaatgg aacctctaaa   1740
attaaaatga aatggggaat ggaaatgagg cgctgcctcc ttcagtctct gcaacagatt   1800
gaaagcatga tcgaagctga gtcctcagtc aaagaaaagg acatgaccaa gaatttttt   1860 gagaacaaat cagagacatg gcctatagga gagtccccca aggagtggga gagggctca   1920 atcgggaagg tttgcaggac cttattagca aaatctgtgt taacagttt atatgcatct   1980 ccacaactgg aagggttttc agctgaatct aggaaattac ttctcattgt tcaggctctt   2040
agggataacc tggaacctgg aacctttgat attgggggt tatatgaatc aattgaggag   2100
tgcctgatta tgatccctg gttttgctt aatgcatctt ggttcaactc cttccttaca   2160
catgcactga agtagttgtg gcaatgctac tatttgctat ccatactgtc caaaaagta   2220 ccttgtttct act                                                      2233
```

<210> SEQ ID NO 14
<211> LENGTH: 2341

-continued

<212> TYPE: DNA
<213> ORGANISM: Influenza A virus

<400> SEQUENCE: 14

```
agcgaaagca ggcaaaccat ttgaatggat gtcaatccga ctctactttt cttaaaggtg     60
ccagcgcaaa atgctataag cacaacattc ccttatactg gagatcctcc ctacagtcat    120
ggaacaggga caggatacac catggatact gtcaacagaa cacaccaata ttcagaaaag    180
gggaaatgga caacaaacac tgagattgga gcaccacaac ttaatccaat cgatggacca    240
cttcctgaag acaatgaacc aagtgggtac gcccaaacag attgtgtatt ggaagcaatg    300
gctttccttg aagaatccca tcccggaatc tttgaaaatt cgtgtcttga aacgatggag    360
gtgattcagc agacaagagt ggacaaacta acacaaggcc gacaaactta tgattggacc    420
ttgaatagga atcaacctgc cgcaacagca cttgctaata caattgaagt gttcagatca    480
aatggtctga cttccaatga atcagggagg ttgatggact tcctcaaaga tgtcatggag    540
tccatgaaca aggaagaaat ggaaataaca acacacttcc aacgaaagag aagagtaaga    600
gacaacatga caaagagaat ggtaacacag agaaccatag ggaagaaaaa acaacgatta    660
aacagaaaga gttatctaat cagaacatta accctaaaca caatgaccaa ggacgctgag    720
agagggaaat tgaaacgacg agcaatcgca accccaggga tgcagataag aggatttgta    780
tattttgttg aaacactagc ccgaagaata tgtgaaaagc ttgaacaatc aggattgcca    840
gttggcggta atgagaaaaa ggccaaactg gctaatgtcg tcagaaaaat gatgactaat    900
tcccaagaca ctgaactctc cttcaccatc actggggaca ataccaaatg gaatgaaaat    960
cagaacccac gcatattcct ggcaatgatc acatacataa ctagaaacca gccagaatgg   1020
ttcagaaatg ttctaagcat tgcaccgatt atgttctcaa ataaaatggc aagactgggg   1080
aaaggatata tgtttgaaag caaaagtatg aaactgagag ctcaaatacc agcagaaatg   1140
ctagcaagca ttgacctgaa atatttcaat gattcaacaa aaaagaaaat taaaaagata   1200
cgaccacttc tggttgacgg gactgcttca ctgagtcctg gcatgatgat gggaatgttc   1260
aacatgttga gcactgtgct gggtgtatcc atattaaacc tgggccagag gaaatacaca   1320
aagaccacat actggtggga tggtctgcaa tcatccgatg actttgcttt gatagtgaat   1380
gcgcctaatc atgaaggaat acaagctgga gtagacagat tctatagaac ttgcaaactg   1440
gtcgggatca acatgagcaa aaagaagtcc tacataaata gaaccggaac attcgaattc   1500
acaagctttt tctaccggta tggttttgta gccaatttca gcatggaact acccagtttt   1560
ggggtttccg gaataaatga atctgcagac atgagcattg gagtgacagt catcaaaaac   1620
aacatgataa ataatgatct cggtcctgcc acggcacaaa tggcactcca actcttcatt   1680
aaggattacc ggtacacata ccggtgccat agaggtgata cccagataca aaccagaaga   1740
tcttttgagt tgaagaaact gtgggaacag actcgatcaa agactggtct actggtatca   1800
gatgggggtc caaacctata taacatcaga aacctacaca tcccggaagt ttgtttaaaa   1860
tgggagctaa tggatgaaga ttataagggg aggctatgca atccattaaa tcctttcgtt   1920
agtcacaaag aaattgaatc agtcaacagt gcagtagtaa tgcctgcgca tggccctgcc   1980
aaaagcatgg agtatgatgc tgttgcaaca acacattctt ggatccccaa gaggaaccgg   2040
tccatattga acacaagcca aaggggaata ctcgaagatg agcagatgta tcagaaatgc   2100
tgcaacctgt ttgaaaaatt cttccccagc agctcataca gaagaccagt cggaatttct   2160
agtatggttg aggccatggt gtccagggcc cgcattgatg cacgaattga cttcgaatct   2220
```

-continued

```
ggacggataa agaaggatga gttcgctgag atcatgaaga tctgttccac cattgaagag   2280
ctcagacggc aaaaatagtg aatttagctt gatcttcatg aaaaaatgcc ttgtttctac   2340
t                                                                   2341

<210> SEQ ID NO 15
<211> LENGTH: 2341
<212> TYPE: DNA
<213> ORGANISM: Influenza A virus

<400> SEQUENCE: 15
agcgaaagca ggtcaaatat attcaatatg gagagaataa agaactgag agatctgatg      60 ttacaatccc gcacccgcga gatactaaca aaaactactg tggaccacat ggccataatc    120
aagaaataca catcaggaag acaagagaag aaccctgcac ttaggatgaa atggatgatg    180
gcaatgaaat acccaattac agcagataag aggataatgg agatgattcc tgagagaaat    240
gaacagggac aaacccttg gagcaaaacg aacgatgctg gctcagaccg cgtaatggta     300
tcacctctgg cagtgacatg gtggaatagg aatggaccaa caacgagcac aattcattat    360
ccaaaagtct acaaaactta ttttgaaaag gttgaaagat tgaaacacgg aaccctttggc  420 cccgttcatt ttaggaatca agtcaagata agacgaagag ttgatgtaaa ccctggtcac    480
gcggacctca gtgccaaaga agcacaagat gtgatcatgg aagttgtttt cccaaatgaa    540
gtgggagcca gaattctaac atcggaatca caactaacaa taaccaaaga gaaaaggaa     600 gaacttcagg actgcaaaat tgctcccttg atggtagcat acatgctaga agagagttg     660 gtccgaaaaa caaggttcct cccagtggca ggcggaacaa gcagtgtata cattgaagtg    720
ttgcatctga ctcagggaac atgctgggag caaatgtaca ccccaggagg agaagttaga    780
aacgatgata ttgatcaaag tttaattatt gcagcccgga catagtgag aagagcgaca     840 gtatcagcag atccactagc atccctactg gaaatgtgcc acagtacaca gattggtgga    900
ataaggatgg tagacatcct taagcagaat ccaacagagg aacaagctgt ggatatatgc    960
aaagcagcaa tgggattgag aattagctca tcattcagct tggtggatt caccttcaaa    1020 agaacaagtg gatcatcagt caagagagaa gaagaaatgc ttacgggcaa ccttcaaaca   1080
ttgaaaataa gagtgcatga gggctatgaa gaattcacaa tggtcggaag aagagcaaca   1140
gccattctca gaaaggcaac cagaagattg attcaattga tagtaagtgg gagagatgaa   1200
caatcaattg ctgaagcaat aattgtagcc atggtgtttt cgcaagaaga ttgcatgata   1260
aaagcagttc gaggcgattt gaactttgtt aatagagcaa atcagcgttt gaaccccatg   1320
catcaactct tgaggcattt ccaaaaagat gcaaaagtgc ttttccaaaa ttggggaatt   1380
gaacccatcg acaatgtaat gggaatgatt ggaatattgc ctgacatgac cccaagcacc   1440
gagatgtcat tgagaggagt gagagtcagc aaaatgggag tggatgagta ctccagcact   1500
gagagagtgg tggtgagcat tgaccgtttt taagagttc gggatcaaag gggaaacata   1560
ctactgtccc ctgaagaagt cagtgaaaca aaggaacgg aaaagctgac aataatttat    1620
tcgtcatcaa tgatgtggga gattaatggt cccgaatcag tgttggtcaa tacttatcaa   1680
tggatcatca ggaactggga aattgtaaaa attcagtggt cacaggaccc cacaatgtta   1740
tacaataaga tagaatttga gccattccag tccctggtcc ctaggccac cagaagccaa    1800 tacagcggtt tcgtaagaac cctgtttcag caaatgcgag atgtacttgg aacatttgat   1860
actgctcaaa ataaaaaact cctccctttt gccgctgctc ctccggaaca gagtaggatg   1920
cagttctctt ctttgactgt taatgtaaga ggatcgggaa tgaggatact tgtaagaggc   1980
```

```
aattccccag tgttcaacta caataaagcc actaaaaggc tcacagtcct cggaaaggat    2040
gcaggtgcgc ttactgagga cccagatgaa ggtacggctg gagtagaatc tgctgttcta    2100
agagggtttc tcattttagg taaagaaaac aagagatatg gcccagcact aagcatcaat    2160
gaactaagca aacttgcaaa aggggagaaa gccaatgtac taattgggca aggggacgta    2220
gtgttggtaa tgaaacggaa acgtgactct agcatactta ctgacagcca gacagcgacc    2280
aaaaggattc ggatggccat caattagtgt tgaattgttt aaaaacgacc ttgtttctac    2340
t                                                                    2341

<210> SEQ ID NO 16
<211> LENGTH: 1762
<212> TYPE: DNA
<213> ORGANISM: Influenza A virus

<400> SEQUENCE: 16
agcaaaagca ggggatattt ctgtcaatca tgaagacaac cattattttg atactactga      60
cccattgggt ctacagtcaa aacccaacca gtggcaacaa cacagccaca ttatgtctgg     120
gacaccatgc agtagcaaat ggaacattgg taaaaacaat aactgatgac caaattgagg     180
tgacaaatgc tactgaatta gttcagagca tttcaatagg gaaaatatgc aacaactcat     240
atagagttct agatggaaga aattgcacat taatagatgc aatgctagga gaccccact      300 gtgatgtctt tcagtatgag aattgggacc tcttcataga aagaagcagc gctttcagca     360
gttgctaccc atatgacatc cctgactatg catcgctccg gtccattgta gcatcctcag     420
gaacattgga attcacagca gagggattca catggacagg tgtcactcaa aacggaagaa     480
gtggatcctg caaaagggga tcagccgata gtttctttag ccgactgaat tggctaacaa     540
aatctggaaa ctcttacccc acattgaatg tgacaatgcc taacaataaa aatttcgaca     600
aactatacat ctggggggatt catcacccga gctcaaacga agagcagaca aaattgtaca     660
tccaagaatc aggacgagta acagtctcaa caaaagaag tcaacaaaca ataatcccta     720
acatcggatc tagaccgtgg gtcagggggtc aatcaggcag ataagcata tactggacca    780 ttgtaaaacc tggagatatc ctaatgataa acagtaatgg caacttagtt gcaccgcggg     840
gatattttaa attgaaaaca gggaaaagct ctgtaatgag atcagatgca cccatagaca     900
tttgtgtgtc tgaatgtatt acaccaaatg gaagcatccc caacgacaaa ccatttcaaa     960
atgtgaacaa agttacatat ggaaaatgcc ccaagtatat caggcaaaaac actttaaagc    1020 tggccactgg gatgaggaat gtaccagaaa agcaaatcag aggaatcttt ggagcaatag    1080
cgggattcat agaaaacggc tgggaaggaa tggttgatgg gtggtatgga ttccgatatc    1140
aaaactcgga aggaacagga caagctgcag atctaaagag cactcaagca gccatcgacc    1200
agatcaatgg aaaattaaac agagtgattg aaaggaccaa tgagaaattc catcaaatag    1260
agaaggaatt ctcagaagta aagggagaaa tccaggattt ggagaagtat gtagaagaca    1320
ccaaaataga cctatggtcc tacaatgcag aattgctggt ggctctagaa atcaacata    1380 caattgactt aacagatgca gaaatgaata aattattcga gaagactaga cgccagttaa    1440
gagaaaacgc ggaagacatg ggaggtggat gtttcaagat ataccacaaa tgtgataatg    1500
catgcattgg atcaataaga aatgggacat atgaccatta catatacaga gatgaagcat    1560
taaacaaccg gtttcaaatc aaaggtgttg agttgaaatc aggctacaaa gattggatac    1620
tgtggatttc attcgccata tcatgcttct taatttgcgt tgttcctattg ggtttcatta    1680
```

```
tgtgggcttg ccaaaaggc aacatcagat gcaacatttg catttgagta aactgatagt   1740
taaaaacacc cttgtttcta ct                                           1762

<210> SEQ ID NO 17
<211> LENGTH: 1762
<212> TYPE: DNA
<213> ORGANISM: Influenza A virus

<400> SEQUENCE: 17
agcaaaagca gggatatttt ctgtcaatca tgaagacaac cattattttg atactactga     60
cccattgggt ctacagtcaa acccaacca gtggcaacaa cacagccaca ttatgtctgg    120
gacaccatgc agtagcaaat ggaacattgg taaaaacaat aactgatgac caaattgagg    180
tgacaaatgc tactgaatta gttcagagca tttcaatagg gaaaatatgc aacaactcat    240
atagggttct agatggaaga aattgcacat aatagatgc aatgctagga gacccccact    300
gtgatgtctt tcagtatgag aattgggacc tcttcataga aagaagcagc gctttcagca    360
attgctaccc atatgacatc ctgactatg catcgctccg gtccattgta gcatcctcag    420
gaacattaga attcacagca gagggattca catggacagg tgtcactcaa acggaagaa    480 gtggagcctg caaaagggga tcagccgata gtttctttag ccgactgaat tggctaacaa    540
aatctggaaa ctcttacccc acattgaatg tgacaatgcc taacaataaa aatttcgaca    600
aactatacat ctgggggatt catcacccga gctcaaacaa tgagcagaca aaattgtata    660
tccaagaaac aggacgagta acagtctcaa caaaaagaag tcaacaaaca ataatcccta    720
acatcggatc tagaccgtgg gtcaggggtc aatcaggcag gataagcata tactggacca    780
ttgtaaaacc tggagatatc ctaatgtaa acagcaatgg caacttagtt gcaccgcggg    840
gatattttaa attgagaaca gggagaagct ctgtaatgag atcagatgca cccatagaca    900
tttgtgtgtc tgaatgtatt acaccaaatg gaagcatccc caacgacaaa ccatttcaaa    960
atgtgaacaa agttacatat ggaaaatgcc ccaaatatat caggcaaaac actttaaagc   1020
tggccactgg gatgaggaat gtaccagaaa agcaaatcag aggaatcttt ggagcaatag   1080
cgggattcat agaaaacggc tgggaaggaa tggttgatgg gtggtatgga ttccgatatc   1140
aaaactcgga aggaacagga caagctgcag atctaaagag cactcaagca gccatcgacc   1200
agatcaatgg aaaattaaac agagtgattg aaaggaccaa tgagaaattc catcaaatag   1260
agaaggaatt ctcagaagta aagggagaa tccaggattt ggagaagtat gtagaagaca   1320
ccaaaataga cctatggtcc tacaatgcag aattgctagt ggctctagaa atcaacata   1380 caattgactt aacagacgca gaatgaata aattattcga gaagactaga cgccagttaa   1440
gagaaaacgc ggaagacatg ggaggtggat gtttcaagat ttaccacaaa tgtgataatg   1500
catgcattgg atcaataaga aatgggacat atgaccatta catatacaga gatgaagcat   1560
taaacaaccg atttcaaatc aaaggtgttg aattaaaatc aggctacaaa gattggatac   1620
tgtggatttc attcgccata tcatgcttct taatttgtgt tgttctattg ggtttcatta   1680
tgtgggcttg ccaaaaggc aacatcagat gcaacatttg catttgagta aactgatagt   1740
taaaaacacc cttgtttcta ct                                           1762

<210> SEQ ID NO 18
<211> LENGTH: 1762
<212> TYPE: DNA
<213> ORGANISM: Influenza A virus

<400> SEQUENCE: 18
```

```
agcaaaagca gggatatttt ctgtcaatca tgaaaacaac cattattttg atactactga      60
cccattgggt ctacagtcaa acccaacca gtggcaacaa cacagccaca ttatgtctgg      120
gacaccatgc agtagcaaat ggaacattgg taaaaacaat aactgatgac caaattgagg     180
tgacaaatgc tactgaatta gttcagagca tttcaatagg aaaaatatgc aacaactcat     240
atagggttct agatggaaga aattgcacat taatagatgc aatgctagga gaccctcact    300
gtgatgtctt tcagtatgag aattgggacc tcttcataga aagaagcagc gctttcagca   360
attgctaccc atatgacatc cctgactatg catcgctccg gtccattgta gcatcctcag    420
gaacattaga attcacagca gagggattca catggacagg tgtcactcaa aacggaggaa   480
gtggagcctg caaaagagga tcagccgata gtttctttag ccgactgaat tggctaacaa   540
aatctggaaa ctcttacccc acattgaatg tgacaatgcc taacaataaa aatttcgaca   600
aactatacat ctgggggatt catcacccga gctcaaacaa tgagcagaca aaattgtata    660
tccaagaatc aggacgagta acagtctcaa caaaagaag tcaacaaaca ataatcccta    720
acatcggatc tagaccgtgg gtcaggggtc aatcaggcag gataagcata tactggacca    780
ttgtaaaacc tggagatatc ctaatgataa acagtaatgg caacttagtt gcaccgcggg    840
gatattttaa attgagaaca gggaaaagct ctgtaatgag atcagatgca cccatagaca   900
cttgtgtgtc tgaatgtatt acaccaaatg gaagcatccc caacgacaaa ccatttcaaa    960
atgtgaacaa agttacatat ggaaaatgcc ccaagtatat caggcaaaac actttaaagc   1020
tggccactgg gatgaggaat gtaccagaaa agcaaatcag aggaatcttt ggagcaatag   1080
cgggattcat agaaaacggc tgggaaggaa tggttgatgg gtggtatgga ttccgatatc   1140
aaaactcgga aggaacagga caagctgcag atctcaaagag cactcaagca gccatcgacc   1200
agatcaatgg aaaattaaac agagtgattg aaaggaccaa tgagaaattc catcaaatag   1260
agaaggaatt ctcagaagta gaagggagaa tcaaggactt ggagaagtat gtagaagaca   1320
ccaaaataga cctatggtcc tacaatgcag aattgctggt ggctctagaa aatcaacata   1380
caattgactt aacagatgca gaaatgaata aattattcga gaagactaga cgccagttaa   1440
gagaaaacgc ggaagacatg ggaggtggat gtttcaagat ctaccacaaa tgtgataatg   1500
catgcattgg atcaataaga aatgggacat atgaccatta catatacaaa gatgaagcat   1560
taaacaaccg atttcaaatc aaaggtgttg agttgaaatc aggctacaaa gattggatac   1620
tgtggatttc attcgccata tcatgcttct aatttgcgt tgttctattg ggtttcatta    1680
tgtgggcttg ccaaaaaggc aacatcagat gcaacatttg catttgagta aactgatagt   1740
taaaaacacc cttgtttcta ct                                            1762
```

<210> SEQ ID NO 19
<211> LENGTH: 1762
<212> TYPE: DNA
<213> ORGANISM: Influenza A virus

<400> SEQUENCE: 19

```
agcaaaagca gggatatttt ctgtcaatca tgaagacaac cattattttg atactactga      60
cccattgggt ctacagtcaa acccaacca gtggcaacaa cacagccaca ttatgtctgg      120
gacaccatgc agtagcaaat ggaacattgg taaaaacaat aactgatgac caaattgagg    180
tgacaaatgc tactgaatta gttcagagca tttcaatagg aaaaatatgc aacaactcat    240
atagagttct agatggaaga aattgcacat taatagatgc aatgctagga gacccccact    300
```

```
gtgatgtcttt tcagtatgag aattgggacc tcttcataga aagaagcagc gctttcagca   360
attgctaccc atatgacatc cctgactatg catcgctccg gtccattgta gcatcctcag   420
gaacattgga attcacagca gagggattca catggacagg tgtcactcaa aacggaagaa   480
gtggagcctg caaaagggga tcagccgata gtttctttag ccgactgaat tggctaacaa   540
aatctggaaa ctcttacccc acattgaatg tgacaatgcc taacaataaa atttcgaca   600
aactatacat ctgggggatt catcacccga gctcaaacca acagcaaaca gaattgtaca   660
tccaagaatc aggacgagta acagtctcaa caaaaagaag tcaacaaacg ataatcccta   720
atatcggatc tagaccgtgg gtcagggggtc aatcaggcag ataagcata tactggacca   780
ttgtaaaacc tggagatatc ctaatgataa acagtaatgg caacttagtt gcaccgcggg   840
gatattttaa attgaaaaca gggaaaagct ctgtaatgag atcagatgca cccatagaca   900
tttgtgtgtc tgaatgtatt acaccaaatg gaagcatccc caacgacaaa ccatttcaaa   960
atgtgaacaa agttacatat ggaaaatgcc ccaagtatat caggcaaaac actttaaagc  1020
tggccactgg gatgaggaat gtaccagaaa agcaaatcag aggaatcttt ggagcaatag  1080
cgggattcat agaaaacggc tgggaaggaa tggttgatgg gtggtatgga ttccgatatc  1140
aaaactcgga aggaacagga caagctgcag atctaaagag cactcaagca gccatcgacc  1200
agattaatgg aaaattaaac agagtgattg aaaggaccaa tgagaaattc catcaaatag  1260
agaaggaatt ctcagaagta aagggagaa tccaggactt ggagaagtat gtagaagaca  1320
ccaaaataga cctatggtcc tacaatgcag aattgctggt ggctctagaa atcaacata  1380
caattgactt aacagatgca gaaatgaata aattattcga gaagactaga cgccagttaa  1440
gagaaaacgc ggaagacatg ggaggtggat gtttcaagat ttaccacaaa tgtgataatg  1500
catgcattgg atcaataaga aatgggacat atgaccatta catatacaga gatgaagcat  1560
taaacaaccg atttcaaatc aaaggtgttg agttgaaatc aggctacaaa gattggatac  1620
tgtggatttc attcgccata tcatgcttct taatttgcgt tgttctattg ggtttcatta  1680
tgtgggcttg ccaaaaaggc aacatcagat gcaacatttg catttgagta aactgatagt  1740
taaaaacacc cttgtttcta ct                                           1762

<210> SEQ ID NO 20
<211> LENGTH: 1565
<212> TYPE: DNA
<213> ORGANISM: Influenza A virus

<400> SEQUENCE: 20
agcaaaagca gggtagataa tcactcactg agtgacatca aagtcatggc gtctcaaggc    60
accaaacgat cttatgagca gatggaaact ggtgggggaac gccagaatgc aactgaaatc   120
agagcatctg ttggaaggat ggtgggagga tcggccggt tctatgttca aatgtgtact   180
gagcttaaac tcaacgacca tgaagggcgg ctgattcaga cagcataac aatagaaagg   240
atggtacttt cggcattcga cgaaagaaga aacaagtacc tcgaggagca tcccagtgct   300
gggaaagacc ccaagaaaac gggaggcccg atatacagaa ggagagatgg aaatggatg   360
agagaactca tcctccatga taaagaagaa atcatgagga tctggcgtca ggccaacaat   420
ggtgaagacg ctactgctgg tcttactcat atgatgatct ggcactccaa tctcaatgac   480
accacctacc aaagaacaag ggctcttgtt cgggctggga tggatcccag aatgtgctct   540
ctgatgcaag gatcaactct cccacggaga tctggagctg ccggtgctgc agtgaagggt   600
gttggaacaa tggtaatgga actcatcagg atgatcaaac gcgggataaa tgatcgaaac   660
```

-continued

```
ttctggagag gtgaaaatgg tcgaagaacc agaattgctt atgaaagaat gtgcaacatc    720
ctcaagggga aattccaaac agcagcacaa cgagcaatga tggaccaagt gagggagggc    780
cgcaatcctg gaaatgctga gattgaggat ctcattttct tggcacgatc agcactcatt    840
ctgagaggat cagtagccca taaatcatgc ctacctgcct gtgtttatgg ccttgcagta    900
gccagtgggt atgactttga gaagaggga tactctctgg ttggaattga tccttcaaa    960 ctactccaga acagccaaat tttcagtcta atcagaccga agaaaatcc agcacacaag   1020 agccagctgg tgtggatggc atgccattct gcagcatttg aggacctgag agtttcgaat   1080
ttcattagag gaaccaaagt aatcccaaga ggacagttag caaccagggg agtgcaaatt   1140
gcttcaaatg aaaacatgga gacaatagat tctagcacac tcgaactgag gagcagatat   1200
tgggcaataa ggaccaggag tggggggaac accagtcaac agagagcatc tgcaggacag   1260
ataagtgtgc aacccacttt ctcagtgcag agaaatcttc cctttgaaag gcaaccatt   1320 atggctgcat tcactggaaa cactgagggg aggacttccg acatgagaac ggaaatcata   1380
aggatgatgg aaaatgccag atcagaagat gtgtctttcc aggggcgggg agtcttcgag   1440
ctctcggacg aaaaggcaac gaacccgatc gtgccttcct ttgacatgag caatgaaggg   1500
tcttatttct tcggagacaa tgctgaggag tttgacagtt aaagaaaaat acccttgttt   1560
ctact                                                              1565
```

<210> SEQ ID NO 21
<211> LENGTH: 1096
<212> TYPE: DNA
<213> ORGANISM: Influenza A virus

<400> SEQUENCE: 21

```
gtcaatcatg aagacaacca ttattttgat actactgacc cattgggtct acagtcaaaa    60
cccaaccagt ggcaacaaca cagccacatt atgtctggga caccatgcag tagcaaatgg   120
aacattggta aaaacaataa ctgatgacca aattgaggtg acaaatgcta ctgaattagt   180
tcagagcatt tcaataggga aaatatgcaa caactcatat agggttctag atggaagaaa   240
ttgcacatta atagatgcaa tgctaggaga ccccactgt gatgtctttc agtatgagaa   300
ttgggacctc ttcatagaaa gaagcagcgc tttcagcaat tgctaccat atgacatccc   360 tgactatgca tcgctccggt ccattgtagc atcctcagga acattagaat tcacagcaga   420
gggattcaca tggacaggtg tcactcaaaa cggaggaagt ggagcctgca aaaggggatc   480
agccgatagt ttctttagcc gactgaattg gctaacaaaa tctggaaact cttaccccac   540
attgaatgtg acaatgccta acaataaaaa tttcgacaaa ctatacatct gggggattca   600
tcacccgagc tcaaacaatg agcagacaaa attgtatatc caagaaacag gacgagtaac   660
agtctcaaca aaaagaagtc aacaaacaat aatccctaac atcggatcta ccgtgggt    720 cagggtcaa tcaggcagga taagcatata ctggaccatt gtaaaacctg agatatcct   780 aatgataaac agcaatggca acttagttgc accgcgggga tattttaaat tgagaacagg   840
gagaagctct gtaatgagat cagatgcacc catagacatt tgtgtgtctg aatgtattac   900
accaaatgga agcatcccca cgacaaacc atttcaaaat gtgaacaaag ttacatatgg   960
aaaatgcccc aaatatatca ggcaaaacac tttaaagctg gccactggga tgaggaatgt  1020
accagaaaag caaatcagag gaatctttgg agcaatagcg ggattcatag aaaacggctg  1080
ggaaggaatg gttgat                                                  1096
```

-continued

<210> SEQ ID NO 22
<211> LENGTH: 1061
<212> TYPE: DNA
<213> ORGANISM: Influenza A virus

<400> SEQUENCE: 22
agcaaaagca ggggatattt ctgtcaatca tgaagacaac cattattttg atactactga 60
cccattgggc ctacagtcaa aacccaatca gtggcaacaa cacagccaca ttgtgtctgg 120
gacaccatgc agtagcaaat ggaacattgg taaaaacaat aactgatgat caaattgagg 180
tgacaaatgc tactgaatta gttcagagca tttcaatggg gaaaatatgc aacaactcat 240
atagagttct agatggaaga aattgcacat taatagatgc aatgctagga gacccccact 300
gtgatgtctt tcagtatgag aattgggacc tctttataga aagaagcagc gctttcagca 360
attgctaccc atatgacatc cctgactatg catcgctccg gtccattgta gcatcctcag 420
gaacattgga attcacagca gagggattca catggacagg tgtcactcaa aacggaagaa 480
gtggagcctg caaaagggga tcagccgata gtttctttag ccgactgaat tggctaacaa 540
aatctggaaa ctcttacccc acattgaatg tgacaatgcc taacaataaa aatttcgaca 600
aactatacat ctgggggatt catcacccga gctcaaacca agagcagaca aaattgtaca 660
tccaagaatc aggacgagta acagtctcaa caaaaagaag tcaacaaaca ataatcccta 720
acatcggatc tagaccgtgg gtcaggggtc aatcaggcag gataagcata tactggacca 780
ttgtaaaacc tggagatatc ctaatgataa acagtaatgg caacttagtt gcaccgcggg 840
gatattttaa attgaaaaca gggaaaagct ctgtaatgag atcagatgca cccatagaca 900
tttgtgtgtc tgaatgtatt acaccaaatg gaagcatctc caacgacaaa ccattccaaa 960
atgtgaacaa agttacatat ggaaaatgcc ccaagtatat caggcaaaac actttaaagc 1020
tggccactgg gatgaggaat gaaccagaaa agcaaatcag a 1061

<210> SEQ ID NO 23
<211> LENGTH: 1061
<212> TYPE: DNA
<213> ORGANISM: Influenza A virus

<400> SEQUENCE: 23
agcaaaagca ggggatattt ctgtcaatca tgaagacaac cattattttg atactactga 60
cccattgggt ctacagtcaa aacccaacca gtggcaacaa cacagccaca ttatgtctgg 120
gacaccatgc agtagcaaat ggaacattgg taaaaacaat aactgatgac caaattgagg 180
tgacaaatgc tactgaatta gttcagagca tttcaatagg gaaaatatgc aacaactcat 240
atagagttct agatggaaga aattgcacat taatagatgc aatgctagga gacccccact 300
gtgatgtctt ccagtatgag aattgggacc tcttcataga aagaagcagc gctttcagca 360
attgctaccc atatgacatc cctgactatg catcgctccg gtccattgta gcatcctcag 420
gaacattaga attcacagca gagggattca catggacagg tgtcactcaa aacggaagaa 480
gtggagcctg caaaagggga tcagccgata gtttctttag ccgactgaat tggctaacaa 540
aatctggaaa ctcttacccc acattgaatg tgacaatgcc taacaataaa aatttcgaca 600
aactatacat ctgggggatt catcacccga gctcaaacca aaagcagaca gaattgtaca 660
tccaagaatc aggacgagta acagtctcaa caaaaagaag tcaacaaacg ataatcccta 720
atatcggatc tagaccgtgg gttaggggtc aatcaggcag gataagcata tactggacca 780
ttgtaaaacc tggagatatc ctaatgataa acagtaatgg caacttagtt gcaccgcggg 840

```
gatattttaa attgaaaaca gggaaaagct ctgtaatgag atcagatgca cccatagaca    900
tttgtgtgtc tgaatgtatt acaccaaatg gaagcatccc caacgacaaa ccatttcaaa    960
atgtgaacaa agttacatat ggaaaatgcc ccaagtatat caggcaaaac actttaaagc   1020
tggccactgg gatgaggaat gtaccagaaa agcaaatcag a                       1061
```

<210> SEQ ID NO 24
<211> LENGTH: 1061
<212> TYPE: DNA
<213> ORGANISM: Influenza A virus

<400> SEQUENCE: 24

```
agcaaaagca gggatatttt ctgtcaatca tgaagacaac cattattttg atactactga     60
cccattgggt ctacagtcaa acccaacca gtggaaacaa cacagccaca ttatgtctgg    120
gacaccatgc agtagcaaat ggaacattgg taaaaacaat aactgatgac caaattgagg   180
tgacaaatgc tactgaatta gttcagagca tttcaatagg gaaaatatgc aacaactcat   240
atagagttct agatggaaga aattgcacat taatagatgc aatgctagga gaccccccact   300
gtgatgtctt ccagtatgag aattgggacc tcttcataga aagaagcagc gctttcagca   360
attgctaccc atatgacatc cctgactatg catcgctccg gtccattgta gcatcctcag   420
gaacattgga attcacagca gagggattca catggacagg tgtcactcaa aacggaagaa   480
gtggagcctg caaaagggga tcagccgata gtttctttag ccgactgaat tggctaacaa   540
aatctggaaa ctcttacccc acattgaatg tgacaatgcc taacaataaa aatttcgaca   600
aactatacat ctgggggatt catcacccga gctcaaacca aaagcagaca gaattgtaca   660
tccaagaatc aggacgagta acagtctcaa caaaagaag tcaacaaacg ataatcccta   720
atatcggatc tagaccgtgg gtcaggggtc aatcaggcag ataagcata tactggacca   780
ttgtaaaacc tggagatatc ctaatgataa acagtaatgg caacttagtt gcaccgcggg   840
gatattttaa attgaaaaca gggaaaagct ctgtaatgag atcagatgca cccatagaca   900
tttgtgtgtc tgaatgtatt acaccaaatg gaagcatccc caacgacaaa ccatttcaaa   960
atgtgaacaa agttacatat ggaaaatgcc ccaagtatat caggcaaaac actttaaagc  1020
tggccactgg gatgaggaat gtaccagaaa agcaaatcag a                      1061
```

<210> SEQ ID NO 25
<211> LENGTH: 1061
<212> TYPE: DNA
<213> ORGANISM: Influenza A virus

<400> SEQUENCE: 25

```
agcaaaagca gggatatttt ctgtcaatca tgaagacaac cattattttg atactactga     60
cccattgggt ctacagtcaa acccaacca gtggaaacaa cacagccaca ttatgtctgg    120
gacaccatgc agtagcaaat ggaacattgg taaaaacaat aactgatgac caaattgagg   180
tgacaaatgc tactgaatta gttcagagca tttcaatagg gaaaatatgc aacaactcat   240
ataaagttct agatggaaga aattgcacat taatagatgc aatgctagga gaccccccact   300
gtgatgtctt ccagtatgag aattgggacc tcttcataga aagaagcagc gctttcagca   360
attgctaccc atatgacatc cctgactatg catcgctccg gtccattgta gcatcctcag   420
gaacattaga attcacagca gagggattca catggacagg tgtcactcaa aacggaagaa   480
gtggagcctg caaaagggga tcagccgata gtttctttag ccgactgaat tggctaacaa   540
```

| | |
|---|---|
| aatctggaaa ctcttacccc acattgaatg tgacaatgcc taacaataaa aatttcgaca | 600 |
| aactatacat ctgggggatt catcacccga gctcaaacca acagcagaca gaattgtaca | 660 |
| tccaagaatc aggacgagta acagtctcaa caaaaagaag tcaacaaacg atagtcccta | 720 |
| atatcggatc tagaccgtgg gttaggggtc aatcaggcag gataagcata tactggacca | 780 |
| ttgtaaaacc tggagatatc ctaatgataa acagtaatgg caacttagtt gcaccgcggg | 840 |
| gatatttttaa attgaaaaca gggaaaagct ctgtaatgag atcagatgca cccatagaca | 900 |
| tttgtgtgtc tgaatgtatt acaccaaatg gaagcatccc aacgacaaa ccatttcaaa | 960 |
| atgtgaacaa agttacatat ggaaaatgcc ccaagtatat caggcaaaac actttaaagc | 1020 |
| tggccactgg gatgaggaat ataccagaaa agcaaatcag a | 1061 |

<210> SEQ ID NO 26
<211> LENGTH: 1763
<212> TYPE: DNA
<213> ORGANISM: Influenza A virus

<400> SEQUENCE: 26

| | |
|---|---|
| agcaaaagca ggggatactt tctgtcaatc atgaagacaa ccattatttt gatactactg | 60 |
| acccattggg tctacagtca aaacccaacc agtggcaaca acacagccac actatgtctg | 120 |
| ggacaccatg cagtagcaaa tggaacattg gtaaaaacaa taactgatga ccaaattgag | 180 |
| gtgacaaatg ctactgaatt agttcagagc acttcaatag ggaaatatg caacaaccca | 240 |
| tatagggttc tagatggaag aaactgcaca ttaatagatg caatgctagg agatccccac | 300 |
| tgtgatgttt ttcagtatga aattgggac ctcttcatag aaagaagcag cgctttcagc | 360 |
| aattgctacc catatgacat ccctgactat gcatcgctcc ggtctattgt ggcatcttca | 420 |
| ggaacattag aattcacagc agagggattc acatggacag gtgtcactca aaacggagga | 480 |
| agtggagcct gcagaagggg gtcagccgat agtttctta gccgactgaa ttggctaaca | 540 |
| aaatctggaa attcttaccc cacattgaat gtaacaatgc ctaacaataa caatttcgat | 600 |
| aaactataca tctgggggat ccatcacccg agcacaaaca tgagcagac aaaattgtat | 660 |
| atccaagaat cagggcgagt aacagtctca acaaaaagaa gtcaacaaac aataatcccc | 720 |
| aacatcggat ctagaccgtg gtcaggggt caatcaggca ggataagcat atattggacc | 780 |
| attgtgaaac ctggagatat cctaatgata aacagtaatg gcaacttagt tgcaccgcgg | 840 |
| ggatattttta aaatgcgaac agggaaaagc tctgtaatga gatcagatgc acccatagac | 900 |
| acttgtgtgt ccgagtgtat taccaaat ggaagcatcc ccaacgacaa accatttcaa | 960 |
| aatgtgaaca agttacata tggaaaatgc cccaagtata tcaagcagaa tactttgaag | 1020 |
| ctggccactg ggatgaggaa tgtaccagaa agcaaatca gaggaatctt tggagcaata | 1080 |
| gcgggattca tagaaaacgg ctgggaagga atggttgatg ggtggtatgg attccgatat | 1140 |
| cagaattcgg aaggaacagg acaagctgca gatctaaaga gcactcaagc agccatcgac | 1200 |
| cagatcaatg gaaaattgaa cagagtgatt gaaggacca atgagaaatt ccatcaaata | 1260 |
| gagaaggaat tctcagaagt agaagggaga atccaggact ggagaagta tgtagaagac | 1320 |
| accaaaatag acctatggtc ctacaatgca gagttactgg tggctctaga aaatcaacat | 1380 |
| acgattgact aacgatgc agaaatgaat aaattattcg agaagactag cgccagtta | 1440 |
| agagaaaacg cggaagacat ggggggtgga tgtttcaaga tttatcacaa atgtgataat | 1500 |
| gcatgcattg atcaataag aaatgggaca tatgaccatt acatatacag agatgaagca | 1560 |
| ttaaacaacc gatttcaaat taaaggtgtt gaattgaaat caggctacaa agattggata | 1620 |

```
ctgtggattt cattcgccat atcatgcttc ttaatttgcg ttgttctatt gggtttcatc    1680
atgtgggctt gccaaaaagg caacatcaga tgcaacattt gcatttgagt aaactgataa    1740
ttaaaaacac ccttgtttct act                                            1763

<210> SEQ ID NO 27
<211> LENGTH: 1027
<212> TYPE: DNA
<213> ORGANISM: Influenza A virus

<400> SEQUENCE: 27
agcaaaagca ggtagatatt taaagatgag tcttctaacc gaggtcgaaa cgtacgttct      60
ctctattgta ccatcaggcc ccctcaaagc cgagatcgcg cagagacttg aagatgtctt    120
tgcagggaag aacaccgatc ttgaggcact catggaatgg ctaaagacaa gaccaatcct    180
gtcacctctg actaaaggga ttttaggatt tgtgttcacg ctcaccgtgc ccagtgagcg    240
aggactgcaa cgtagacgct ttgtccaaaa tgcccttagt ggaaacggag atccaaataa    300
catggacaga gcagtaaaac tgtacaagaa gcttaaaaga gaataacat tccatggggc     360 aaaagaggtg gcactcagct attccactgg tgcactagcc agctgcatgg gactcatata    420
caacagaatg gggactgtga caaccgaagt ggcatttggc ctggtatgcg ccacatgtga    480
acagattgct gattcccagc atcgatctca caggcagatg gtgacaacaa ccaacccact    540
aatcagacat gaaaacagaa tggtactagc cagtaccaca gctaaaacca tggagcaggt    600
ggcagggtcg agtgagcagg cagcagaggc catggaggtt gctagtaagg ccaggcagat    660
ggtgcaggca atgaggacca ttgggaccca ccctagctcc agtgccggtt gaaagatga    720 tcttcttgaa aatttgcagg cctaccagaa acggatggga gtgcaaatgc agcggttcaa    780
gtgatcctct cgttattgca gcaagtatca ttgggatctt gcacttgata ttgtggattc    840
ttgatcgcct tttcttcaaa ttcatttatc gtctccttaa atacggtttg aaaagagggc    900
cttctacgga aggagtacct gagtctatga gggaagaata tcggcaggaa cagcagaatg    960
ctgtggatgt tgacgatggt cattttgtca acatagagct ggagtaaaaa actaccttgt   1020
ttctact                                                             1027

<210> SEQ ID NO 28
<211> LENGTH: 890
<212> TYPE: DNA
<213> ORGANISM: Influenza A virus

<400> SEQUENCE: 28
agcaaaagca gggtgacaaa aacataatgg attccaacac tgtgtcaagc tttcaggtag     60
actgttttct ttggcatgtc cgcaaacgat ttgcagacca gaactgggt gatgccccat     120 tccttgaccg cttcgccga gaccagaagt ccctaaaagg aagaggcagc actcttggtc    180
tggacatcga acagccact cgtgcaggaa agcagatagt ggagcggatt ctggaagagg    240
agtcagatga ggcacttaaa atgaccattg cctctgttcc tgcttcacgc tacttaactg    300
acatgactct tgatgagatg tcaagagact ggttcatgct catgcccaag cagaaagtaa    360
caggctccct atgtataagg atggaccagg caatcatgga taagaacatc atactaaaag    420
caaactttag tgtgattttc gaaaggctgg agacactaat actacttaga gctttcaccg    480
aagaaggagc agtcgttggc gaaatttcac cattgccttc tcttccagga catactaatg    540
aggatgtcaa aaatgcaatt gggtcctca tcggaggact taaatggaat gataacacag    600
```

```
ttagaatctc tgaaactcta cagagattcg cttgggagaag cagtcatgag aatgggagac    660
cttcattccc tccaaagcag aaacgaaaaa tggcgagaac aattgagtca gaagtttgaa    720
gaaataaggt ggttgattga agaagtgcga catagattga aaaatacaga aaatagtttt    780
gaacaaataa catttatgca agccttacaa ctattgcttg aagtagaaca agagataaga    840
actttctcgt ttcagcttat ttaatgataa aaaacaccct tgtttctact              890
```

<210> SEQ ID NO 29
<211> LENGTH: 982
<212> TYPE: DNA
<213> ORGANISM: Influenza A virus

<400> SEQUENCE: 29

```
atgagtcttc tgaccgaggt cgaaacgtac gttctctcta tcgtaccatc aggccccctc     60
aaagccgaga tcgcgcagag acttgaagat gtctttgcag ggaagaacac cgatcttgag    120
gcactcatgg aatggctaaa gacaagacca atcctgtcac ctctgactaa agggatttta    180
ggattcgtat tcacgctcac cgtgcccagt gagcgaggac tgcagcgtag acgctttgtc    240
caaaatgccc ttagtggaaa cggagatcca acaacatgg  acagagcagt aaaactgtac    300
aggaaactta aaagagaaat aacattccat ggggcaaaag aggtggcact cagctattcc    360
actggtgcac tagccagctg catgggactc atatacaaca gaatgggaac tgtgacaacc    420
gaagtggcat ttggcctagt atgcgccaca tgtgaacaga ttgctgattc ccagcatcga    480
tctcacaggc agatggtgac aacaaccaac ccattaatca gacatgaaaa cagaatggta    540
ttagccagta ccacggctaa agccatggag cagatggcag ggtcgagtga gcaggcagca    600
gaggccatgg aggttgctag taaggctagg cagatggtac aggcaatgag gaccattggg    660
acccacccta gctccagtgc cggtttgaaa atgatctcc ttgaaaattt gcaggcctac    720
cagaaacgga tgggagtgca aatgcagcga ttcaagtgat cctctcgtta ttgcagcaag    780
tatcattggg atcttgcact tgatattgtg gattcttgat cgccttttct tcaaattcat    840
ttatcgtcgc cttaaaatacg ggttgaaaag agggccttct acggaaggag tacctgagtc    900
tatgagggaa gaatatcggc aggaacagca gaatgctgtg gatgttgacg atggtcattt    960
tgtcaacata gagctggagt aa                                              982
```

<210> SEQ ID NO 30
<211> LENGTH: 982
<212> TYPE: DNA
<213> ORGANISM: Influenza A virus

<400> SEQUENCE: 30

```
atgagtcttc taaccgaggt cgaaacgtac gttctctcta tcgtaccatc aggccccctc     60
aaagccgaga tcgcgcagag acttgaagat gtctttgcag ggaagaacac cgatcttgag    120
gcactcatgg aatggctaaa gacaagacca atcctgtcac ctctgactaa agggatttta    180
ggatttgtgt tcacgctcac cgtgcccagt gagcgaggac tgcagcgtag acgctttgtc    240
caaaatgccc ttagtggaaa cggagatcca acaacatgg  acagagcagt aaaactgtac    300
aggaagctta aaagagaaat aacattccat ggggcaaaag aggtggcact cagctattcc    360
actggtgcac tagccagctg catgggactc atatacaaca gaatgggac  tgtgacaacc    420 gaagtggcat ttggcctggt atgcgccaca tgtgaacaga ttgctgattc ccagcatcga    480
tctcacaggc agatggtgac aacaaccaac ccactaatca gacatgaaaa cagaatggta    540
ctagccagta ccacagctaa agccatggaa cagatggcag ggtcgagtga gcaggcagca    600
```

| | |
|---|---|
| gaggccatgg aggttgctag taaggccagg cagatggtac aggcaatgag gaccattggg | 660 |
| acccacccta gctccagtgc cggtttgaaa gatgatcttc ttgaaaattt gcaggcctac | 720 |
| cagaaacgga tgggagtgca aatgcagcga ttcaagtgac cctctcgtta ttgcagcaag | 780 |
| tatcattggg atcttgcact tgatattgtg gattcttgat cgccttttct tcaaattcat | 840 |
| ttatcgtcgc cttaaatacg gtttgaaaag agggccttct acggaaggag tacctgagtc | 900 |
| tatgagggaa gaatatcggc aggaacagca gaatgctgtg gatgttgacg atggtcattt | 960 |
| tgtcaacata gagctggagt aa | 982 |

<210> SEQ ID NO 31
<211> LENGTH: 838
<212> TYPE: DNA
<213> ORGANISM: Influenza A virus

<400> SEQUENCE: 31

| | |
|---|---|
| atggattcca acactgtgtc aagctttcag gtagactgtt ttctttggca tgtccgcaaa | 60 |
| cgattcgcag accaagaact gggtgatgcc ccattccttg accggcttcg ccgagaccag | 120 |
| aagtccctaa aaggaagagg tagcactctt ggtctggaca tcgaaacagc cactcgtgca | 180 |
| ggaaagcaga tagtggagca gattctggaa gaggaatcag atgaggcact aaaaatgacc | 240 |
| attgcctctg ttcctgcttc acgctactta actgacatga ctcttgatga gatgtcaaga | 300 |
| gactggttca tgctcatgcc caagcagaaa gtaacaggct ccctatgtat aagaatggac | 360 |
| caggcaatca tggataagaa catccatactt aaagcaaact ttagtgtgat tttcgaaagg | 420 |
| ctggaaacac taatactact tagagccttc accgaagaag gagcagtcgt tggcgaaatt | 480 |
| tcaccattgc cttctcttcc aggacatact aatgaggatg tcaaaaatgc aattggggtc | 540 |
| ctcatcggag gacttaaatg gaatgataat acggttagaa tctctgaaac tctacagaga | 600 |
| ttcgcttgga gaagcagtca tgagaatggg agaccttcat tccctccaaa gcagaaacga | 660 |
| aaaatggaga gaacaattga gccagaagtt tgaagaaata agatggttga ttgaagaagt | 720 |
| gcgacataga ttgaaaaata cagaaaatag ttttgaacaa ataacattta tgcaagcctt | 780 |
| acaactattg cttgaagtag aacaagagat aagaactttc tcgtttcagc ttatttaa | 838 |

<210> SEQ ID NO 32
<211> LENGTH: 838
<212> TYPE: DNA
<213> ORGANISM: Influenza A virus

<400> SEQUENCE: 32

| | |
|---|---|
| atggattcca acactgtgtc aagctttcag gtagactgtt ttctttggca tgtccgcaaa | 60 |
| cgatttgcag accaagaact gggtgatgcc ccattccttg accggcttcg ccgagaccag | 120 |
| aagtccctaa aaggaagagg cagcactctt ggtctggaca tcgaaacagc cactcgtgca | 180 |
| ggaaagcaga tagtggagca gattctggaa gaggaatcag atgaggcact aaaaatgacc | 240 |
| attgcctctg ttcctgcttc acgctactta actgacatga ctcttgatga gatgtcaaga | 300 |
| gactggttca tgctcatgcc caagcagaaa gtaacaggct ccctatgtat aaggatggac | 360 |
| caggcaatca tggataagaa catccatacta aaagcaaact ttagtgtgat tttcgaaagg | 420 |
| ctggagacac taatactact tagagccttc accgaagaag gagcagtcgt tggcgaaatt | 480 |
| tcaccattgc cttctcttcc aggacatact aatgaggatg tcaaaaatgc aattggggtc | 540 |
| ctcatcggag gacttaaatg gaatgataat acagttagag tctctgaaac tctacagaga | 600 |

| | |
|---|---|
| ttcgcttgga gaagcagtca tgagaatggg agaccttcat tccctccaaa gcagaaacga | 660 |
| aaaatggcga gaacaattga gccagaagtt tgaagaaata gatggttga ttgaagaagt | 720 |
| gcgacataga ttgaaaaata cagaaaatag ttttgaacaa ataacattta tgcaagcctt | 780 |
| acaactattg cttgaagtag aacaagagat aagaactttc tcgtttcagc ttatttaa | 838 |

<210> SEQ ID NO 33
<211> LENGTH: 1565
<212> TYPE: DNA
<213> ORGANISM: Influenza A virus

<400> SEQUENCE: 33

| | |
|---|---|
| agcaaaagca gggtagataa tcactcactg agtgacatca aagtcatggc gtctcaaggc | 60 |
| accaaacgat cttatgagca gatggaaact ggtggggaac gccagaatgc aactgaaatc | 120 |
| agagcatctg tcggaaggat ggtgggagga tcggccggt tctatgttca gatgtgtact | 180 |
| gagcttaaac tcaacgacca tgaagggcgg ctgattcaga acagcataac aatagaaagg | 240 |
| atggtacttt cggcattcga cgaaagaaga aacaagtacc tcgaggagca tcccagtgct | 300 |
| gggaaagacc ccaagaaaac gggaggcccg atatacagaa ggaaagatgg gaaatggatg | 360 |
| agagaactca tcctccatga taaagaagaa atcatgagga tctggcgtca ggccaacaat | 420 |
| ggtgaagacg ctactgctgg tcttactcat atgatgatct ggcactccaa tctcaatgac | 480 |
| accacatacc aaagaacaag ggctcttgtt cgggctggga tggatcccag aatgtgctct | 540 |
| ctgatgcaag gatcaaccct cccacggaga tctggagctg ccggtgctgc agtaaaaggt | 600 |
| gttggaacaa tggtaatgga actcatcagg atgatcaaac gcgggataaa tgatcgaaat | 660 |
| ttctggagag gtgaaaatgg tcgaagaacc agaattgctt atgaaagaat gtgcaatatc | 720 |
| ctcaaaggga aattccaaac agcagcacaa cgggcaatga tggaccaagt gagggagggc | 780 |
| cgcaatcctg gaaatgctga gattaggat ctcattttct tggcacgatc agcactcatt | 840 |
| ttgagaggat cagtagccca taaatcatgc ctacctgcct gtgtttatgg ccttgcagta | 900 |
| gccagtgggt atgactttga aggaaggaa tactctctgg ttggaattga tccttttcaaa | 960 |
| ctactccaga acagccaaat tttcagtcta atcagaccga agaaaatcc agcacacaag | 1020 |
| agccagttgg tgtggatggc atgccattct gcagcatttg aggacctgag agttttgaat | 1080 |
| ttcattagag gaaccaaagt aatcccaaga ggacagttag caaccagagg agtgcaaatt | 1140 |
| gcttcaaatg aaaacatgga gacaatagat tctagcacac tcgaactgag gagcagatat | 1200 |
| tgggcaataa ggaccaggag tggagggaac accagtcaac agagagcatc tgcaggacag | 1260 |
| ataagtgtgc aacccacttt ctcagtgcag agaaatcttc cctttgaaag agcaaccatt | 1320 |
| atggctgcat tcactgggaa cactgagcgg aggacttccg acatgagaac ggaaatcata | 1380 |
| aggatgatgg aaaatgccag atcagaagat gtgtctttcc aggggcgggg agtcttcgag | 1440 |
| ctctcggacg aaaaggcaac gaacccgatc gtgccttcct ttgacatgag caatgaaggg | 1500 |
| tcttatttct tcggagacaa tgctgaggag tttgacagtt aaagaaaaat acccttgttt | 1560 |
| ctact | 1565 |

<210> SEQ ID NO 34
<211> LENGTH: 2341
<212> TYPE: DNA
<213> ORGANISM: Influenza A virus

<400> SEQUENCE: 34

| | |
|---|---|
| agcaaaagca ggtcaaatat attcaatatg gagagaataa aagaactgag agatctaatg | 60 |

```
tcacagtccc gcacccgcga gatactaaca aaaactactg tggaccatat ggccataatc      120
aagaaataca catcaggaag acaagagaag aaccccgcac ttaggatgaa gtggatgatg      180
gcaatgaaat acccaattac agcagataag aggataatgg aaatgattcc tgagagaaat      240
gaacagggc aaacccttttg gagcaaaacg aacgatgctg gctcagaccg cgtaatggta      300
tcacctctgg cagtgacatg gtggaatagg aatggaccaa caacgagcac aattcattat      360
ccaaaagtct acaaaactta ttttgaaaaa gttgaaaggt taaaacacgg aacctttggc      420
cccgttcatt ttaggaatca agtcaagata agacggagag ttgacgtaaa ccctggtcac      480
gcggacctca gtgccaaaga agcacaagat gtgatcatgg aagttgtttt cccaaatgaa      540
gtgggagcca gaattctaac atcggaatca caactaacaa taaccaaaga gaaaaaagaa      600
gaacttcagg actgcaaaat tgcccccttg atggtagcat acatgctaga aagagagttg      660
gtccgaaaaa caaggttcct cccagtggct ggcggaacaa gcagtgtata cattgaggtg      720
ttgcatctga ctcagggaac gtgctgggaa caaatgtaca ccccaggagg agaagttaga      780
aacgatgaca ttgatcaaag tttaattatt gctgcccgga acatagtgaa agagcgaca      840
gtatcagcag atccactagc atccctgctg gagatgtgcc acagtacaca gattggtgga      900
ataaggatgg tagacatcct taagcagaat ccaacagagg aacaagctgt ggatatatgc      960
aaagcagcaa tggggttaag aattagctca tcattcagct ttggtggatt caccttaag     1020
agaacaagtg gatcatcagt caagagagaa gaagaaatgc ttacgggcaa ccttcaaaca     1080
ttgaaaataa gagtgcatga gggctatgaa gaattccaca ctggtcggaag aagagcaaca     1140
gccattctca gaaagacaac cagaagattg attcaattga tagtaagtgg gagagatgaa     1200
cagtcaattg ctgaagcaat aattgtagcc atggtgtttt cgcaagaaga ttgcatgata     1260
aaagcagttc gaggcgattt gaacttcgtt aatagagcaa atcagcgctt gaaccccatg     1320
catcaactct tgaggcattt ccaaaaggat gcaaaagtgc ttttccagaa ttgggggatt     1380
gaacccatcg acaatgtgat gggaatgatc ggaatattgc ccgacatgac cccaagcacc     1440
gagatgtcat tgagaggagt gagagtcagc aaaatgggag tggatgagta ctccagcact     1500
gagagagtgg tggtgagcat tgaccgtttt ttaagagttc gggatcaaag gggaaacata     1560
ctactgtccc ctgaagaggt cagtgaaaca caaggaacgg aaaagctgac aataatttat     1620
tcatcatcaa tgatgtggga gattaatggt cccgagtcag tgttggtcaa tacttatcaa     1680
tggatcatca gaaactggga aattgtgaaa attcaatggt cacaggatcc cacaatgtta     1740
tacaataaga tagaatttga gccattccag tccctggtcc ctaggccac cagaagccaa     1800
tacagcggtt tcgtaaggac cctgtttcag caaatgcgag atgtacttgg aacatttgac     1860
actgctcaaa taataaaact cctccctttt gccgctgctc ctccggaaca gagtagaatg     1920
cagttctctt ctttgactgt taatgtaaga ggatcgggaa tgaggatact tgtaagaggc     1980
aattcccag tgttcaacta caacaaagcc actaagaggc tcacagtcct cggaaaggat     2040
gcaggtgcgc ttactgaaga cccagatgaa ggtacggctg gagtagaatc tgctgttctg     2100
agagggtttc tcatcttagg taaagaaaac aagagatatg gcccagcact aagcatcaat     2160
gaactgagca aacttacaaa gggggagaaa gctaatgtgc taattgggca aggggacgtg     2220
gtgttggtaa tgaaacggaa acgtgactct agcatactta ctgacagtca gacagcgacc     2280
aaaaggattc ggatggccat caattagtgt tgaattgttt aaaaacgacc ttgtttctac     2340
t                                                                    2341
```

<210> SEQ ID NO 35
<211> LENGTH: 1762
<212> TYPE: DNA
<213> ORGANISM: Influenza A virus
<220> FEATURE:
<221> NAME/KEY: modified_base
<222> LOCATION: (313)
<223> OTHER INFORMATION: a, c, g, t, unknown or other

<400> SEQUENCE: 35

| | | | | | |
|---|---|---|---|---|---|
| agcaaaagca | gggatatttt | ctgtcaatca | tgaagacaac | cattgttttg | atactactga | 60 |
| cccattgggt | ctacagtcaa | acccaacca | gtggcaacaa | cacagccaca | ttatgtctgg | 120 |
| gacaccatgc | agtagcaaat | ggaacactgg | taaaaacaat | aactgatgac | cagattgagg | 180 |
| tgacaaatgc | tactgaatta | gttcagagca | tttcaatagg | gaaaatatgc | aacaactcat | 240 |
| atagggttct | agatggaaga | aattgcacat | aatagatgc | aatgctagga | gaccccact | 300 |
| gtgatgtttt | tcngtatgag | aattgggacc | tcttcataga | aagaagcagc | gctttcagca | 360 |
| attgctaccc | atatgacatc | cctgactatg | catcgctccg | gtctattgtg | gcatcctcag | 420 |
| gaacattaga | attcacagca | gagggattca | catggacagg | tgtcactcaa | aacggaagaa | 480 |
| gtggagcctg | caaaagggga | tcagccgata | gtttctttag | ccgactgaat | tggctaacaa | 540 |
| aatctggaaa | ttcttacccc | acattgaatg | tgacaatgcc | taacaataac | aatttcgata | 600 |
| aactatacat | ctgggggatt | catcacccga | gctcaaacaa | tgagcagaca | aaattgtata | 660 |
| tccaagaatc | aggacgagta | acagtctcaa | caaaaagaag | tcaacaaaca | ataatccccca | 720 |
| acatcggatc | tagaccgtgg | gtcagggtc | aatcaggcag | gataagcata | tattggacca | 780 |
| ttgtgaaacc | tggagatatc | ctaatgataa | acagtaatgg | caacttagtt | gcaccgcggg | 840 |
| gatatttcaa | attgagaaca | gggaaaagct | ctgtaatgag | atcagatgca | cccatagaca | 900 |
| cttgtgtgtc | tgaatgtatt | acaccaaatg | gaagcatccc | caacgacaaa | ccattccaaa | 960 |
| atgtgaacaa | agttacatat | ggaaaatgcc | ccaagtatat | caggcaaaac | actttgaagc | 1020 |
| tggccactgg | gatgaggaat | gtaccagaaa | agcaaatcag | aggaatcttt | ggagcaatag | 1080 |
| cgggattcat | agaaaacggc | tgggaaggaa | tggttgatgg | gtggtatgga | ttccgatatc | 1140 |
| aaaattcgga | aggaacagga | caagctggag | atctaaagag | cactcaagca | gccatcgacc | 1200 |
| agatcaatgg | aaaattaaac | agagtgattg | aaaggaccaa | tgagaaattc | catcaaatag | 1260 |
| agaaggaatt | ctcagaagta | gaagggagaa | tccaggactt | ggagaagtat | gtagaagaca | 1320 |
| ccaaaataga | cctatggtcc | tacaatgcag | aattgctggt | ggctctagaa | aatcaacata | 1380 |
| caattgactt | aacagatgca | gaaatgaata | aattattcga | gaagactagg | cgccagttaa | 1440 |
| gagaaaacgc | ggaagacatg | ggaggtggat | gtttcaggat | ttaccacaaa | tgtgataatg | 1500 |
| catgcattgg | atcaataaga | aatgggacat | atgaccatta | catatacaga | gatgaagcat | 1560 |
| taaacaaccg | atttcaaatt | aaaggtgttg | agttgaaatc | aggctacaaa | gattggatac | 1620 |
| tgtggatttc | attcgccata | tcatgcttct | taatttgcgt | tgttctattg | ggtttcatta | 1680 |
| tgtgggcttg | ccaaaaaggc | aacatcagat | gcaacatttg | catttgagta | aactgatagt | 1740 |
| taaaaacacc | cttgtttcta | ct | | | | 1762 |

<210> SEQ ID NO 36
<211> LENGTH: 1762
<212> TYPE: DNA
<213> ORGANISM: Influenza A virus
<220> FEATURE:
<221> NAME/KEY: modified_base
<222> LOCATION: (313)
<223> OTHER INFORMATION: a, c, g, t, unknown or other

<400> SEQUENCE: 36

```
agcaaaagca ggggatattt ctgtcaatca tgaagacaac cattatttg atactactga       60
cccattgggt ctacagtcaa aacccaacca gtggcaacaa cacagccaca ttatgtctgg     120
gacaccatgc agtagcaaat ggaacattgg taaaaacaat aactgatgac caaattgagg     180
tgacaaatgc tactgaatta gttcagagca tttcaatagg gaaaatatgc aacaactcat     240
ataggggttct agatggaaga aattgcacat taatagatgc aatgctagga gacccccact     300
gtgatgtttt tcngtatgag aattgggacc tcttcataga aagaagcagc gcttccagca     360
attgctaccc atatgacatc cctgactatg catcgctccg gtctattgtg gcatcctcag     420
gaacattaga attcacagca gagggattca catggacagg tgtcactcaa aacggaagaa     480
gtggagcctg caaaagggga tcagccgata gtttctttag ccgactgaat tggctaacaa     540
aatctggaaa ttcttacccc acattgaatg tgacaatgcc taacaataac aatttcgata     600
agctatacat ctgggggatc catcacccga gctcaaacaa tgagcagaca aaattgtata     660
tccaagaatc aggacgagta acagtctcaa caaaaagaag tcaacaaaca ataatcccca     720
acatcggatc tagaccgtgg gtcaggggtc aatcaggcag gataagcata tattggacca     780
ttgtgaaacc tggagatatc ctaataataa acagtaatgg caacttagtt gcaccgcggg     840
gatatttcaa attgcgaaca gggaaaagct ctgtaatgag atcagatgca cccatagaca     900
cttgtgtgtc tgaatgtatt acaccaaatg gaagcatccc caacgacaaa ccatttcaaa     960
atgtgaacaa agttacatat ggaaaatgcc ccaagtatat caggcaaaac actttgaagc    1020
tggccactgg gatgaggaat gtaccagaaa agcaaatcag aggaatcttt ggagcaatag    1080
cgggattcat agaaaacggc tgggaaggaa tggttgatgg gtggtatgga ttccgatatc    1140
aaaactcgga aggaacagga caagctggag atctaaagag cactcaagca gccatcgacc    1200
agatcaatgg aaaattgaac agagtgattg aaaggaccaa tgagaaattc catcaaatag    1260
agaaggaatt ctcagaagta aagggagaa tccaggactt ggagaagtat gtagaagaca    1320
ccaaaataga cctatggtcc tacaatgcag agttgctggt ggctctagaa aatcaacata    1380
caattgactt aacagatgca gaaatgaata actattcga gaagactagg cgccagttaa    1440
gagaaaacgc ggaagacatg ggaggtggat gtttcaagat ttatcacaaa tgtgataatg    1500
catgcattgg atcaataaga aatgggacat atgaccatta catatacaga gatgaagcat    1560
taaacaaccg atttcaaatt aaaggtgtag agctgaaatc aggctacaaa gattggatac    1620
tgtggatttc attcgccata tcatgcttct taatttgcgt tgttctattg ggtttcatta    1680
tgtgggcttg ccaaaaaggc aacatcagat gcaacatttg catttgagta aactgatagt    1740
taaaaacacc cttgtttcta ct                                             1762
```

<210> SEQ ID NO 37
<211> LENGTH: 693
<212> TYPE: DNA
<213> ORGANISM: Influenza A virus

<400> SEQUENCE: 37

```
atggattcca acactgtgtc aagctttcag gtagactgtt ttctttggca tgtccgcaaa       60
cgatttgcag accaagaact gggtgatgcc ccattccttg accggcttcg ccgagaccag      120
aagtccctaa aaggaagagg tagcactctt ggtctggaca tcgaaacagc cactcgtgca      180
```

```
ggaaagcaga tagtggagca gattctggaa gaggaatcag atgaggcatt ta

```
ctcttcatag aaagaagcag cgctttcagc aattgctacc catatgacat ccctgactat    360
gcatcgctcc ggtccattgt agcatcctca ggaacattgg aattcacagc agagggattc    420
acatggacag gtgtcactca aaacggaaga agtggagcct gcaaaagggg atcagccgat    480
agtttcttta gccgactgaa ttggctaaca aaatctggaa actcttaccc cacattgaat    540
gtgacaatgc ctaacaataa aaatttcgac aaactataca tctgggggat tcatcacccg    600
agctcaaacc aacagcagac agaattgtac atccaagaat caggacgagt aacagtctca    660
acaaaaagaa gtcaacaaac gataatccct aatatcggat ctagaccatg ggtcaggggt    720
caatcaggca ggataagcat atactggacc attgtaaaac ctggagatat cctaatgata    780
aacagtaatg caacttagt tgcaccgcgg ggatatttta aattgaaaac agggaaaagc    840
tctgtaatga gatcagatgc acccatagac atttgtgtgt ctgaatgtat tacaccaaat    900
ggaagcatcc ccaacgacaa accatttcaa aatgtgaaca agttacata tggaaaatgc    960 cccaagtata tcaggcaaaa cactttaaag ctggccactg ggatgaggaa tgtaccagaa   1020
aagcaaatca ga                                                      1032

<210> SEQ ID NO 40
<211> LENGTH: 1032
<212> TYPE: DNA
<213> ORGANISM: Influenza A virus

<400> SEQUENCE: 40
atgaagacaa ccattatttt gatactactg acccattggg tctacagtca aaacccaacc     60
agtggcaaca cacagccac attatgtctg ggacaccatg cagtagcaaa tggaacattg    120
gtaaaaacaa taactgatga ccaaattgag gtgacaaatg ctactgaatt agttcagagc    180
atttcaatag ggaaaatatg caacaactca tatagggttc tagatggaag aaattgcaca    240
ttaatagatg caatgctagg agacccccac tgtgatgttt ttcagtatga aattgggac     300 ctcttcatag aaagaagcag cgctttcagc aattgctacc catatgacat ccctgactat    360
gcatcgctcc ggtccattgt agcatcctca ggaacattag aattcacagc agagggattc    420
acatggacag gtgtcactca aaacggaaga agtggagcct gcaaaagggg atcagccgat    480
agtttcttta gccgactgaa ttggctaaca aaatctggaa attcttaccc catattgaat    540
gtgacaatgc ctaacaataa aaatttcgat aaactataca tctgggggat tcatcacccg    600
agctcaaaca aagagcagac aaaattgtat atccaagaat caggacgagt aacagtctca    660
acagaaagaa gtcaacaaac agtaatccct aacatcggat ctagaccgtg ggtcaggggt    720
caatcaggca ggataagcat atactggacc attgtaaaac ctggagatat tctaatgata    780
aacagtaatg caacttagt tgcaccgcgg ggatatttta aattgagaac agggaaaagc    840
tctgtaatga gatcagatgc actcataggc acttgtgtgt ctgaatgtat tacaccaaat    900
ggaagcatcc ccaacgacaa accatttcaa aatgtgaaca agttacata tggaaaatgc    960 cccaagtata tcaggcaaaa cactttaaag ctggccactg ggatgaggaa tgtaccagaa   1020
aagcaaatca ga                                                      1032

<210> SEQ ID NO 41
<211> LENGTH: 1032
<212> TYPE: DNA
<213> ORGANISM: Influenza A virus

<400> SEQUENCE: 41
```

```
atgaagacaa ccattatttt gatactactg acccattggg tctacagtca aacccaacc    60
agtggcaaca acacagccac attatgtctg ggacaccatg cagtagcaaa tggaacattg   120
gtaaaaacaa taactgatga ccaaattgag gtgacaaatg ctactgaatt agttcagagc   180
atttcaatag ggaaaatatg caacaactca tatagggttc tagatggaag aaattgcaca   240
ttaatagatg caatgctagg acccccat tgtgatgatt ttcagtatga aattgggac      300
ctcttcatag aaagaagcag tgctttcagc aattgctacc catatggcat ccctgactat   360
gcatcgctcc ggtccattgt agcatcctca ggaacattag aattcacagc agagggttc   420
acatggacag gtgtcactca aaacggaaga agtggagcct gcaaaagggg atcagccgat   480
agtttcttta gccgactcaa ttggctaaca aaatctggaa attcttaccc catattgaat   540
gtgacaatgc ctaacaataa aaatttcgat aaactataca tctgggggat tcatcacccg   600
agctcaaaca aagagcagac aaaattatat atccaagaat caggacgagt aacagtctca   660
acagaaagaa gtcaacaaac agtaatccct aacatcggat ctaggccgtg ggtcaggggt   720
caatcaggca ggataagcat atactggacc attgtaaaac ctggagatat tctaatgata   780
aacaataatg caacttagt tgcaccgcgg ggatatttta aattgagaac agggaaaagc    840
tctgtaatga gatcagatgc actcatagac acttgtgtgt ctgaatgtat tacaccaaat   900
ggaagcatcc ccaacgacaa accatttcaa aatgtgaaca agttacata tggaaaatgc   960
cccaagtata tcaggcaaaa cactttaaag ctggccactg ggatgaggaa tataccagaa  1020
aagcaaatca ga                                                      1032
```

<210> SEQ ID NO 42
<211> LENGTH: 1032
<212> TYPE: DNA
<213> ORGANISM: Influenza A virus

<400> SEQUENCE: 42

```
atgaagacaa ccattatttt gatactactg acccattggg tctacagtca aacccaacc    60
agtggcaaca acacagccac attatgtctg ggacaccatg cagtagcaaa tggaacattg   120
gtaaaaacaa taactgatga ccaaattgag gtgacaaatg ctactgaatt agttcagagc   180
atttcaatag ggaaaatatg caacaactca tatagggttc tagatggaag aaattgcaca   240
ttaatagatg caatgctagg acccccac tgtgatgttt ttcagtatga aattgggac      300
ctcttcatag aaagaagcag cgctttcagc aattgctacc catatgacat ctctgactat   360
gcatcgctcc ggtccattgt agcatcctca ggaacattag aattcacagc agagggattc   420
acatggacag gtgtcactca aaacggaaga agtggagcct gcaaaagggg atcagccgat   480
agtttcttta gccgactgaa ttggctaaca aaatctggaa attcttaccc catattgaat   540
gtgacaatgc ctaacaataa aaatttcgat aaactataca tctgggggat tcatcacccg   600
agctcaaaca aagagcagac aaaattgtat atccaagaat caggacgagt aacagtctca   660
acagaaagaa gtcaacaaac agtaatccct aacatcggat ctagaccgtg ggtcaggggt   720
caatcaggca ggataagcat atactggacc attgtaaaac ctggagatat tctaatgata   780
aacagtaatg caacttagt tgcaccgcgg ggatatttta aattgagaac agggaaaagc    840
tctgtaatga gatcagatgc acccataggc acttgtgtgt ctgaatgtat tacaccaaat   900
ggaagcatcc ccaacgacaa accatttcaa aatgtgaaca agttacata tggaaaatgc   960
cccaagtata tcaggcaaaa cactttaaag ctggccactg ggatgaggaa tgtaccagaa  1020
aagcaaatca ga                                                      1032
```

<210> SEQ ID NO 43
<211> LENGTH: 1032
<212> TYPE: DNA
<213> ORGANISM: Influenza A virus

<400> SEQUENCE: 43

```
atgaagacaa ccattatttt gatactactg acccattggg tctacagtca aaacccaacc      60
agtggcaaca acacagccac attatgtctg gacaccatg cagtagcaaa tggaacattg      120
gtaaaaacaa taactgatga ccaaattgag gtgacaaatg ctactgaatt agttcagagc      180
atttcaatag ggaaaatatg caacaactca tatagagttc tagatggaag aaattgcaca      240
ttaatagatg caatgctagg accccccac tgtgatgtct ttcagtatga aattgggac      300
ctcttcatag aaagaagcag cgctttcagc aattgctacc catatgacat ccctgactat      360
gcatcgctcc ggtccattgt agcatcctca ggaacattag aattcacagc agagggattc      420
acatggacag tgtcactca aacggaaga agtggagcct gcaaaagggg atcagccgat      480
agtttcttta gccgactgaa ttggctaaca aatctggaa attcttaccc catattgaat      540
gtgacaatgc ctaacaataa aaatttcgat aaactataca tctgggggat tcatcacccg      600
agctcaaaca agagcagac aaaattgtac atccaagaat caggacgagt aacagtctca      660
acaaaaagaa gtcaacaaac aataatccct aacatcggat ctagaccgtg ggtcaggggt      720
caatcaggca ggataagcat atactggacc attgtaaaac ctggagatat cctaatgata      780
aacagtaatg caacttagt tgcaccgcgg ggatatttta aattgagaac agggaaaagc      840
tctgtaatga gatcagatgc acccatagac atttgtgtgt ctgaatgtat tacaccaaat      900
ggaagcatcc ccagcgacaa accatttcaa aatgtaaaca agttacata tggaaaatgc      960
cccaagtata tcaggcaaaa cactttaaag ctggccactg ggatgaggaa tgtaccagaa      1020
aagcaaatca ga      1032
```

<210> SEQ ID NO 44
<211> LENGTH: 1742
<212> TYPE: DNA
<213> ORGANISM: Influenza A virus

<400> SEQUENCE: 44

```
ctgtcaatca tgaagacaac cattattttg atactactga cccattgggt ctacagtcaa      60
aacccaacca gtggcaacaa cacagccaca ttatgtctgg acaccatgc agtagcaaat      120
ggaacattgg taaaaacaat aactgatgac caaattgagg tgacaaatgc tactgaatta      180
gttcagagca tttcaatagg gaaaatatgc aacaactcat agggttct agatggaaga      240
aattgcacat taatagatgc aatgctagga ccccccact gtgatgtttt tcagtatgag      300
aattgggacc tcttcataga aagaagcagc gctttcagca attgctaccc atatgacatc      360
cctgactatg catcgctccg gtccattgta gcatcctcag gaacattaga attcacagca      420
gagggattca catggacagg tgtcactcaa acggaagaa gtggagcctg caaaagggga      480
tcagccgata gtttctttag ccgactgaat tggctaacaa atctggaaa ttcttacccc      540
atattgaatg tgacaatgcc taacaataaa aatttcgata aactatacat ctggggatt      600
catcacccga gctcaaacaa agagcagaca aaattgtata tccaagaatc aggacgagta      660
acagtctcaa cagaaagaag tcaacaaaca gtaatcccta acatcggatc tagaccgtgg      720
gtcaggggtc aatcaggcag gataagcata tactggacca ttgtaaaacc tggagatatt      780
```

```
ctaacgataa acagtaatgg caacttagtt gcaccgcggg gatattttaa attgagaaca    840
gggaaaagct ctgtaatgag atcagatgca cccatagaca cttgtgtgtc tgaatgtatt    900
acaccaaatg gaagcatccc caacgacaaa ccatttcaaa atgtgaacaa agttacatat    960
ggaaaatgcc ccaagtatat caggcaaaac actttaaagc tggccaccgg gatgaggaat   1020
gtaccagaaa agcaaatcag aggaatcttt ggagcaatag cgggattcat agaaaacggc   1080
tgggaaggaa tggttgatgg gtggtatgga ttccgatatc aaaactcgga aggaacagga   1140
caagctgcag atctaaagag cactcaagca gccatcgacc agatcaatgg aaaattaaac   1200
agagtgattg aaaggaccaa tgagaaattc catcaaatag agaaggaatt ctcagaagta   1260
gaagggagaa tccaggattt ggagaagtat gtagaagaca ccaaaataga cctatggtcc   1320
tacaatgcag aattgctggt ggctctagaa atcaacata caattgactt aacagatgca   1380
gaaatgaata attattcga gaagactagg cgccagttaa gagaaaacgc ggaagacatg   1440
ggaggtggat gtttcaagat ttaccacaaa tgtgataatg catgcattgg atcaataaga   1500
aatgggacat atgaccatta catatacaga gatgaagcat aaacaaccg atttcaaatc   1560 aaaggtgttg agttgaaatc aggctacaaa gattggatac tgtggatttc attcgccata   1620
tcatgcttct aatttgcgt tgttctattg ggtttcatta tgtgggcttg ccaaaaaggc   1680
aacatcagat gcaacatttg catttgagta aactgatagt taaaaacacc cttgtttcta   1740
ct                                                                  1742

<210> SEQ ID NO 45
<211> LENGTH: 1761
<212> TYPE: DNA
<213> ORGANISM: Influenza A virus
<220> FEATURE:
<221> NAME/KEY: modified_base
<222> LOCATION: (1)..(19)
<223> OTHER INFORMATION: a, c, g, t, unknown or other
<220> FEATURE:
<221> NAME/KEY: modified_base
<222> LOCATION: (1760)..(1761)
<223> OTHER INFORMATION: a, c, g, t, unknown or other

<400> SEQUENCE: 45
nnnnnnnnnn nnnnnnnnna aatgaacact cagattctaa tattagccat ttcggcattc     60
ctctgtgtac gtgcagataa aatctgccta ggacatcatg ctgtgtctaa tggaaccaaa    120
gtagacaccc ttactgaaaa gggaatagaa gtcgtcaatg caacagaaac agttgaacaa    180
aaaaacatcc ccaagatctg ctcaaaaggg aaacagacta ttgaccttgg tcaatgtgga    240
ttactaggga ccactattgg tccccccaa tgcgaccaat tcttgaatt ctctgctaat    300 ttaataattg agagaagaga aggtgatgat atttgttatc caggcaaatt tgacaatgaa    360
gaaacattga ccaaatactc agaaaatcc ggaggaatta aaaggagaa tatgggattc    420 acatataccg agtgagaac caatggagag actagcgcct gtagaaggtc aagatcttcc    480
ttttatgcag aaatgaaatg gctcctatct aacacagaca atggggtatt cccacaaatg    540
acaaaatcct acaagaacac taagaaggag ccagctctga taatctgggg aatccaccac    600
tcaggatcaa ctgctgaaca gactagattg tatggaagtg gaaacaagtt gataacagtt    660
tggagttcca ataccaaca atctttgcc ccaaaccctg gaccaggcc gcaaatgaat    720 ggccaatcag gaagaattga cttttactgg ctgatgttag atcccaatga tactgttaat    780 ttcagttta atggggcctt tatagcacct gaccgcgcca gttttctaag aggtaaatct    840
ctaggaattc agagtgacgc acaacttgac aacaattgtg aaggtgaatg ttatcatatt    900
```

```
ggaggtacca taattagcaa cttgcccttt caaaacatta atagcagagc aattgggaaa      960
tgccccagat acgtaaagca aaaaagctta atgctagcaa ccggaatgaa aaatgttcct     1020
gaaaattcta cacacaaaca gttaactcat cacatgcgca aaaaagagg tttatttggt      1080
gcaatagcag gatttattga aaatggatgg aaggattaa tagatggatg gtatggatac      1140
agacatcaga atgcacaagg agaaggaact gctgcagact acaaaagtac acaatctgct     1200
gtcaatcaaa taaccgggaa attaaacaga ctaatagaaa aaaccaacca gcaatttgaa     1260
ctaatagata atgaattcaa tgaaatagaa aagcaaattg gcaatgttat taactggact    1320
agagattcta tcatcgaaat atggtcatat aatgcagaat tcctcgtggc agtggagaat    1380
caacacacta ttgatttaac tgattcagag atgaacaaat tatatgaaaa ggtaagaaga    1440
cagctgagag aaaatgctga ggaagatggt aatggctgtt ttgaaatatt tcaccaatgt    1500
gacaatgatt gcatggccag cattagaaac aatacatatg atcataaaaa atacagaaag   1560
gaggcaatac aaaacagaat tcagattgat gcagtaaagt tgagcagcgg ttacaaagaa    1620
ataatacttt ggtttagctt cggggcatca tgtttcttat ttcttgccat tgcaatggtt    1680
cttgctttca tatgcataaa aaatggaaac atgcggtgca ctatttgtat ataagtttga    1740
aaaaacaccc ttgtttctan n                                              1761
```

<210> SEQ ID NO 46
<211> LENGTH: 1096
<212> TYPE: DNA
<213> ORGANISM: Influenza A virus

<400> SEQUENCE: 46

```
agtcaaaacc caaccagtgg caacaacaca gccacattat gtctgggaca ccatgcagta     60
gcaaatggaa cattggtaaa acaataact gatgaccaaa ttgaggtgac aaatgctact    120
gaattagttc agagcatttc aataggaaa atatgcaaca actcatatag ggttctagat    180
ggaagaaatt gcacattaat agatgcaatg ctaggagacc ccactgtga tgttttcag     240
tatgagaatt gggacctctt catagaaaga agcagcgctt tcagcaattg ctacccatat    300
gacatccctg actatgcatc gctccggtcc attgtagcat cctcaggaac attagaattc    360
acagcagagg gattcacatg gacaggtgtc actcaaaacg gaagaagtgg agcctgcaaa    420
agggatcag ccgatagttt cttttagccga ctgaattggc taacaaaatc tggaaattct    480
tacccccata tgaatgtgac aatgcctaac aataaaaatt tcgataaact atacatctgg    540
gggattcatc acccgagctc aaacaaagag cagacaaaat tgtatatcca agaatcagga    600
cgagtaacag tctcaacaga aagaagtcaa caaacagtaa tccctaacat cggatctaga    660
ccgtgggtca ggggtcaatc aggcaggata agcatatact ggaccattgt aaaacctgga    720
gatattctaa tgataaacag taatggcaac ttagttgctc cgcggggata tttaaattg    780
agaacaggga aaagctctgt aatgagatca gatgcaccca tagacacttg tgtgtctgaa    840
tgtattacac caaatggaag catccccaac gacaaaccat ttcaaaatgt gaacaaagtt    900
acatatggaa aatgccccaa gtatatcagg caaaacactt taaagctggc cactgggatg    960
aggaatgtac cagaaaagca aatcagagga atctttggag caatagaggg attcatagaa   1020
aacggctggg aaggaatggt tgatgggtgg tatggatcc gatatcaaaa ctcggaagga   1080
acaggacaag ctgcag                                                    1096
```

<210> SEQ ID NO 47

-continued

<211> LENGTH: 1086
<212> TYPE: DNA
<213> ORGANISM: Influenza A virus

<400> SEQUENCE: 47

```
ctgtcaatca tgaagacaac cattattttg atactactga cccattgggt ctacagtcaa     60
aacccaacca gtggcaacaa cacagccaca ctatgtctgg gacaccatgc agtagcaaat    120
ggaacattgg taaaaacaat aactgatgac caaattgagg tgacaaatgc cactgaatta    180
gttcagagca cttcaatagg gaaaatatgc aacaacccat atagggttct agatggaaga    240
aactgcacat taatagatgc aatgctagga gatccccact gtgatgtttt tcagtatgag    300
aattgggacc tcttcataga aagaagcagc gctttcagca attgctaccc atatgacatc    360
cctgactatg catcgctccg gtctattgtg gcatcttcag gaacattaga attcacagca    420
gagggattca catggacagg tgtcactcaa aacggaagaa gtggcgcctg cagaagggga    480
tcagccgata gtttctttag ccgactgaat tggctaacaa aatctggaga ttcttacccc    540
acattgaatg tgacaatgcc taacaataac aatttcgata aactatacat ctgggggatc    600
catcacccga gcacaaacaa tgagcagaca aaattgtatg tccaagaatc agggcgagta    660
acagtctcaa caaaaagaag tcaacaaaca ataatcccca acatcggatc tagaccgtgg    720
gtcaggggtc aaccaggcag gataagcata tattggacca ttgtgaaacc tggagatatc    780
ctaatgataa acagtaatgg caacttagtt gcaccgcggg gatatttcaa aatgcgaaca    840
ggaaaaagct ctataatgag atcagatgca cccatagaca cttgtgtgtc cgagtgtatt    900
acaccaaatg gaagcatccc caacgacaaa ccatttcaaa atgtgaacaa agttacatat    960
gggaaatgcc ccaagtatat caagcagaat actttgaagc tggccactgg gatgaggaat   1020
gtaccagaaa agcaaatcag aggaatcttt ggagcaatag cgggattcat agaaaatggc   1080
tgggag                                                               1086
```

<210> SEQ ID NO 48
<211> LENGTH: 982
<212> TYPE: DNA
<213> ORGANISM: Influenza A virus

<400> SEQUENCE: 48

```
atgagtcttc tgaccgaggt cgaaacgtac gttctctcta tcgtaccatc aggccccctc     60
aaagccgaga tcgcgcagag acttgaagat gtctttgcag gaaagaacac cgatcttgag    120
gcactcatgg aatggctaaa gacaagacca atcctgtcac ctctgactaa ggggatttta    180
ggatttgtgt tcacgctcac cgtgcccagt gagcgaggac tgcagcgtag acgctttgtc    240
caaaatgccc ttaatgggaa cggagatcca aacaacatgg acagagcagt aaaactgtac    300
aggaagctta aaagggaaat aacattccat ggggcaaaag aggtggcact cagctattcc    360
actggtgcac tagccagctg catgggactc atatacaaca gaatggggac tgtgacaacc    420
gaagtggcat ttggcctggt atgcgccaca tgtgaacaga ttgctgattc ccagcaccga    480
tctcacagac agatggtgac aacaaccaac ccactaatca gacacgagaa cagaatggta    540
ctagccagta ccacagctaa agccatggag cagatggcag ggtcgagtga gcaggcagca    600
gaggccatgg aggttgctag tcaggccagg cagatggtgc aggcaatgag aaccattggg    660
acccacccta gctccagtgc cggtttgaaa aatgatcttc ttgaaaattt gcaggcctac    720
cagaaacgga tgggagtgca aatgcagcga ttcaagtgat cctctcgtta ttgcagcaag    780
tatcattggg atcttgcact tgatattgtg gattcttgat cgtctttttct tcaaatgcat    840

```
ttatcgtcgt cttaaatacg gtttgaaaag agggccttct acggaaggag tacctgagtc    900
tatgagggaa gaatatcggc aggaacagca gagtgctgtg gatgttgacg atggtcattt    960
tgtcaacata gagctggagt aa                                             982
```

<210> SEQ ID NO 49
<211> LENGTH: 982
<212> TYPE: DNA
<213> ORGANISM: Influenza A virus

<400> SEQUENCE: 49

```
atgagtcttc taaccgaggt cgaaacgtac gttctctcta tcgtaccatc aggcccctc     60
aaagccgaga tcgcgcagag acttgaagat gtctttgcag ggaagaacac cgatcttgag   120
gcactcatgg aatggctaaa gacaagacca atcctgtcac ctctgactaa agggatttta   180
ggatttgtgt tcacgctcac cgtgcccagt gagcgaggac tgcagcgtag acgctttgtc   240
caaaatgccc ttagtggaaa cggagatcca acaacatgg acagagcagt aaaactgtac    300
aggaagctta aaagagaaat aacattccat ggggcaaaag aggtggcact cagctattcc   360
actggtgcac tagccagctg catgggactc atatacaaca gaatggggac tgtgacaacc   420
gaagtggcat ttggcctggt atgcgccaca tgtgaacaga ttgctgattc ccagcatcga   480
tctcacaggc agatggtgac aacaaccaac ccactaatca gacatgaaaa cagaatggta   540
ctagccagta ccacagctaa agccatggag cagatggcag ggtcgagtga gcaggcagca   600
gaggccatgg aggttgctag taaggccagg cagatggtac aggcaatgag gaccattggg   660
acccacccta gctccagtgc cggtttgaaa gatgatcttc ttgaaaattt gcaggcctac   720
cagaaacgga tgggagtgca aatgcagcga ttcaagtgat cctctcgtta ttgcagcaag   780
tatcattggg atcttgcact tgatattgtg gattcttgat cgccttttct tcaaattcat   840
ttatcgtcgc cttaaatacg gtttgaaaag agggccttct acggaaggag tacctgagtc   900
tatgagggaa gaatatcggc aggaacagca gaatgctgtg gatgttgacg atggtcattt   960
tgtcaacata gagctggagt aa                                             982
```

<210> SEQ ID NO 50
<211> LENGTH: 838
<212> TYPE: DNA
<213> ORGANISM: Influenza A virus

<400> SEQUENCE: 50

```
atggattcca acactgtgtc aagctttcag gtagactgtt ttctttggca tgtccgcaaa     60
cgatttgcag accaagaact gggtgatgcc ccattccttg accggcttcg ccgagaccag   120
aagtccctaa aaggaagagg cagcactctt ggtctggaca tcgaaacagc cactcatgca   180
ggaaaagcaga tagtggagcg aattctggaa gaggaatcag atgaggcact taaaatgacc   240
atagcctctg ttcctactc acgctactta actgacatga ctcttgatga tgtcaaga     300
gactggttca tgctcatgcc aagcagaaa gtaacaggct ccctatgtat aaggatggac   360
caagcaatca tggataagaa catcatacta aaagcaaact ttagtgtgat tttcgaaagg   420
ctggagacac taatactact tagagctttc accgaagaag gagcagtcgt tggcgaaatt   480
tcaccattgc cttctcttcc aggacatact aatgaggatg tcaaaaatgc aattggggtc   540
ctcatcggag gacttaaatg gaatgataac acagttagag tctctgaaac tctacagaga   600
ttcgcttgga gaagcagtca tgagaatggg agaccttcat tccctccaaa gcagaaacga   660
```

-continued

```
aaaatggcga gaacaattga gtcagaagtt tgaagaaata aggtggttga ttgaagaagt    720
gagacataga ttgaaaaata cagaaaatag ttttgaacaa ataacattta tgcaagcctt    780
acaactattg cttgaagtag aacaagagat aagaactttc tcgtttcagc ttatttaa     838
```

<210> SEQ ID NO 51
<211> LENGTH: 838
<212> TYPE: DNA
<213> ORGANISM: Influenza A virus

<400> SEQUENCE: 51

```
atggattcca acactgtgtc aagctttcag gtagactgtt ttctttggca tgtccgcaaa     60
cgatttgcag accaagaact gggtgatgcc ccattccttg accggcttcg ccgagaccag    120
aagtccctaa aaggaagagg cagcactctt ggtctggaca tcgaaacagc cactcgtgca    180
ggaaagcaga tagtggagcg gattctggaa gaggagtcag atgaggcact taaaatgacc    240
attgcctctg ttcctgcttc acgctactta actgacatga ctcttgatga gatgtcaaga    300
gactggttca tgctcatgcc caagcagaaa gtaacaggct ccctatgtat aaggatggac    360
caggcaatca tggataagaa catcatacta aaagcaaact ttagtgtgat tttcgaaagg    420
ctggagacac taatactact tagagccttc accgaagaag gagcagtcgt tggcgaaatt    480
tcaccattgc cttctcttcc aggacatact aatgaggatg tcaaaaatgc aattggggtc    540
ctcatcggag gacttaaatg gaatgataat acagttagag tctctgaaac tctacagaga    600
ttcgcttgga gaagcagtca tgagaatggg agaccttcat tccctccaaa gcagaaacga    660
aaaatggcga gaacaattga gccagaagtt tgaagaaata agatggttga ttgaagaagt    720
gcgacataga ttgaaaaata cagaaaatag ttttgaacaa ataacattta tgcaagcctt    780
acaactattg cttgaagtag aacaagagat aagaactttc tcgtttcagc ttatttaa     838
```